(12) United States Patent
Drapeau et al.

(10) Patent No.: US 7,300,773 B2
(45) Date of Patent: Nov. 27, 2007

(54) PRODUCTION OF TNFR-IG

(75) Inventors: Denis Drapeau, Salem, NH (US); Yen-Tung Luan, Chelmsford, MA (US); James R. Mercer, Derry, NH (US); Wenge Wang, North Chelmsford, MA (US); Daniel R. Lasko, Medford, MA (US)

(73) Assignee: Wyeth Research Ireland Limited, Little Connell, Newbridge, County Kildare (IE)

( * ) Notice: Subject to any disclaimer, the term of this patent is extended or adjusted under 35 U.S.C. 154(b) by 119 days.

(21) Appl. No.: 11/213,633

(22) Filed: Aug. 25, 2005

(65) Prior Publication Data

US 2006/0121569 A1   Jun. 8, 2006

Related U.S. Application Data

(60) Provisional application No. 60/605,379, filed on Aug. 27, 2004.

(51) Int. Cl.
*C12P 21/06* (2006.01)

(52) U.S. Cl. .................................................. 435/69.1
(58) Field of Classification Search ................ 435/69.1
See application file for complete search history.

(56) References Cited

U.S. PATENT DOCUMENTS

| | | | |
|---|---|---|---|
| 4,399,216 A | 8/1983 | Axel et al. | 435/6 |
| 4,522,811 A | 6/1985 | Eppstein et al. | 514/2 |
| 4,816,397 A | 3/1989 | Boss et al. | 435/68 |
| 4,816,567 A | 3/1989 | Cabilly et al. | 530/387 |
| 5,122,469 A * | 6/1992 | Mather et al. | 435/383 |
| 5,156,964 A | 10/1992 | Inlow et al. | 435/172.1 |
| 5,395,760 A | 3/1995 | Smith et al. | 435/240.1 |
| 5,447,851 A | 9/1995 | Beutler et al. | 435/69.7 |
| 5,538,983 A | 7/1996 | Buxbaum et al. | |
| 5,589,154 A | 12/1996 | Anderson | 424/1.41 |
| 5,605,690 A | 2/1997 | Jacobs et al. | 424/134.1 |
| 5,658,754 A | 8/1997 | Kawasaki | 435/69.1 |
| 5,672,502 A | 9/1997 | Birch et al. | 435/240.25 |
| 5,705,364 A | 1/1998 | Etcheverry et al. | 435/70.3 |
| 5,712,155 A | 1/1998 | Smith et al. | 435/320.1 |
| 5,721,121 A | 2/1998 | Etcheverry et al. | 435/69.7 |
| 5,856,179 A | 1/1999 | Chen et al. | 435/325 |
| 5,871,999 A | 2/1999 | Boraston | 435/240.25 |
| 5,874,060 A | 2/1999 | Armour et al. | 424/1.49 |
| 5,976,833 A | 11/1999 | Furukawa et al. | 435/69.1 |
| 6,048,728 A | 4/2000 | Inlow et al. | 435/404 |
| 6,180,401 B1 | 1/2001 | Chen et al. | 435/358 |
| 6,291,159 B1 | 9/2001 | Winter et al. | 435/6 |
| 6,310,185 B1 | 10/2001 | Wallace et al. | 530/388.8 |
| 6,518,415 B1 | 2/2003 | Armour et al. | 536/23.53 |
| 6,572,852 B2 | 6/2003 | Smith et al. | 424/85.2 |
| 6,657,103 B1 | 12/2003 | Kucherlapati et al. | 800/6 |
| 2003/0087372 A1 | 5/2003 | DelaCruz et al. | |
| 2003/0104406 A1 | 6/2003 | Wolfman et al. | |
| 2003/0162714 A1 | 8/2003 | Hill et al. | |
| 2003/0180306 A1 | 9/2003 | Hill et al. | |
| 2004/0048368 A1 | 3/2004 | Chen et al. | |
| 2004/0082764 A1 | 4/2004 | Kunz et al. | |
| 2004/0142382 A1 | 7/2004 | Veldman et al. | |
| 2004/0223966 A1 | 11/2004 | Wolfman et al. | |
| 2005/0106154 A1 | 5/2005 | Hill et al. | |
| 2006/0121568 A1 | 6/2006 | Drapeau et al. | |
| 2006/0160180 A1 | 7/2006 | Drapeau et al. | |

FOREIGN PATENT DOCUMENTS

| | | |
|---|---|---|
| EP | 0117058 | 1/1984 |
| EP | 0117060 | 1/1984 |
| EP | 0171496 | 3/1985 |
| EP | 0173494 | 8/1985 |
| EP | 0239400 | 3/1987 |
| EP | 0417563 | 8/1990 |

(Continued)

OTHER PUBLICATIONS

Su-Bin et al. 2004; Construction and production of cancatameric human TNF receptor-immunoglobulin fusion proteins. J. Microbiol. Biotechnol. 14(1): 81-89.*

Abe et al., "The Monoclonal Antibody Directed To Difucosylated Type 2 Chain (Fucα1→2Galβ1→4[Fucα1→3]GlcNAc; Y Determinant)," *J. Biol. Chem.*, 258: 11793-11797, 1983.

Altamirano, et al., "Improvement Of CHO Cell Culture Medium Formulation: Simultaneous Substitution Of Glucose And Glutamine," *Biotechnol. Prog.*, 16: 69-75, 2000.

Altamirano, et al., "Analysis Of CHO Cell Metabolic Redistribution In A Glutamate-Based Defined Medium In Continuous Culutre," *Biotechnol. Prog.*, 17: 1032-1041, 2001.

Bogheart et al., "Antibody-targeted Chemotherapy With The Calicheamicin Conjugate hu3S193-N-acetyl gamma Calicheamicin Dimethyl Hydrazide Targets Lewisy And Eliminates Lewisy-positive Human Carcinoma Cells And Xenografts," *Clin. Can. Res.* 10: 4538-49, 2004.

(Continued)

Primary Examiner—Karen Cochrane Carlson
(74) Attorney, Agent, or Firm—Choate, Hall & Stewart, LLP

(57) ABSTRACT

An improved system for large scale production of proteins and/or polypeptides in cell culture, particularly in media characterized by one or more of: i) a cumulative amino acid concentration greater than about 70 mM; ii) a molar cumulative glutamine to cumulative asparagine ratio of less than about 2; iii) a molar cumulative glutamine to cumulative total amino acid ratio of less than about 0.2; iv) a molar cumulative inorganic ion to cumulative total amino acid ratio between about 0.4 to 1; or v) a combined cumulative glutamine and cumulative asparagine concentration between about 16 and 36 mM, is provided. The use of such a system allows high levels of protein production and lessens accumulation of certain undesirable factors such as ammonium and/or lactate. Additionally, culture methods including a temperature shift, typically including a decrease in temperature when the culture has reached about 20-80% of it maximal cell density, are provided. Alternatively or additionally, the present invention provides methods such that, after reaching a peak, lactate and/or ammonium levels in the culture decrease over time.

108 Claims, 38 Drawing Sheets

FOREIGN PATENT DOCUMENTS

| | | |
|---|---|---|
| EP | 0417014 | 9/1990 |
| EP | 0481791 | 10/1991 |
| GB | 2177096 B | 1/1987 |
| GB | 2251249 | 7/1992 |
| JP | 7165799 | 6/1995 |
| WO | WO92/06193 | 4/1992 |
| WO | WO93/05145 | 3/1993 |
| WO | WO95/24484 | 9/1995 |
| WO | WO96/39488 | 12/1996 |
| WO | WO98/45411 | 10/1998 |
| WO | WO 00/23082 | 4/2000 |
| WO | WO 00/72880 | 12/2000 |
| WO | WO 02/46237 | 6/2002 |
| WO | WO 02/046237 | 6/2002 |
| WO | WO 02/088306 | 11/2002 |
| WO | WO 02/088307 | 11/2002 |
| WO | WO 02/101019 | 12/2002 |
| WO | WO 03/027248 | 4/2003 |
| WO | WO 03/077858 | 9/2003 |
| WO | WO 2006/026445 | 3/2006 |

OTHER PUBLICATIONS

Boshart et al., "A Very Strong Enhancer Is Located Upstream Of An Immediate Early Gene Of Human Cytomegalovirus," *Cell* 41: 521-530, 1985.

Christie and Butler, "The Adaptation Of BHK Cells To A Non-Ammoniagenic Glutamate-Based Culture Medium," *Biotechn. And Bioeng.*, 64(3): 298-309, 1999.

Deutscher, "Setting Up A Laboratory," *Methods in Enzymology*, 182: 19-23, 1990.

Deutscher, "Maintaining Protein Stability," *Methods in Enzymology*, 182: 83-89, 1990.

Deutscher, "Rethinking Your Purification Procedure," *Methods in Enzymology*, 182: 779-780, 1990.

DeVries et al. "The *fms*-Like Tyrosine Kinase, A Receptor For Vascular Endothelial Growth Factor," *Science* 255: 989-991, 1992.

Dijkema et al., "Cloning And Expression Of The Chromosomal Immune Interferon Gene Of The Rat," *EMBO J.* 4(3): 761-767, 1985.

Drews, "Genomic Sciences And The Medicine Of Tomorrow," *Nature Biotechnology*, 14: 1516-1518, 1996.

Gething et al., "Cell-surface Expression Of Influenza Haemagglutinin From A Cloned DNA Copy Of The RNA Gene," *Nature*, 293: 620-625, 1981.

Gorfien, et al., "Optimized Nutrient Additives For Fed-Batch Cultures," *BioPharm International*, 34-40, 2003.

Gorman et al., "The Rous Sarcoma Virus Long Terminal Repeat Is A Strong Promoter When Introduced Into A Variety Of Eukaryotic Cells By DNA-mediated Transfection," *Proc. Natl. Acad. Sci. USA* 79: 67776781, 1982.

Graham and van der Erb, "A New Technique For The Assay Of Infectivity Of Human Adenovirus 5 DNA," *Virology*, 52: 456-457, 1973.

Graham et al., "Characteristics Of A Human Cell Line Transformed By DNA From Human Adenvirus Type 5," *J. Gen Virol.*, 36: 59-74, 1977.

Ham, "Clonal Growth Of Mammalian Cells In A Chemically Defined, Synthetic Medium," *Proc. Nat. Assoc. Sci. USA*, 53: 288-293, 1965.

Jones et al., "Replacing The Complementarity-determining Regions In A Human Antibody With Those From A Mouse," *Nature* 321: 522-525, 1986.

Keown et al., "Methods For Introducing DNA Into Mammalian Cells," *Methods in Enzymology*, 185: 527-537, 1990.

Kozbor et al., "The Production Of Monoclonal Antibodies From Human Lymphocytes," *Immunology Today*, 4: 72-79, 1983.

Ling, et al., "Chemically Characterized Concentrated Corodies For Continuous Cell Culture (The 7C's Culture Media)," *Experimental Cell Research*, 52: 469-489, 1968.

Mansour et al., "Disruption Of The Proto-oncogene *int*-2 In Mouse Embryo-derived Stem Cells: A General Strategy For Targeting Mutations To Non-selectable Genes," *Nature*, 336: 348-352, 1988.

Mantei et al., "Rabbit β-globin mRNA Production In Mouse L Cells Transformed With Cloned Rabbit β-globin Chromosomal DNA," *Nature*, 281: 40-46, 1979.

Mather, "Establishment And Characterization Of Two Distinct Mouse Testicular Epithelial Cell Lines," *Biol. Reprod.*, 23: 243-252, 1980.

Mather et al., "Culture Of Testicular Cells In Hormone-supplemented Serum-free Medium," *Annals N.Y. Acad. Sci.*, 383: 44-68, 1982.

Milligan and Rees, "Chimaeric Gα Proteins: Their Potential Use In Drug Discovery," *TIPS*, 20: 118-124, 1999.

Milstein and Cuello, "Hybrid Hybridomas And Their Use In Immunohistochemistry," *Nature*, 305: 537-540, 1983.

Moore et al., "Culture Of Normal Human Leukocytes," *J. Am. Medical Assn.*, 199: 519-24, 1967.

Morrison et al., "Chimeric Human Antibody Molecules: Mouse Antigen-binding Domains With Human Constant Region Domains," *Proc. Natl. Acad. Sci. U.S.A.* 81: 6851-6855, 1984.

Morton, "A Survey Of Commercially Available Tissue Culture Media," *In Vitro*, 6: 89-108, 1970.

Mustonen and Alitalo, "Endothelial Receptor Tyrosine Kinases Involved In Angiogenesis," *J. Cell Biol.* 129: 895-898, 1995.

Naismith and Sprang, "Tumor Necrosis Factor Receptor Superfamily," *J Inflamm.* 47(1-2): 1-7, 1996.

Okayama, et al., "Bacteriophage Lambda Vector For Transducing A cDNA Clone Library Into Mammalian Cells," *Mol. Cell Biol.* 5: 1136-1142, 1985.

Olsson et al., "Human-Human Monoclonal Antibody-Producing Hybridomas: Technical Aspects," *Meth. Enzymol.*, 92: 3-16, 1983.

Presta, "Antibody Engineering," *Curr. Op. Struct. Biol.* 2: 593-596, 1992.

Riechmann et al., "Reshaping Human Antibodies For Therapy," *Nature* 332: 323-329, 1988.

Sato et al., "Distinct Roles Of The Receptor Tyrosine Kinases Tie-1 and Tie-2 In Blood Vessel Formation," *Nature* 376(6535): 70-74, 1995.

Shibuya et al., "Nucleotide Sequence And Expression Of A Novel Human Receptor-type Tyrosine Kinase Gene (*flt*) Closely Related To The *fms* Family," *Oncogene* 5: 519-524, 1990.

Takeda et al., "Construction Of Chimaeric Processed Immunoglobulin Genes Containing Mouse Variable And Human Constant Region Sequences," *Nature* 314: 452-454, 1985.

Teng et al., "Construction And Testing Of Mouse-Human Hetermyelomas For Human Monoclonal Antibody Production," *Proc. Natl. Acad. Sci. U.S.A.*, 80: 7308-7312, 1983.

Terman et al., "Identification Of A New Endothelial Cell Growth Factor Receptor Tyrosine Kinase," *Oncogene* 6: 1677-83, 1991.

Thomas, et al., "Site-Directed Mutagenesis By Gene Targeting In Mouse Embryo-Derived Stem Cells," *Cell* 51: 503-512, 1987.

Ullrich and Schlessinger, "Signal Transduction By Receptors With Tyrosine Kinase Activity," *Cell* 61: 203-212, 1990.

Urlaub and Chasin, "Isolation Of Chinese Hamster Cell Mutants Deficient In Dihydrofolate Reductase Activity," *Proc. Natl. Acad. Sci. USA*, 77: 4216-4220, 1980.

Xie and Wang, "High Cell Density And High Monoclonal Antibody Production Through Medium Design And Rational Control In A Bioreactor," *Biotechn. And Bioeng.*, 51: 725-729, 1996.

Yarden and Ullrich, "Growth Factor Receptor Tyrosine Kinases," *Ann. Rev. Biochem.* 57: 443-478, 1988.

Bard, et al., "Peripherally Administered Antibodies Against Amyloid Beta-peptide Enter The Central Nervous System And Reduce Pathology In A Mouse Model Of Alzheimer Disease,".

Bibila, et al., "In Pursuit Of The Optimal Fed-Batch Process For Monoclonal Antibody Production," *Biotechnol. Prog.*, 11: 1-13, 1995.

Bols, et al., "Media For Hybridoma Growth And Monoclonal Antibody Production," *Biotech. Adv.*, 6: 169-182, 1988.

Frenkel, et al., "High Affinity Binding Of Monoclonal Antibodies To The Sequential Epitope Efrh Of Beta-amyloid Peptide Is Essential For Modulation Of Fibrillar Aggreation," *J. of Neuroimmunology*, 95: 136-142, 1999.

Graham and Ven der Eb, "A New Technique For The Assay Of Infectivity Of Human Adenovirus 5 DNA," *Virology*, 52: 456-467, 1973.

Kettleborough, et al., "Humanization Of A Mouse Monoclonal Antibody By CDR-Grafting: The Importance Of Framework Residues On Loop Conformation," *Protein Engineering*, 4: 773-783, 1991.

Kundu, et al., "Getting Higher Yields Of Monoclonal Antibody In Culture," *Indian J. Physiol. Pharmacol.*, 42(2): 155-171, 1998.

International Searching Authority, "International Search Report," PCT Application No. PCT/US2005/030364, 7 pgs.

International Searching Authority, "Written Opinion," PCT Application No. PCT/US2005/030364, 5 pgs.

International Searching Authority, "International Search Report," PCT Application No. PCT/US2005/030439, 3 pgs.

Adamson, et al., US Statutory Invention Registration H1532, May 7, 1996. (Filed Nov. 3, 1993).

Notice of Allowance for U.S. Appl. No. 11/213,308 by Drapeau et al., mailed Jun. 8, 2007.

Notice of Allowance for U.S. Appl. No. 11/213,317 by Drapeau et al., mailed Jun. 1, 2007.

European Examination Report for application number 05791655.3 (corresponding to U.S. Appl. No. 11/213,317), mailed Jul. 12, 2007.

European Examination Report for application number 05791482.2 (corresponding to U.S. Appl. No. 11/213,633), mailed Jul. 3, 2007.

* cited by examiner

Figure 1. Comparison of Medium 1 and Medium 2 in shake flasks using anti-GDF-8 cells.
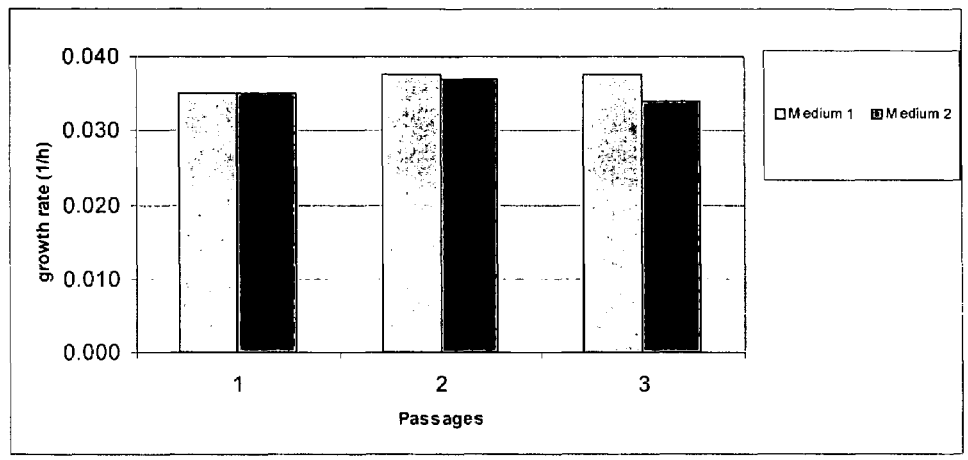
Figure 2. Cell growth and viability of anti-GDF-8 cells in Medium 1.
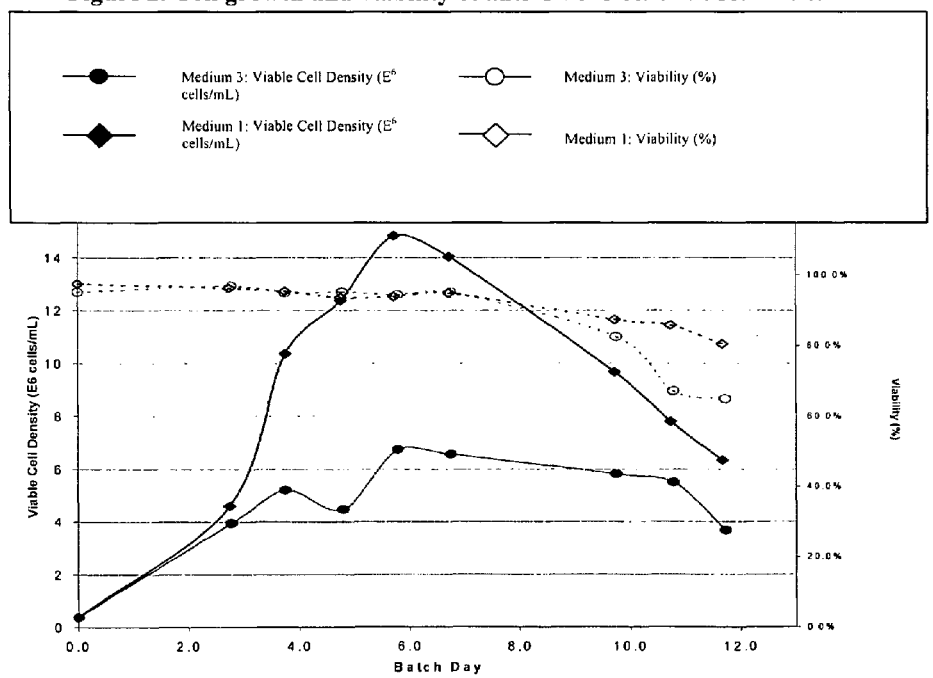

Figure 3. Cell growth of anti-GDF-8 cell cultures in control and no glutamine feed culture conditions.
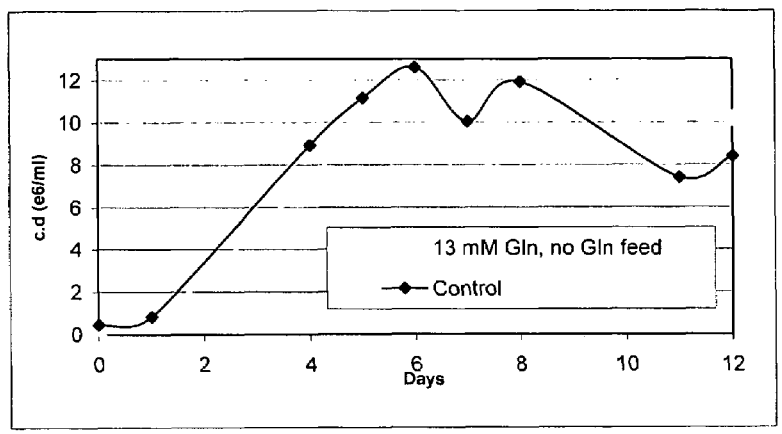
Figure 4. Cell viability of anti-GDF-8 cell cultures in control and no glutamine feed culture conditions.
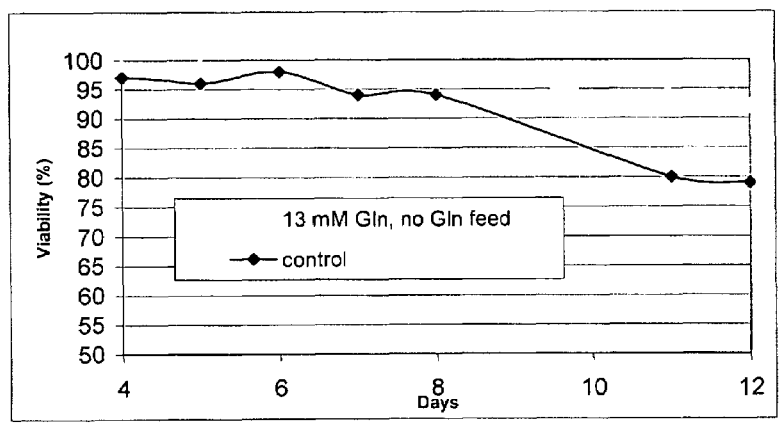

Figure 5. Ammonium levels of anti-GDF-8 cell cultures in control and no glutamine feed culture conditions.
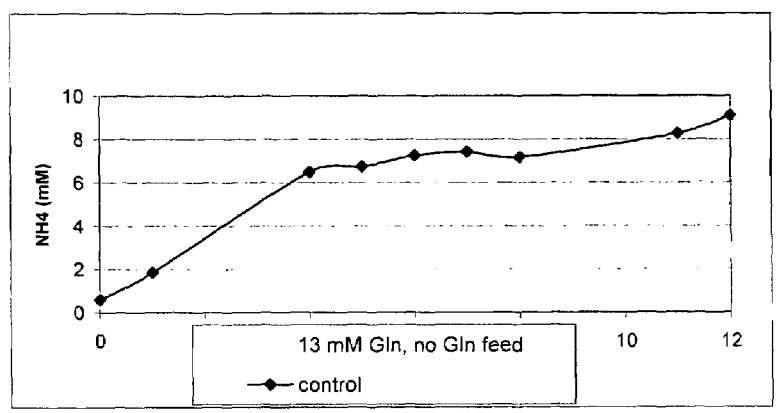
Figure 6. Lactate levels of anti-GDF-8 cell cultures in control and no glutamine feed culture conditions.
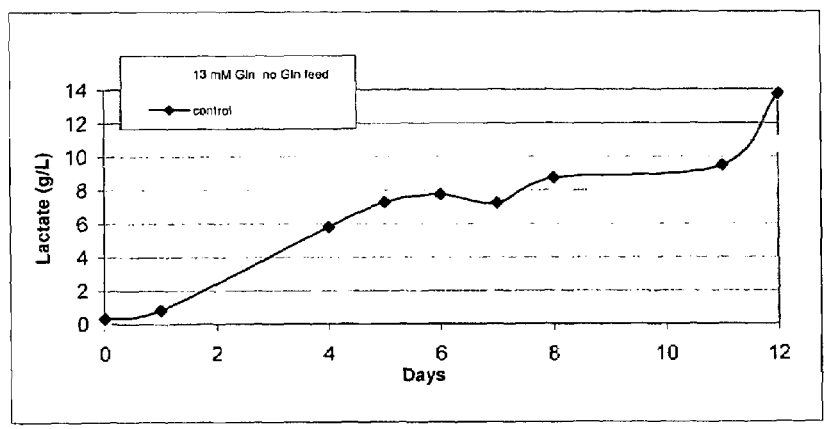

Figure 7. Anti-GDF-8 titer in control and no glutamine feed culture conditions.
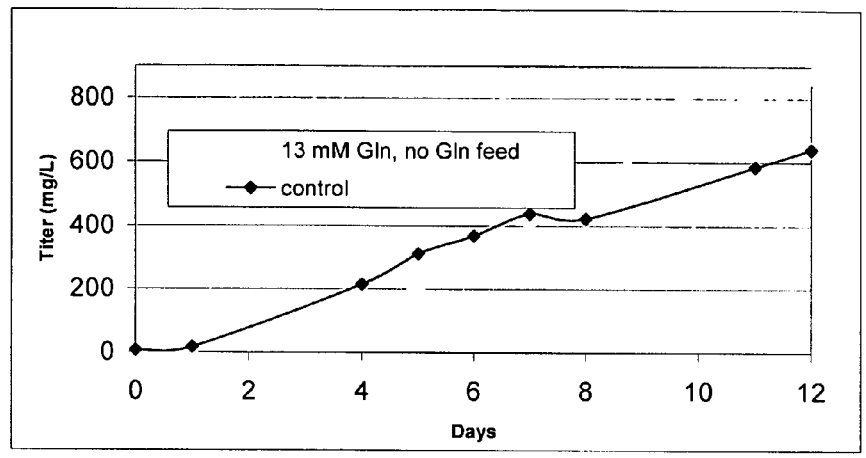
Figure 8. Cell density of anti-GDF-8 cell cultures in control and glutamine-starved feed culture conditions.
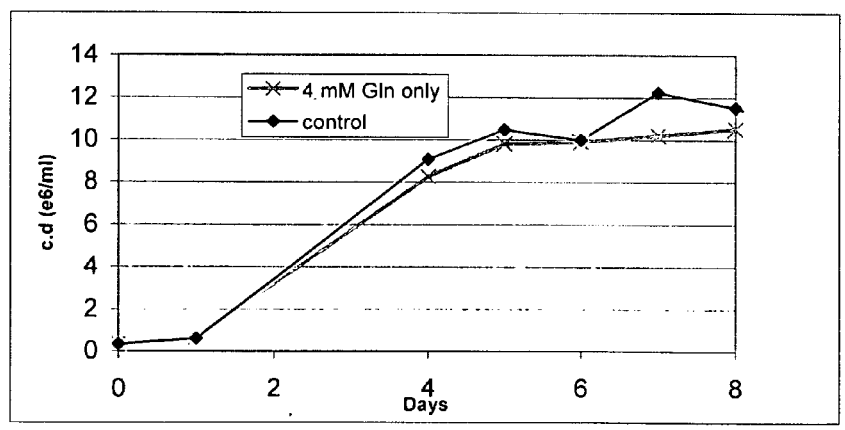

Figure 9. Cell viability of anti-GDF-8 cell cultures in control and glutamine-starved feed culture conditions.
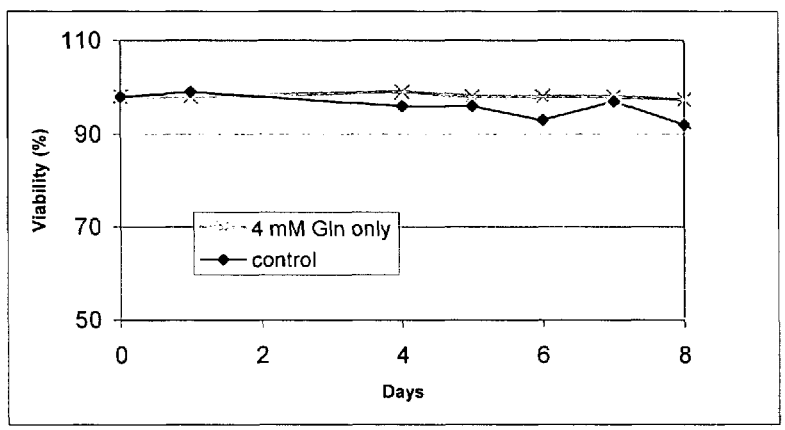
Figure 10. Ammonium levels of anti-GDF-8 cell cultures in control and glutamine-starved culture conditions.
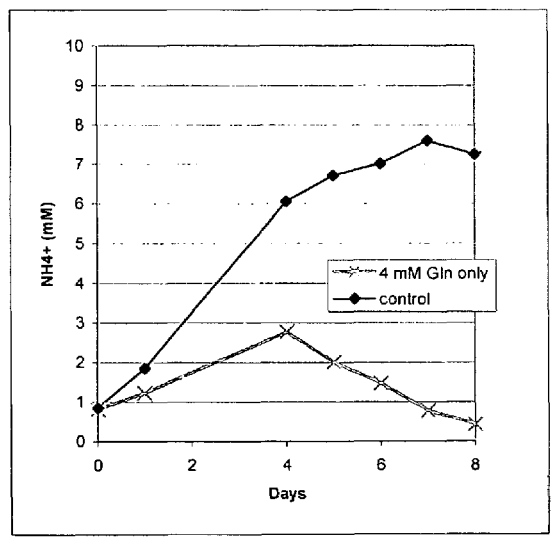

Figure 11. Lactate levels of anti-GDF-8 cell cultures in control and glutamine-starved culture conditions.
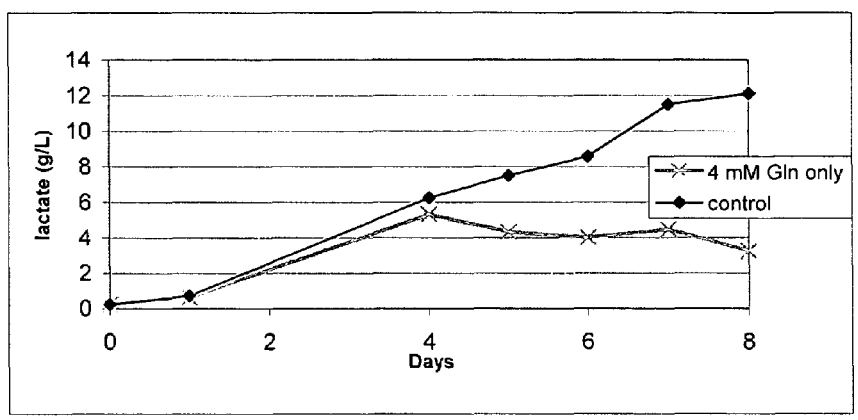
Figure 12. Anti-GDF-8 titer in control and glutamine-starved culture conditions.
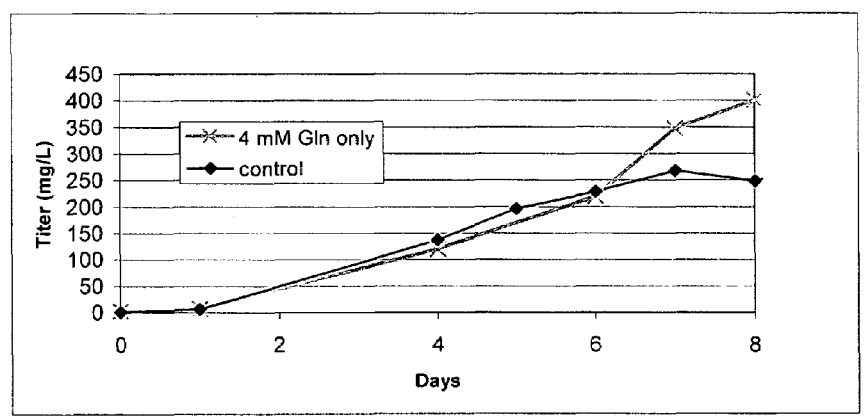

Figure 13. Iron dose response of anti-GDF-8 cells in Medium 1 and Medium 2.
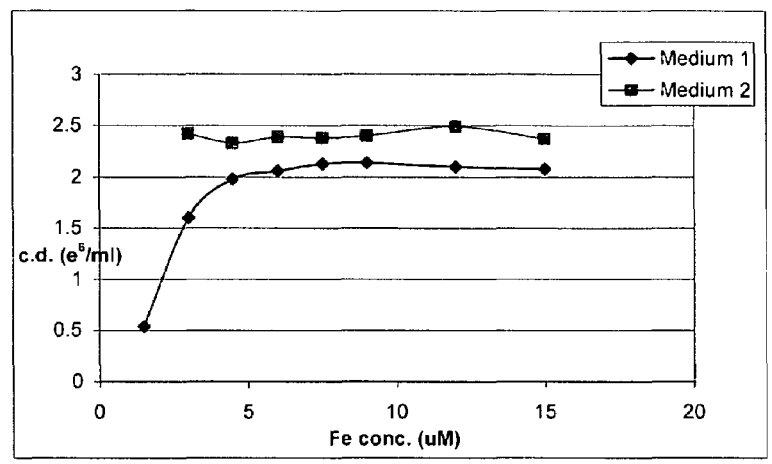
Figure 14. Cell density of Glutamate and Glutamine fed cultures.
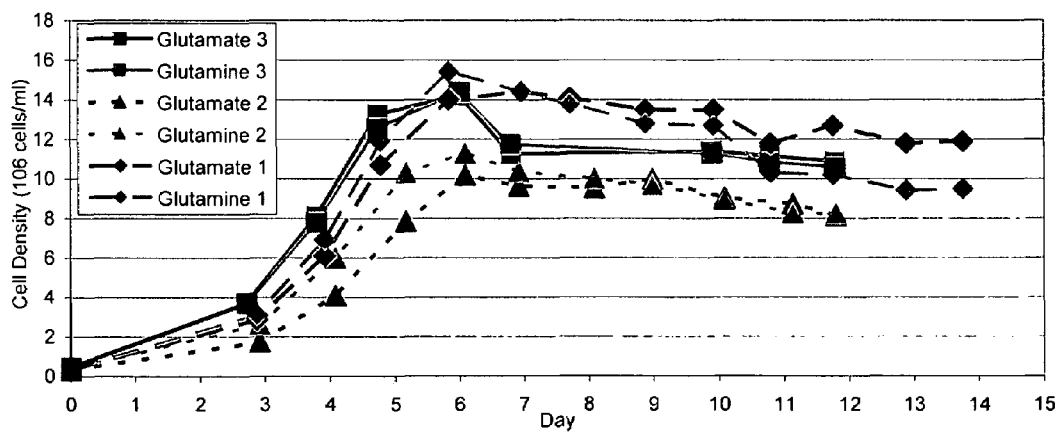

Figure 15. Cell viability of Glutamate and Glutamine fed cultures.
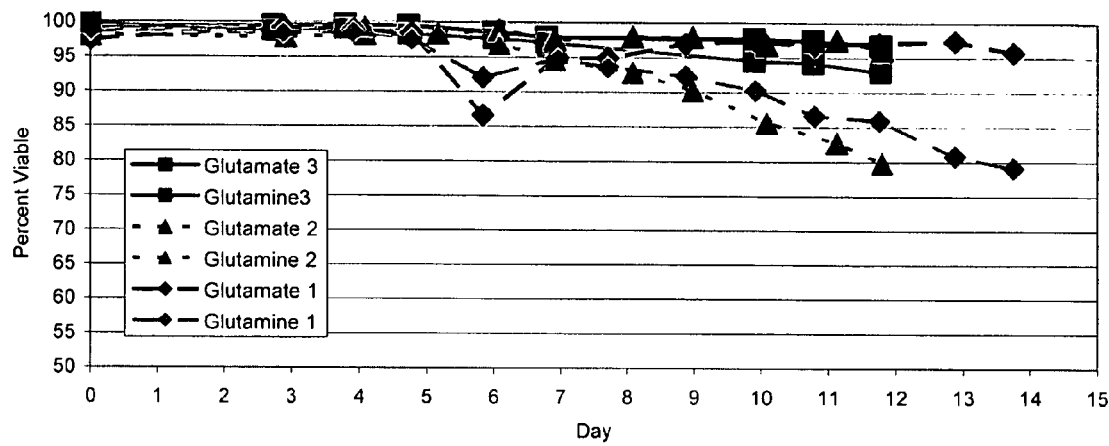
Figure 16. Anti-Lewis Y titer in Glutamate and Glutamine fed cultures.
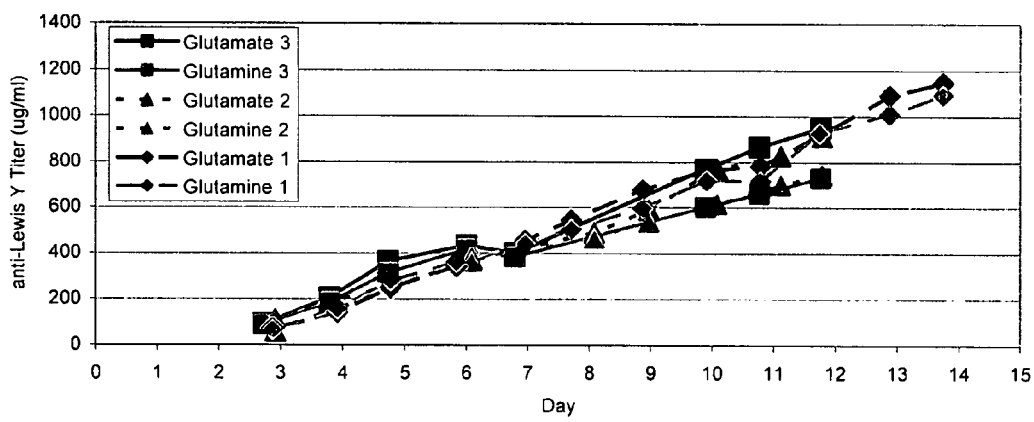

Figure 17. Lactate levels in Glutamate and Glutamine fed cultures.
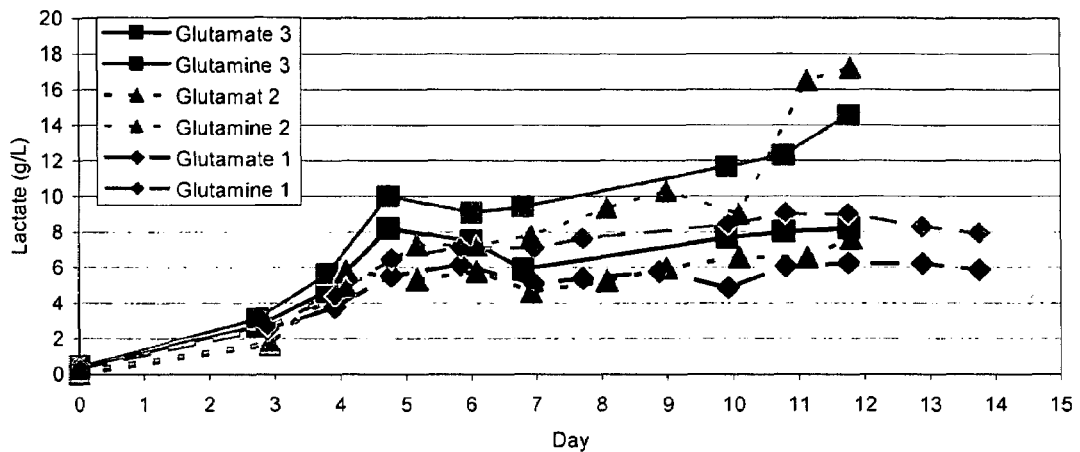
Figure 18. Ammonium levels in Glutamate and Glutamine fed cultures.
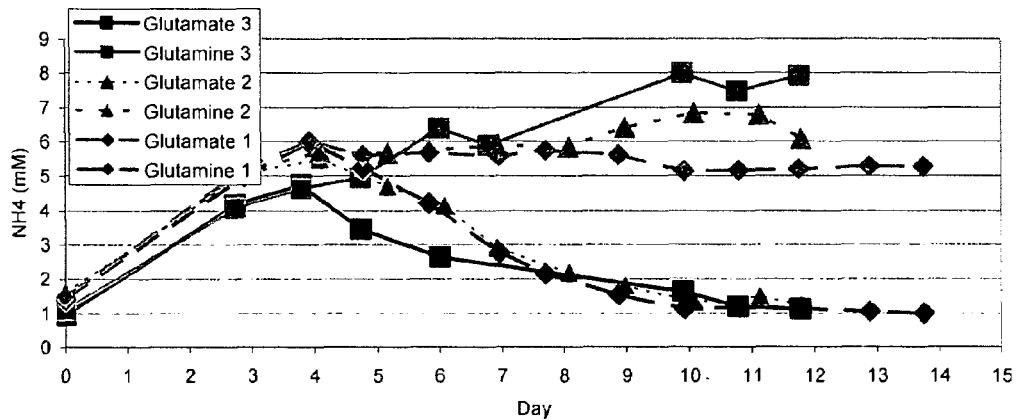
Figure 19. Osmolarity of Glutamate and Glutamine fed cultures.
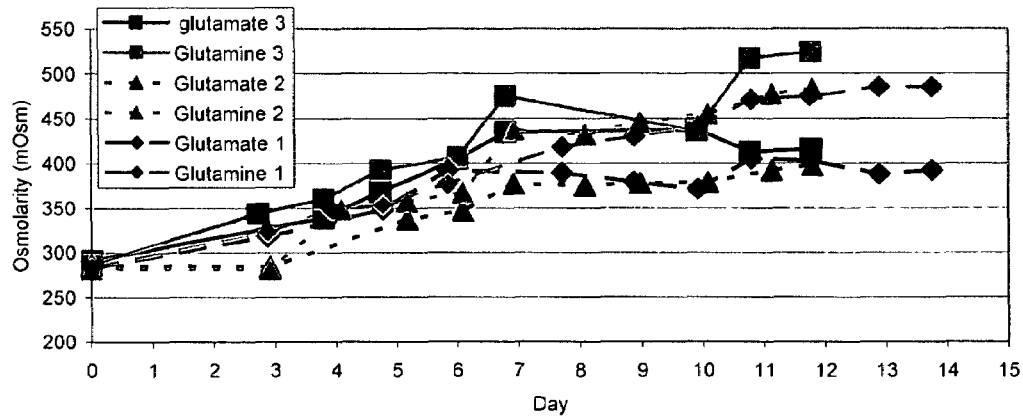

Figure 20. Cell Density. Each plot is the average of two shake flasks grown using the same conditions.
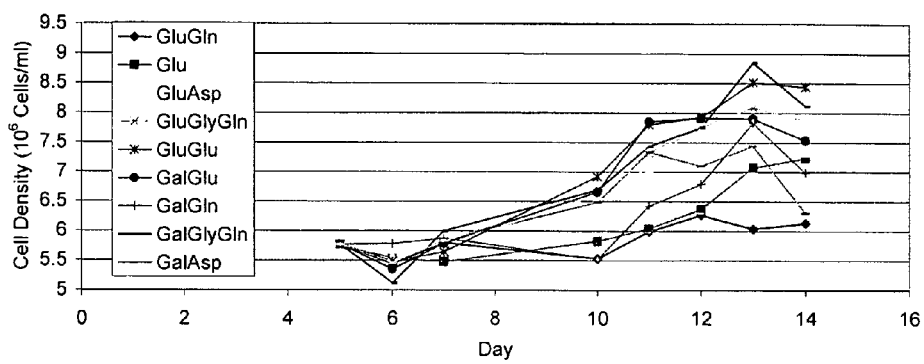
Figure 21. Cell Viability. Each plot is the average of two shake flasks grown using the same conditions.
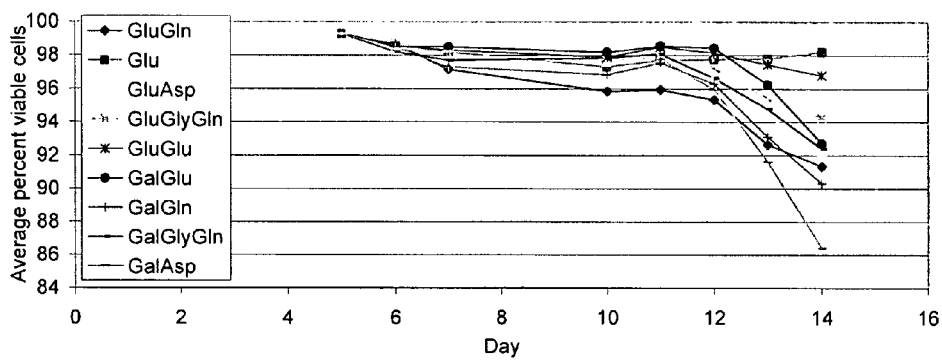
Figure 22. Average Titer. Each plot is the average of two shake flasks grown using the same conditions.
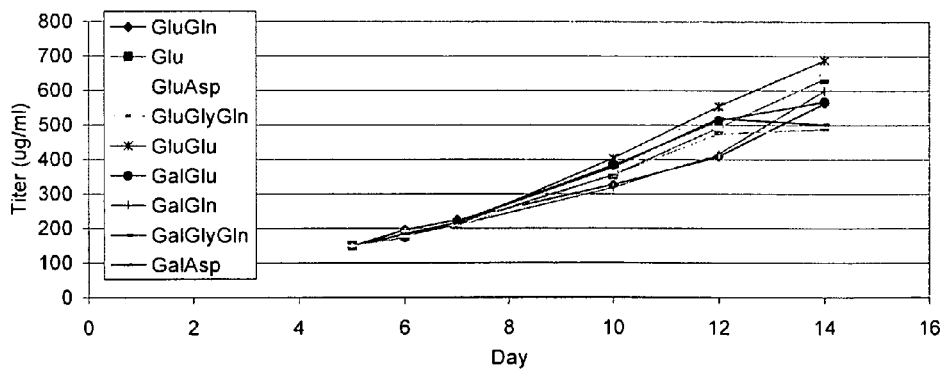

Figure 23. Ammonium levels. Each plot is the average of two shake flasks grown using the same conditions.
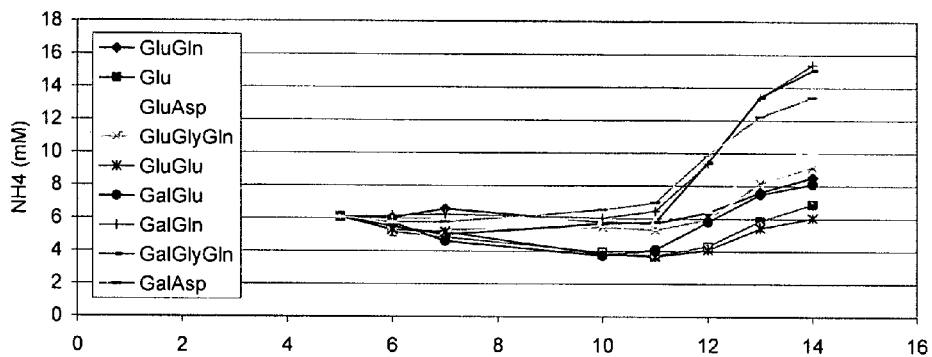
Figure 24. Impeller Jump
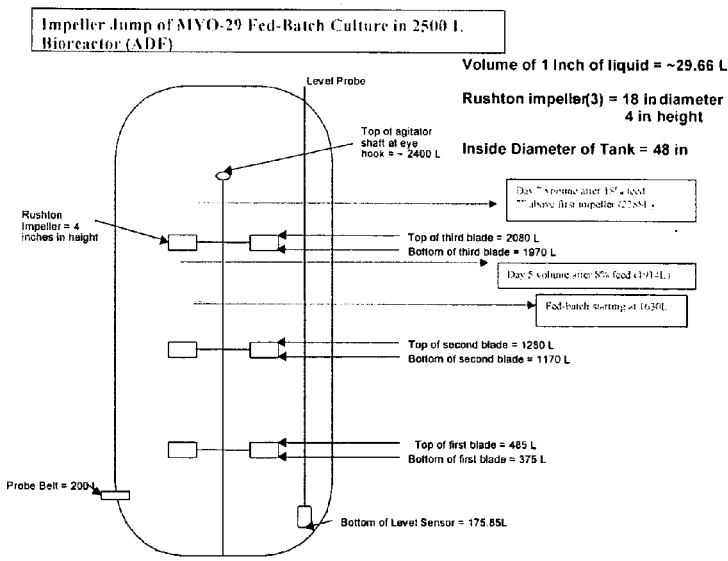

Figure 25. Cell growth of anti-GDF-8 cells under various experimental conditions.
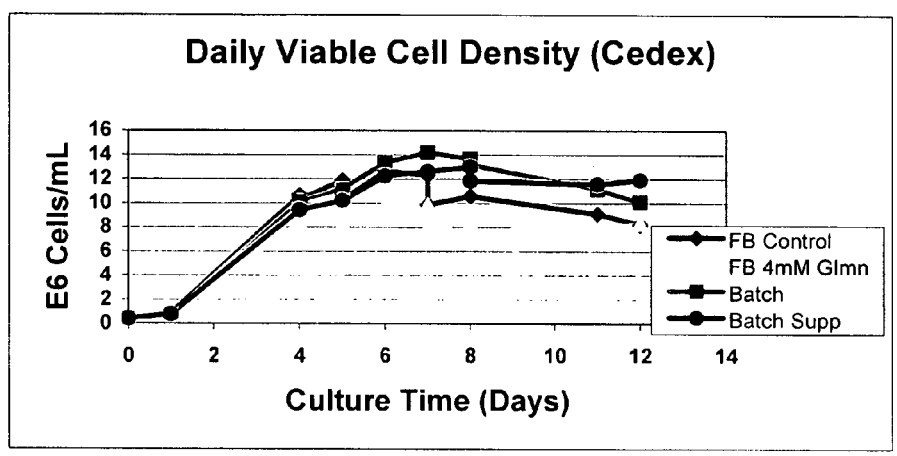
Figure 26. Viability of anti-GDF-8 cells under various experimental conditions.
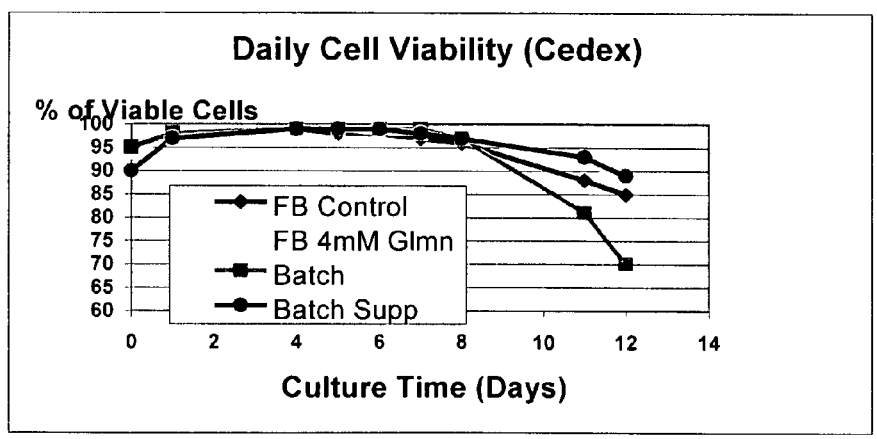

Figure 27. Anti-GDF-8 titer under various experimental conditions.
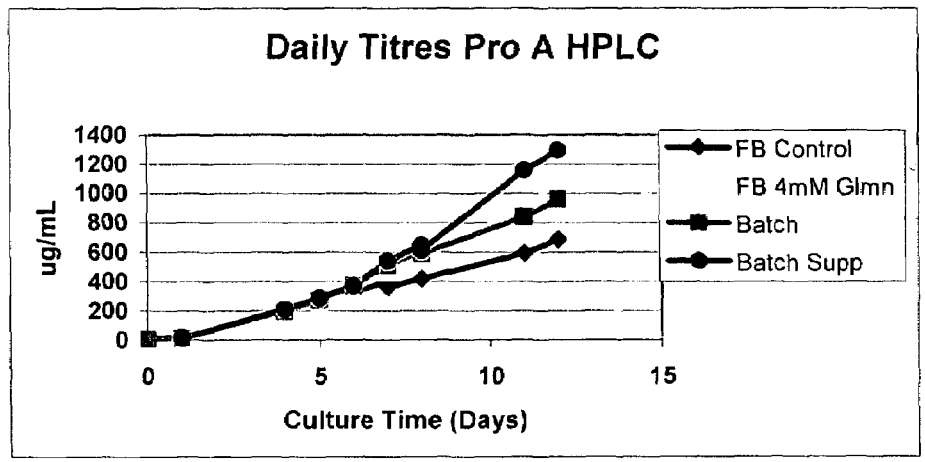
Figure 28. Lactate levels of anti-GDF-8 cultures under various experimental conditions.
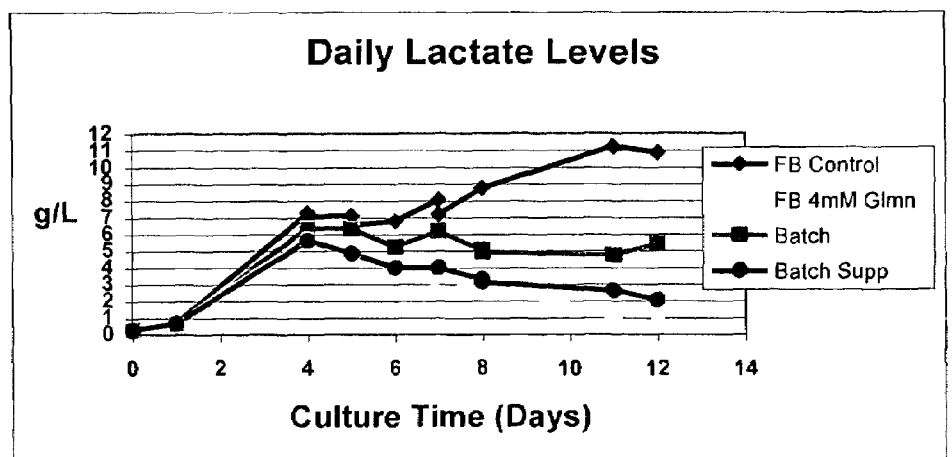

Figure 29. Ammonium levels of anti-GDF-8 cultures under various experimental conditions.
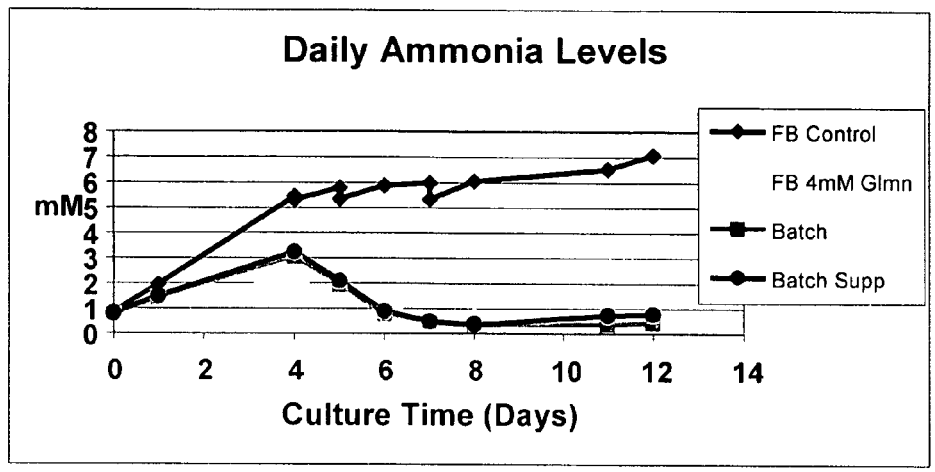
Figure 30. Cell growth of anti-GDF-8 cells under various experimental conditions.
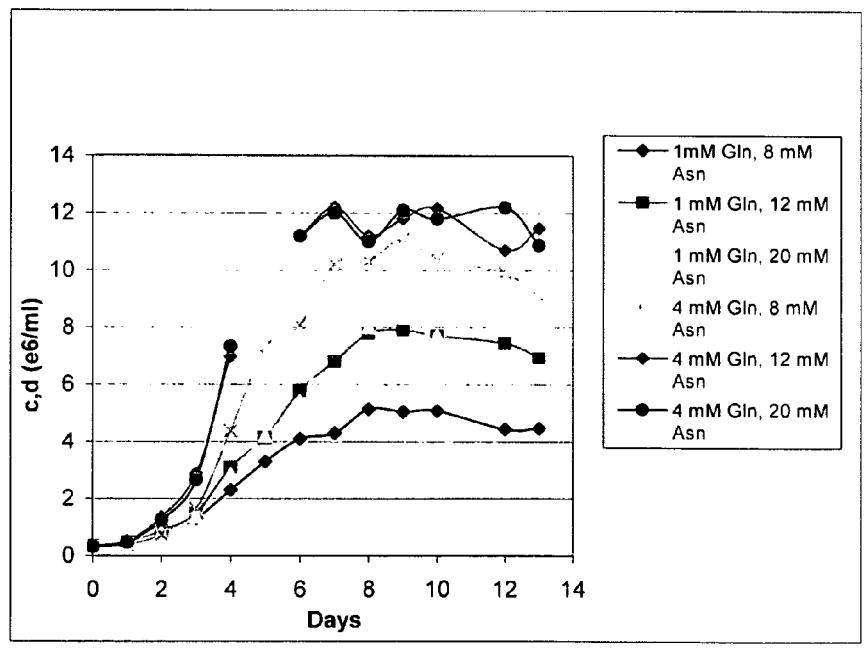

Figure 31. Anti-GDF-8 titer under various experimental conditions.
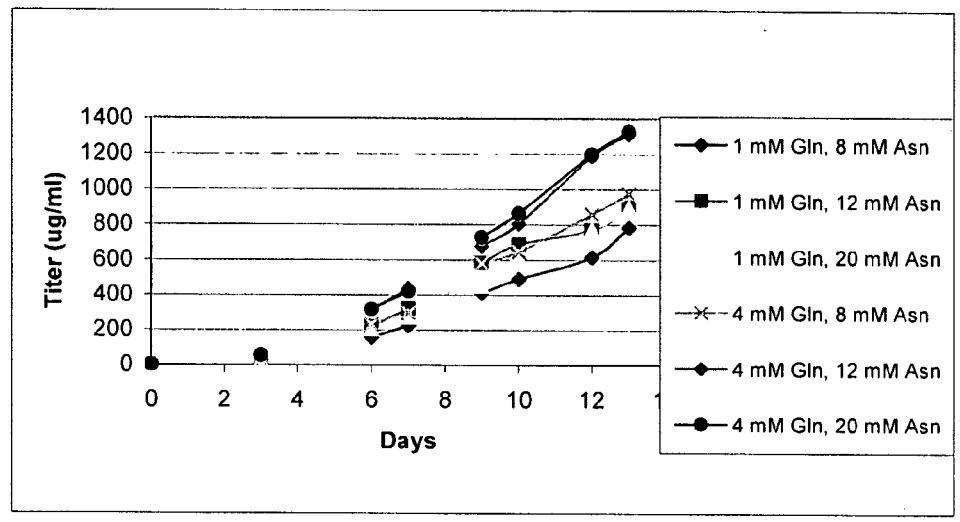
Figure 32. Lactate levels of anti-GDF-8 cultures under various experimental conditions.
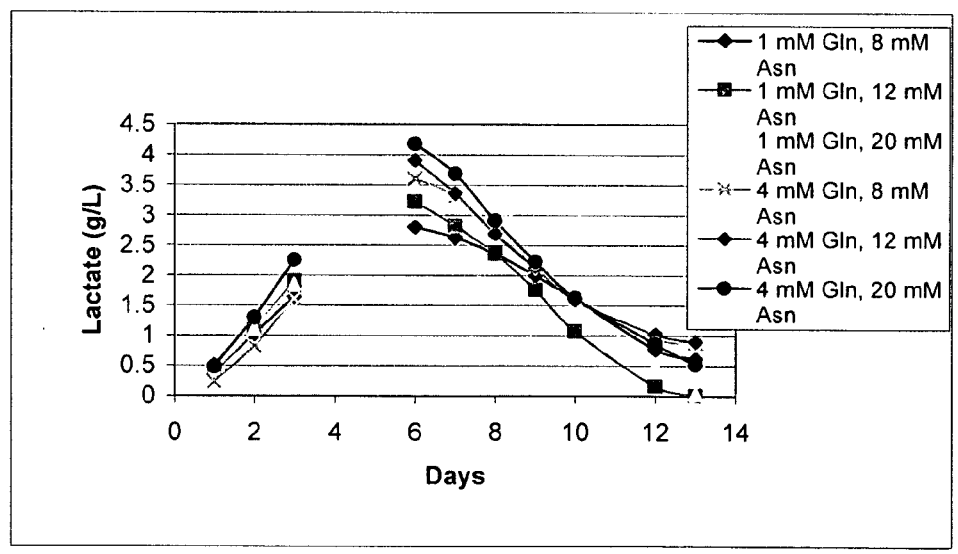

Figure 33. Ammonium levels of anti-GDF-8 cultures under various experimental conditions.
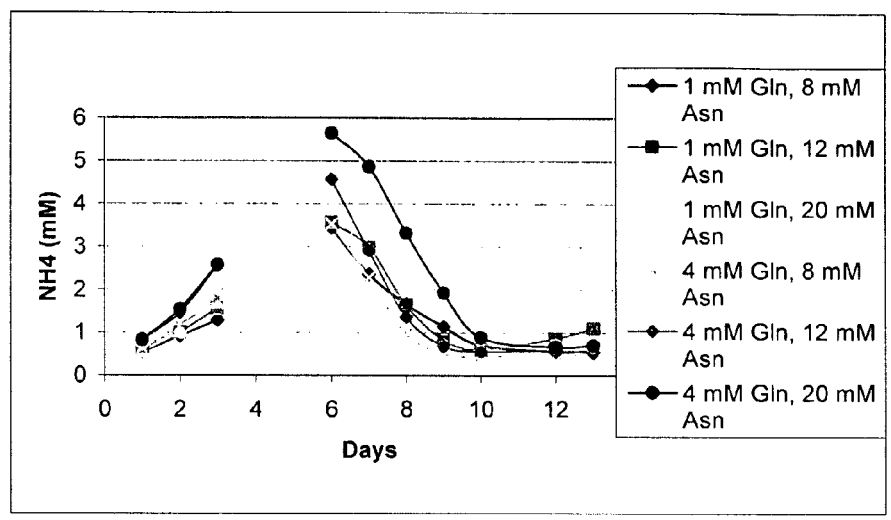
Figure 34. Cell growth of anti-GDF-8 cells in modified Medium 9 containing various levels of glutamine and asparagine.
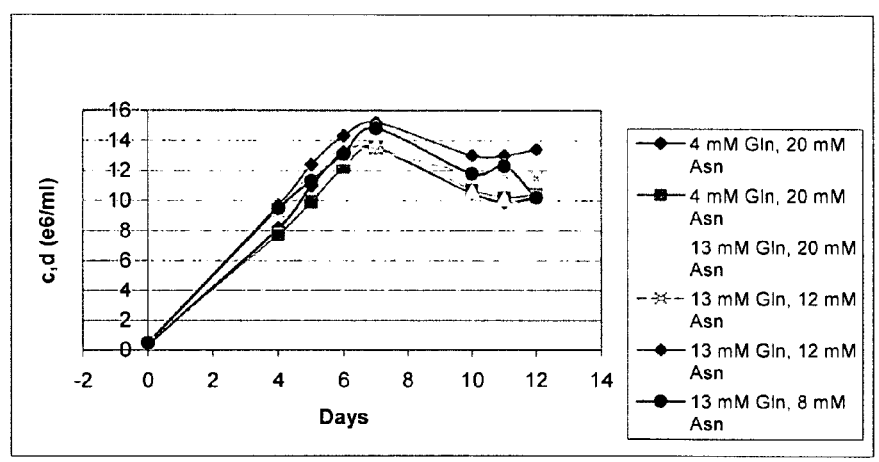

Figure 35. Cell viability of anti-GDF-8 cells in modified Medium 9 containing various levels of glutamine and asparagine.
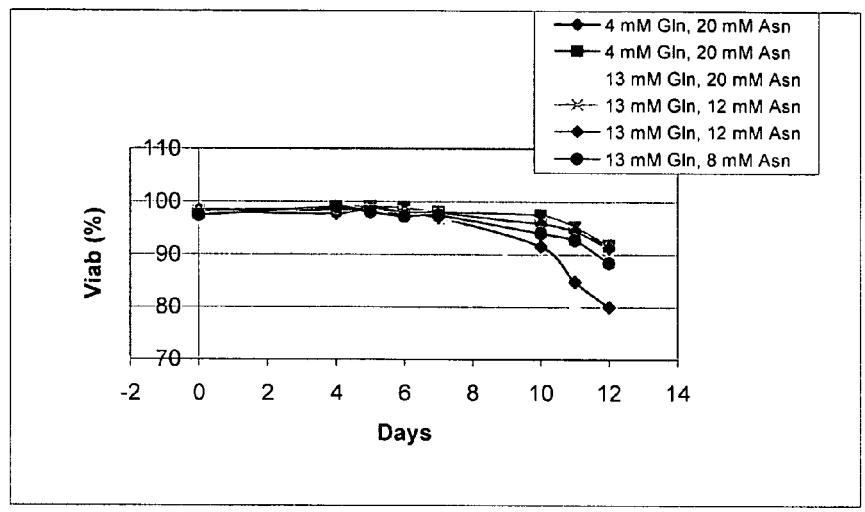
Figure 36. Lactate levels of anti-GDF-8 cultures in modified Medium 9 containing various levels of glutamine and asparagine.
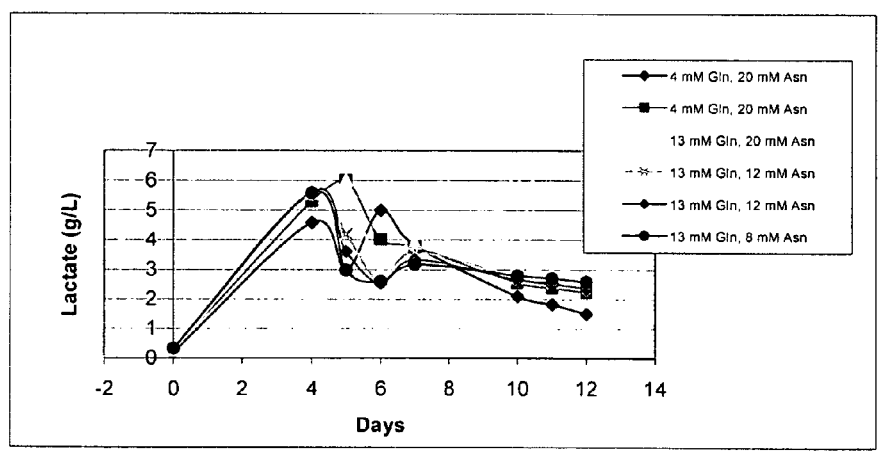

Figure 37. Ammonium levels of anti-GDF-8 cultures in modified Medium 9 containing various levels of glutamine and asparagine.
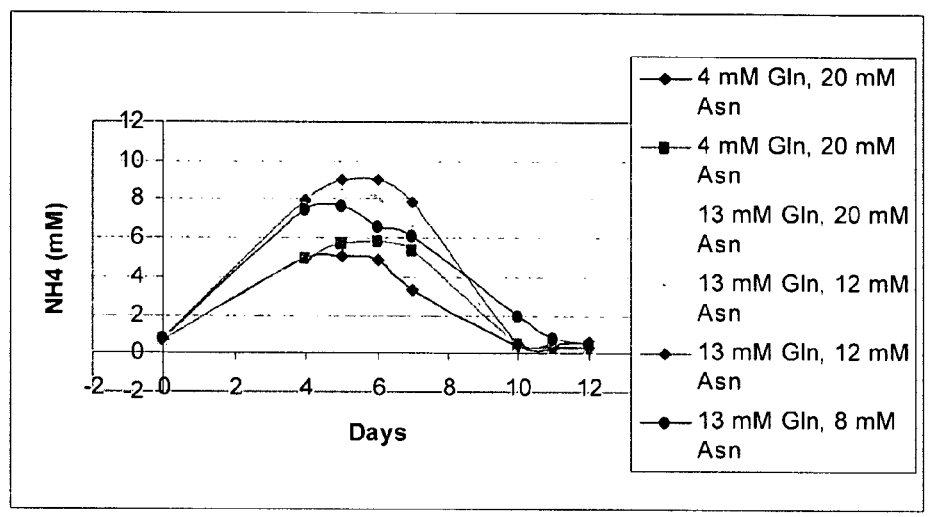
Figure 38. Glutamine levels of anti-GDF-8 cultures in modified Medium 9 containing various levels of glutamine and asparagine.
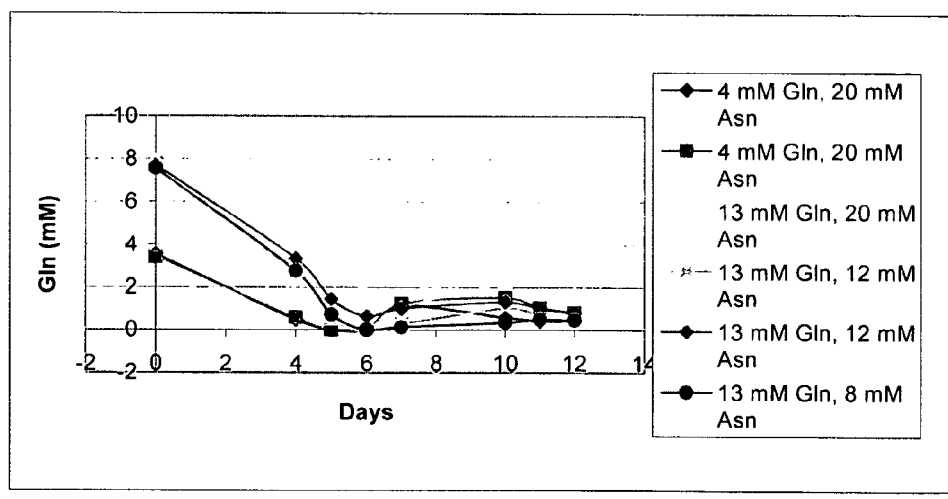

Figure 39. Anti-GDF-8 titer in modified Medium 9 containing various levels of glutamine and asparagine.
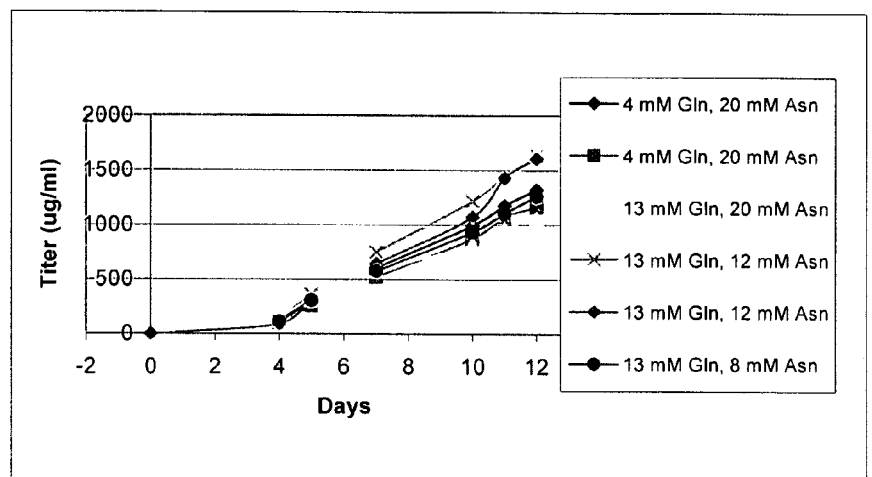
Figure 40. Osmolarity of anti-GDF-8 cultures in modified Medium 9 containing various levels of glutamine and asparagine.
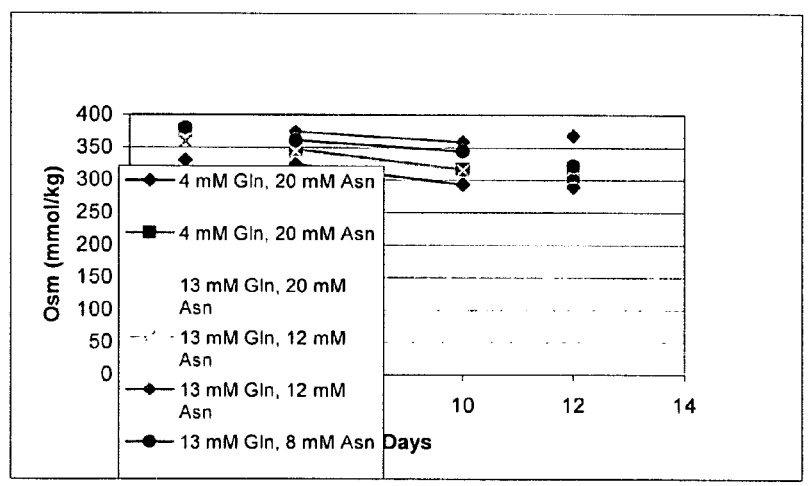

Figure 41. Cell growth of anti-GDF-8 cells in media containing various levels of asparagine and cysteine.
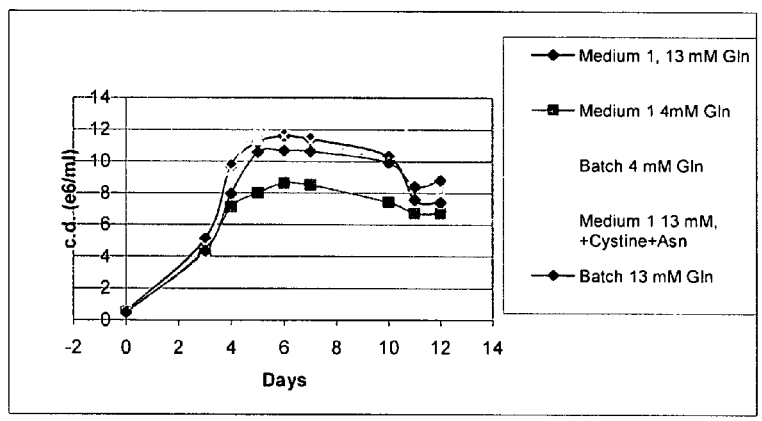
Figure 42. Lactate levels of anti-GDF-8 cultures in media containing various levels of asparagine and cysteine.
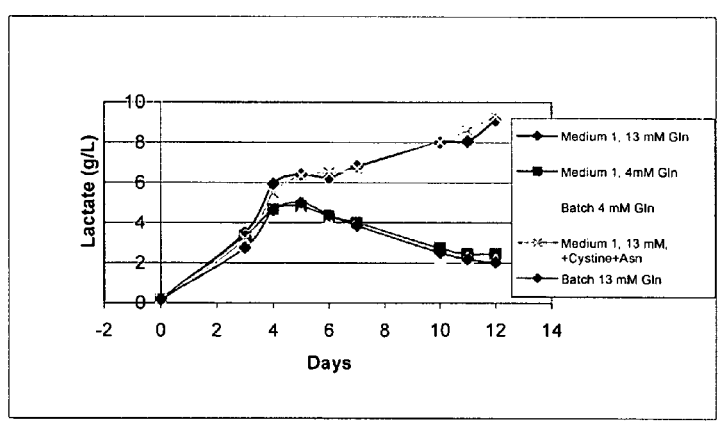

Figure 43. Ammonium levels of anti-GDF-8 cultures in media containing various levels of asparagine and cysteine.
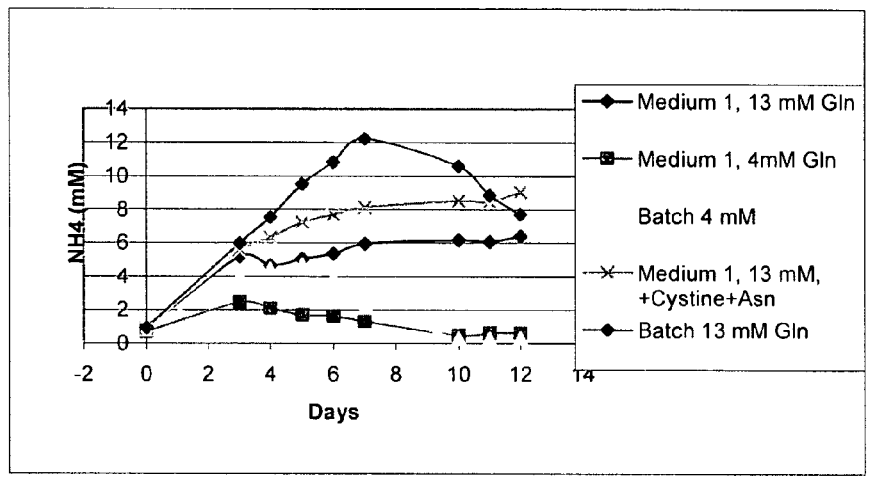
Figure 44. Glutamine levels of anti-GDF-8 cultures in media containing various levels of asparagine and cysteine.
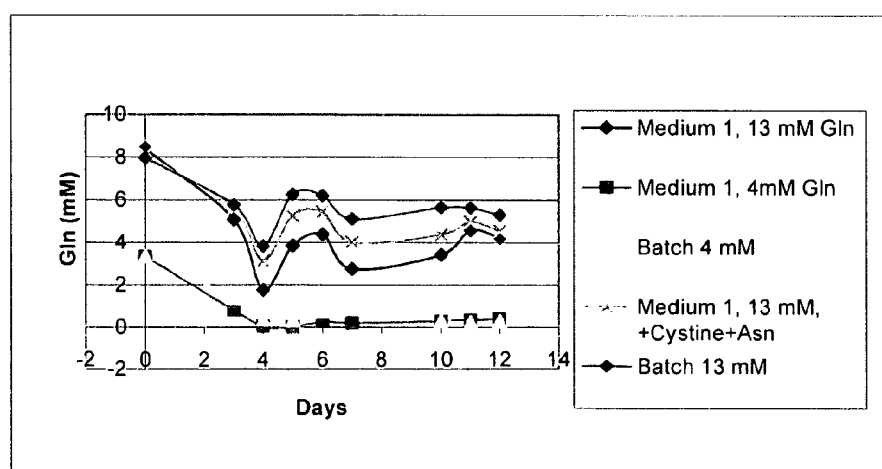

Figure 45. Glutamate levels of anti-GDF-8 cultures in media containing various levels of asparagine and cysteine.
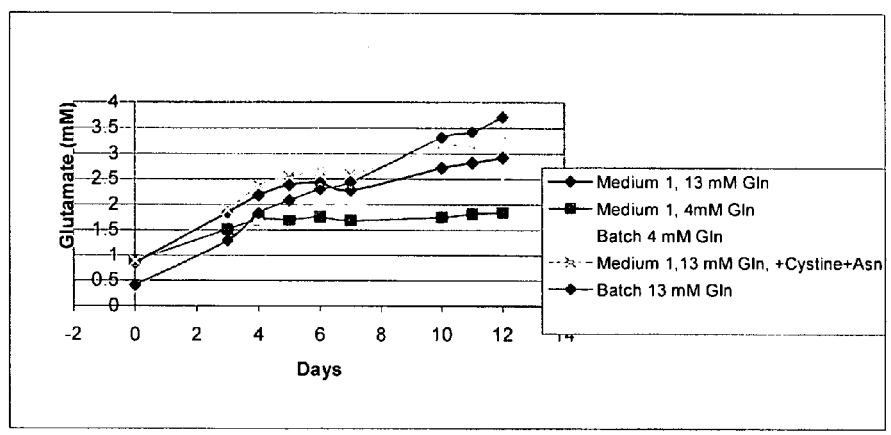
Figure 46. Anti-GDF-8 titer in media containing various levels of asparagine and cysteine.
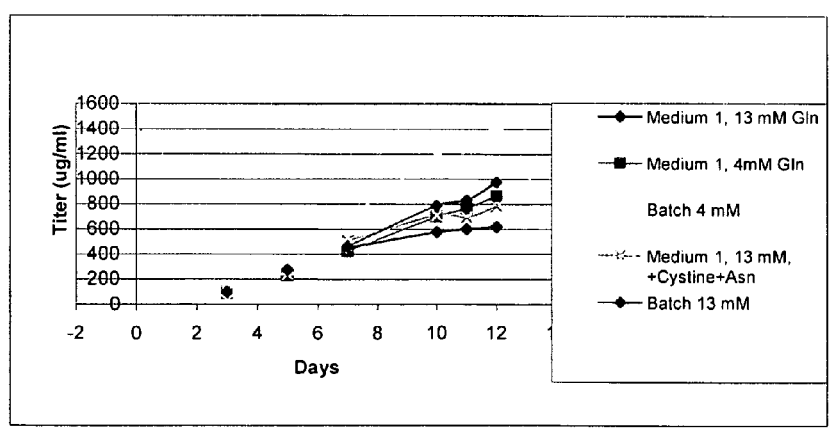

Figure 47. Osmolarity of anti-GDF-8 cultures in media containing various levels of asparagine and cysteine.
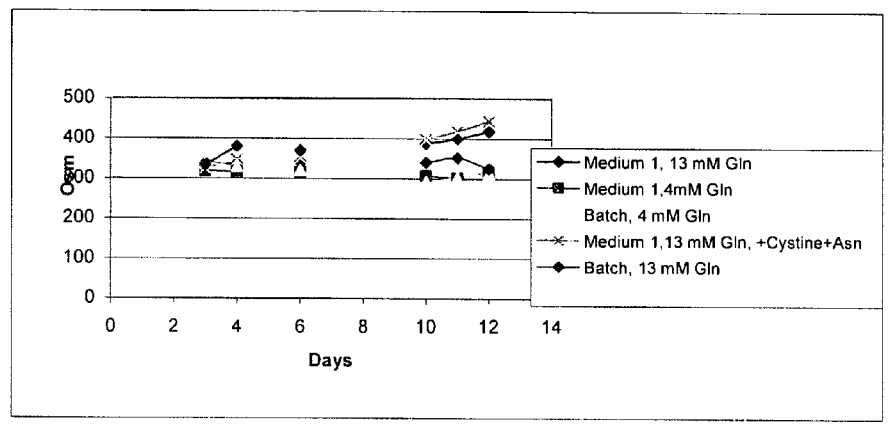
Figure 48. Cell growth of anti-GDF-8 cells in media containing various levels of amino acids and vitamins.
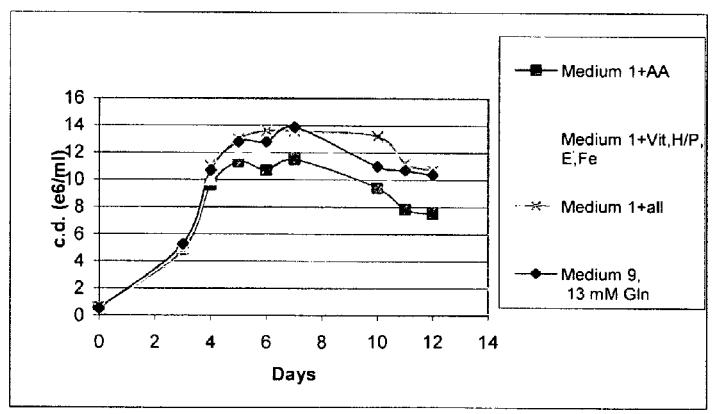

Figure 49. Lactate levels of anti-GDF-8 cultures in media containing various levels of amino acids and vitamins.
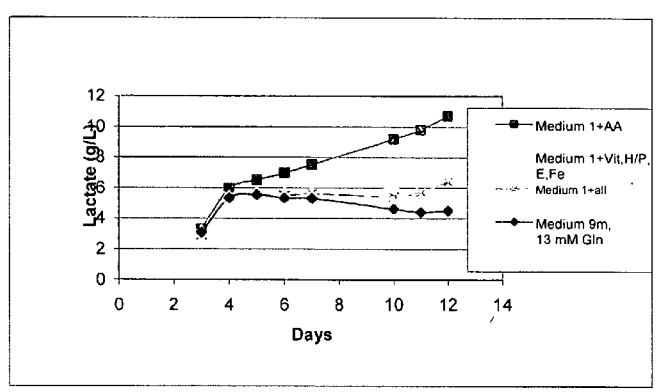
Figure 50. Ammonium levels of anti-GDF-8 cultures in media containing various levels of amino acids and vitamins.
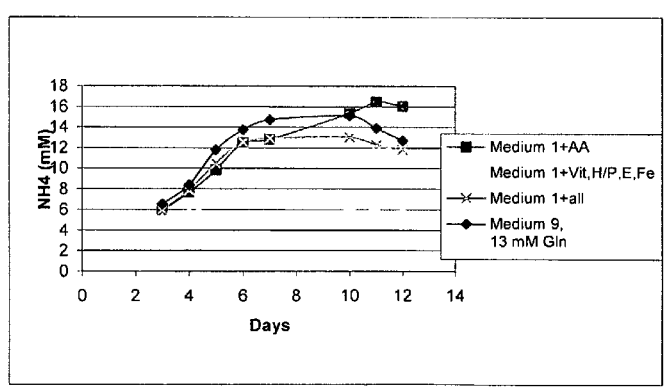

Figure 51. Glutamine levels of anti-GDF-8 cultures in media containing various levels of amino acids and vitamins.
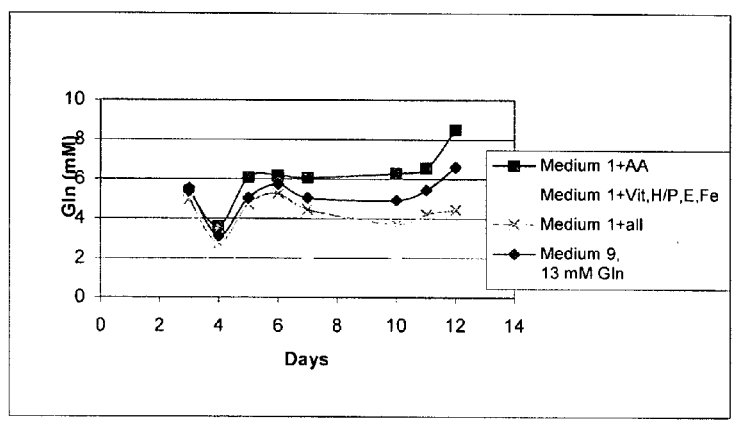
Figure 52. anti-GDF-8 titer in media containing various levels of amino acids and vitamins.
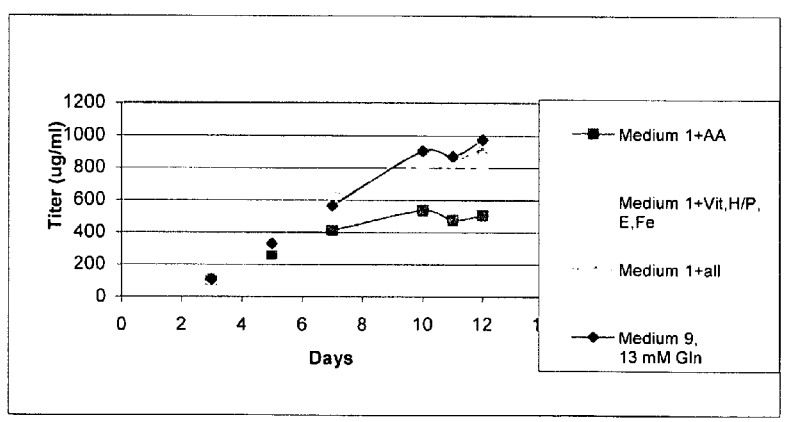

Figure 53. Cell growth of anti-GDF-8 cells in media containing various levels of vitamins, trace elements E and iron.
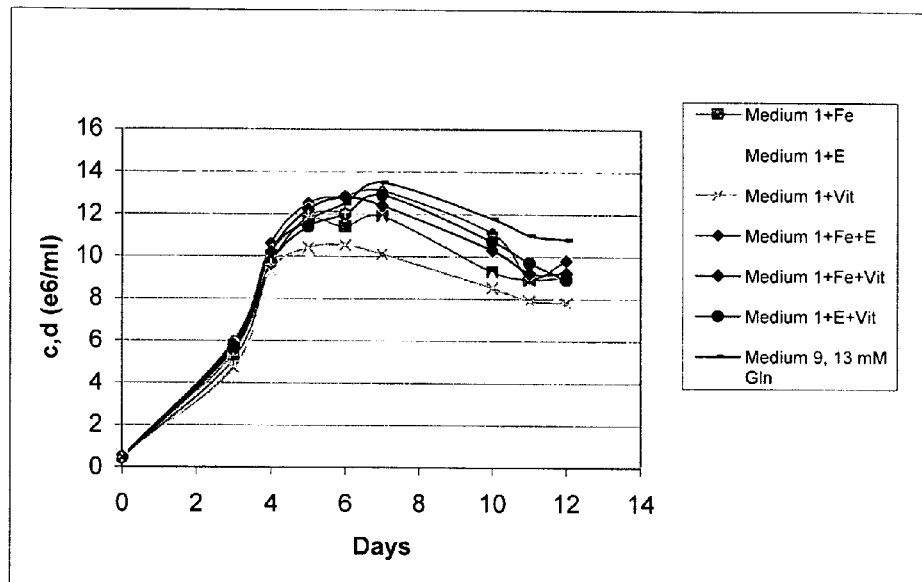
Figure 54. Lactate levels of anti-GDF-8 cultures in media containing various levels of vitamins, trace elements E and iron.
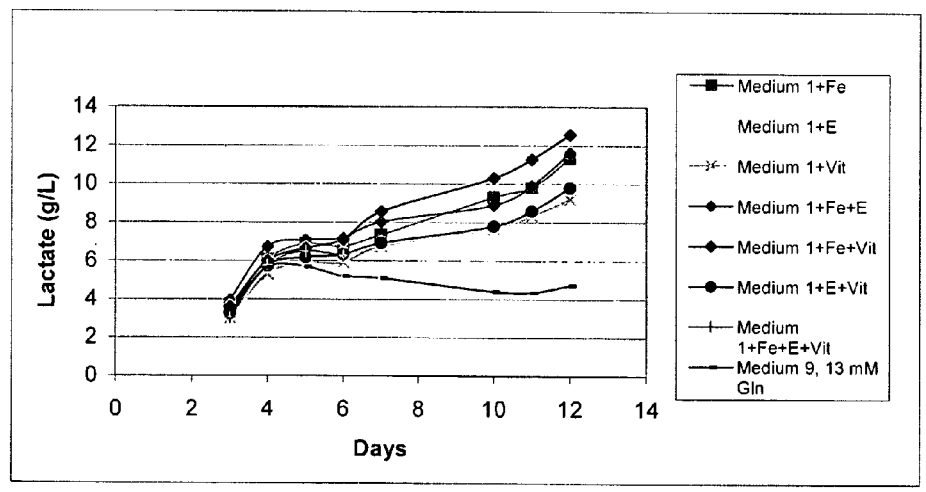

Figure 55. Ammonium levels of anti-GDF-8 cultures in media containing various levels of vitamins, trace elements E and iron.
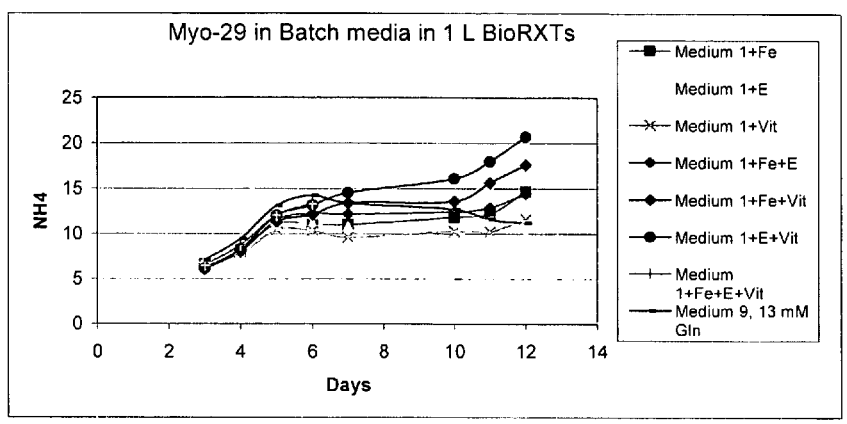
Figure 56. Anti-GDF-8 titer in media containing various levels of vitamins, trace elements E and iron.
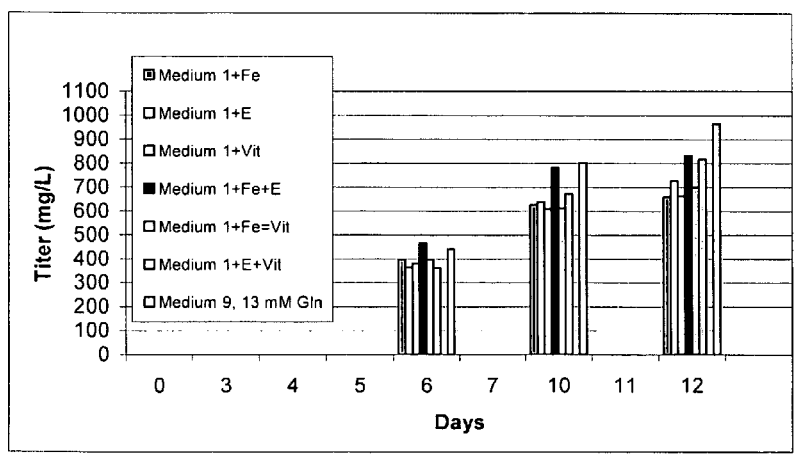

Figure 57. Cell growth of anti-GDF-8 cells in Mediums 1, 3 and 9.
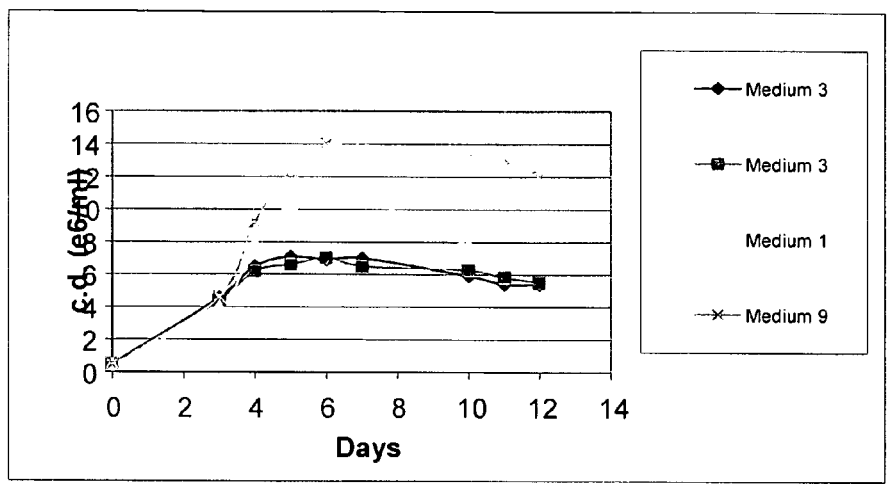
Figure 58. Anti-GDF-8 titer in Mediums 1, 3 and 9.
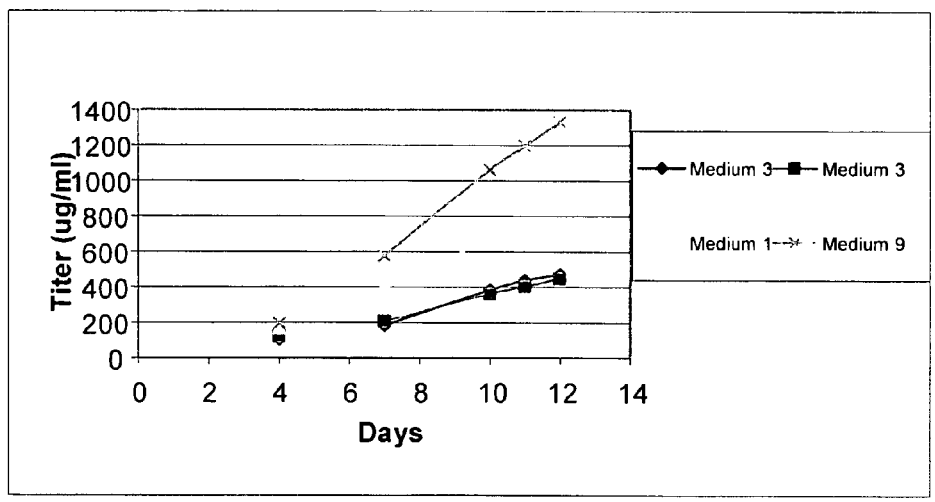

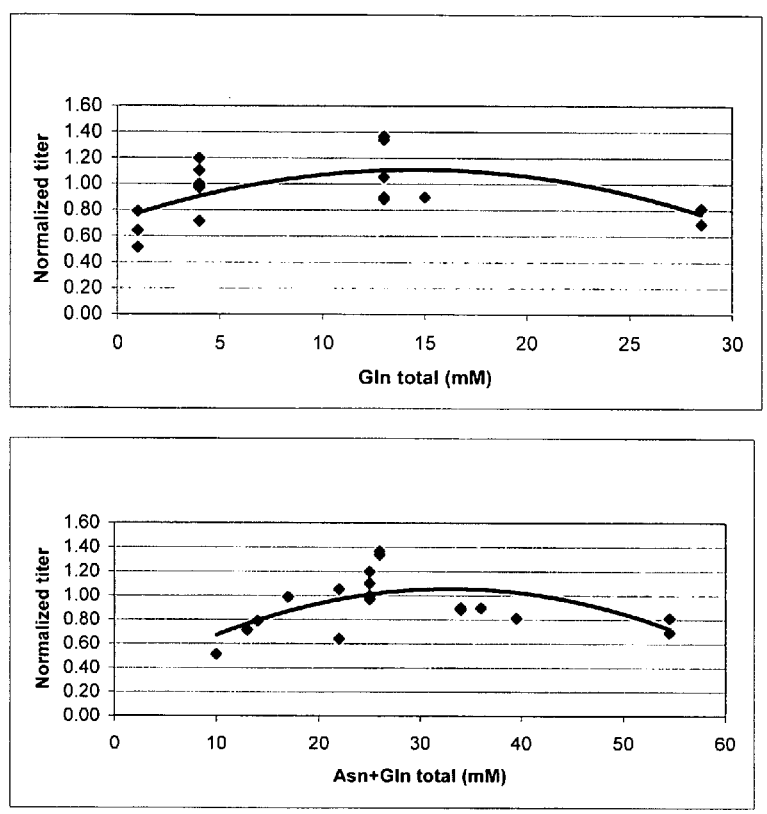
Figure 59. Extrapolated anti-GDF-8 titers for various levels of glutamine alone and total combined glutamine and asparagine.

Figure 60. Growth of anti-ABeta cells under various media conditions tested.
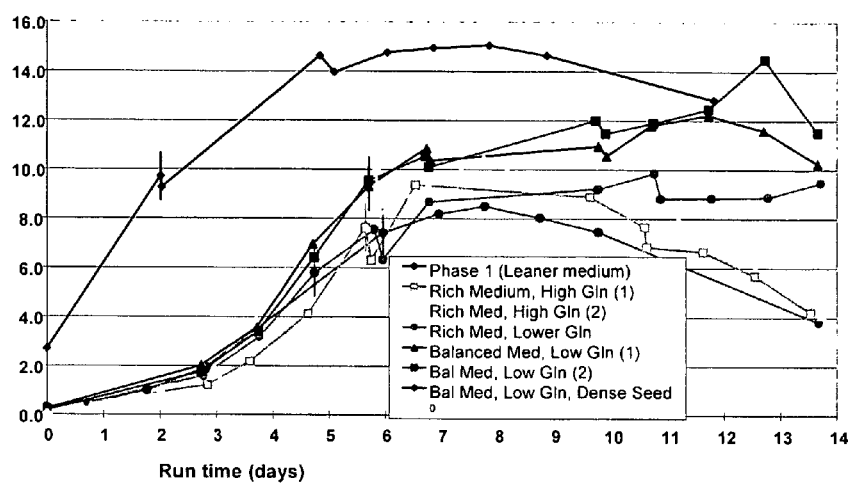
Figure 61. Viability of anti-ABeta cells under various media conditions tested.
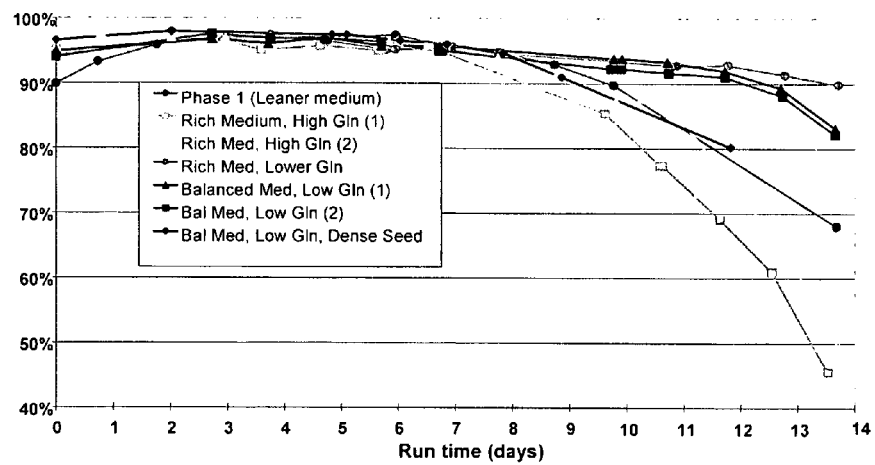

Figure 62. Lactate levels of anti-ABeta cultures under various media conditions tested.
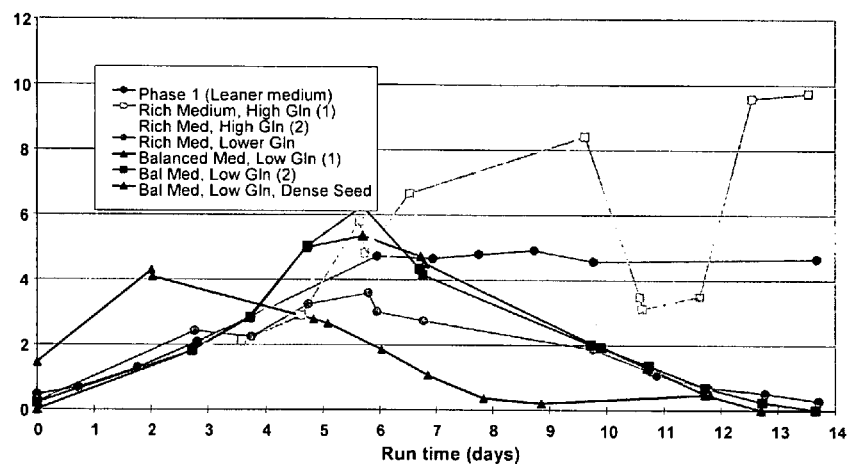
Figure 63. Ammonium levels of anti-ABeta cultures under various media conditions tested.
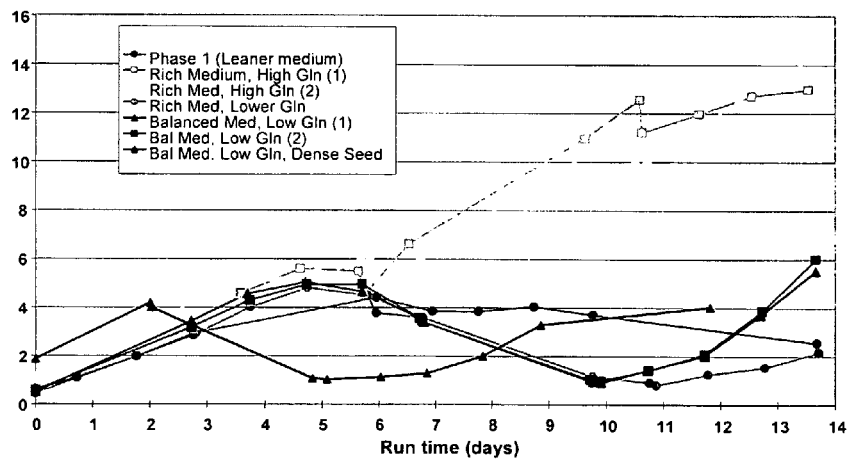

Figure 64. Anti-ABeta titer in various media conditions tested.
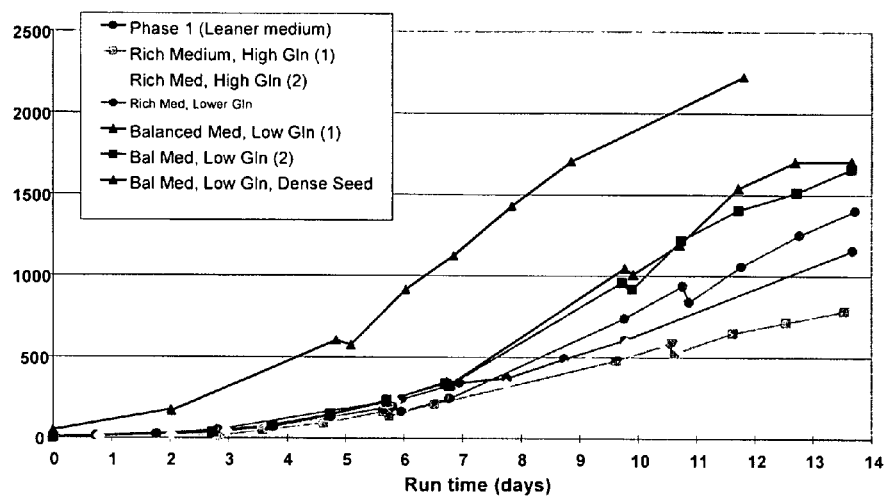
Figure 65. Osmolarity of anti-ABeta cultures under various media conditions tested.
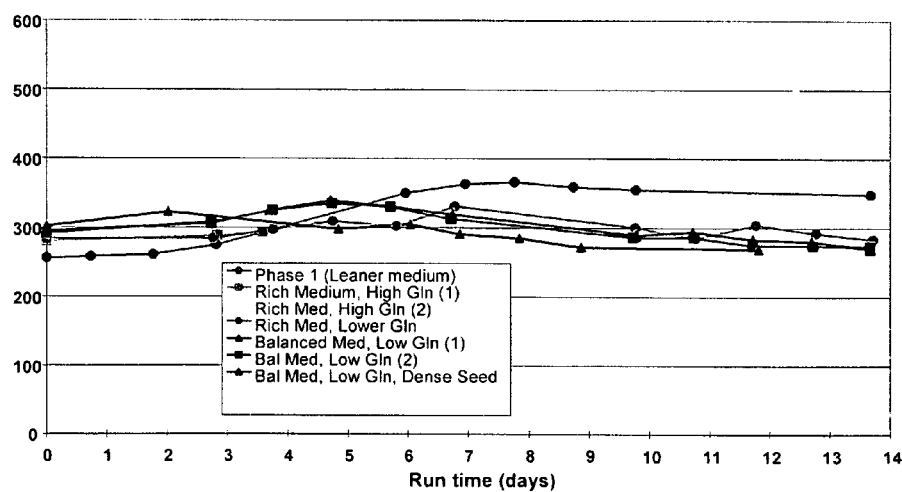

Figure 66. Growth of cells expressing TNFR-Ig under various experimental conditions.
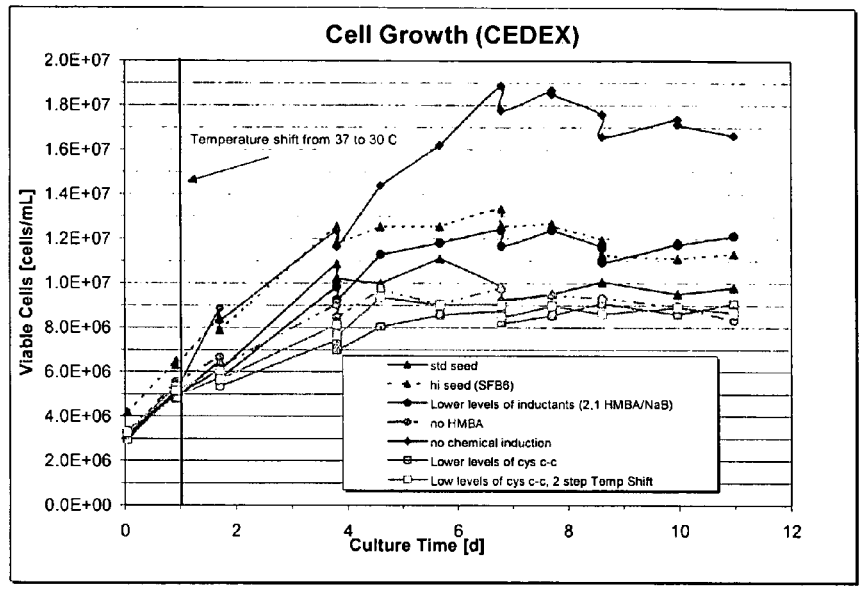
Figure 67. Viability of cells expressing TNFR-Ig under various experimental conditions.
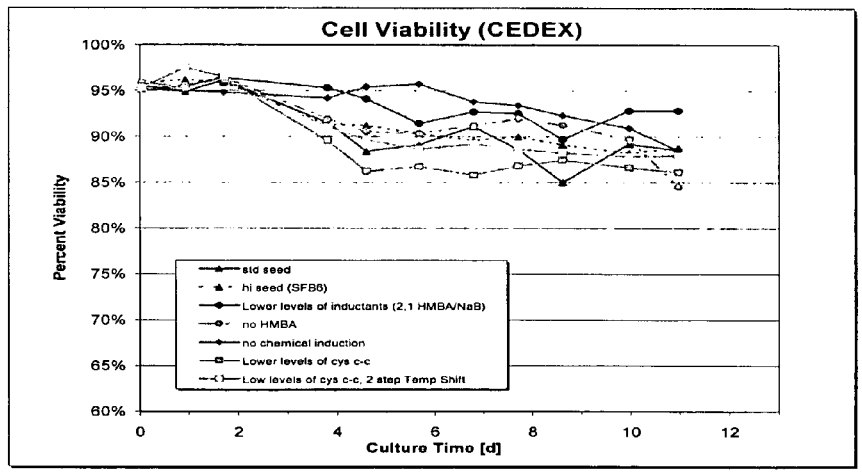

Figure 68. Residual glucose in cultures of cells expressing TNFR-Ig under various experimental conditions.
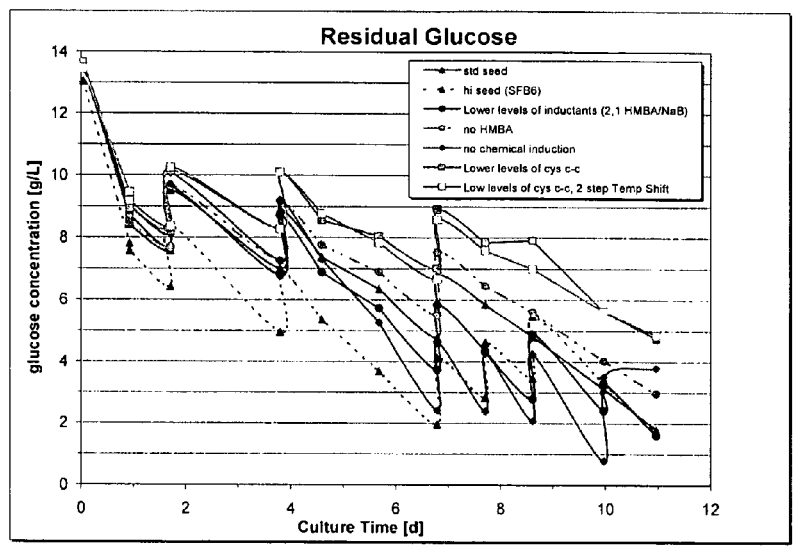
Figure 69. Glutamine levels in cultures of cells expressing TNFR-Ig under various experimental conditions.
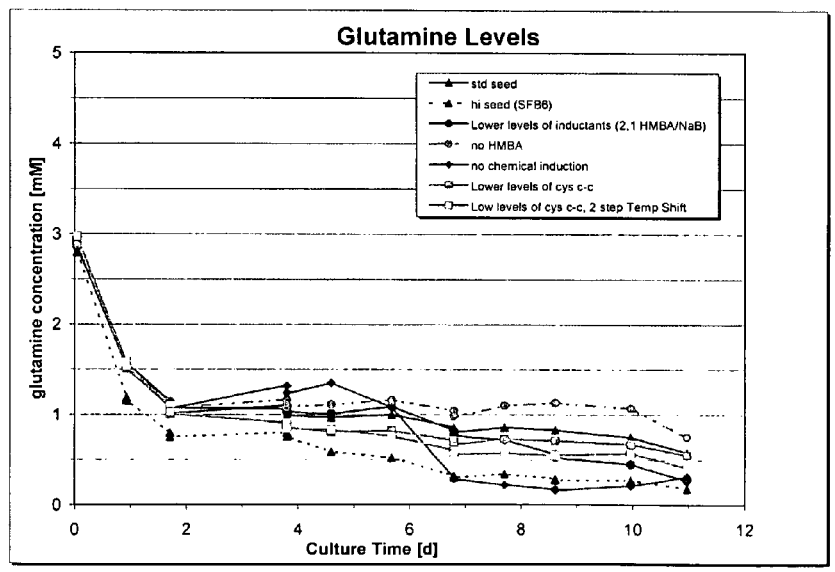

Figure 70. Lactate concentration in cultures of cells expressing TNFR-Ig under various experimental conditions.
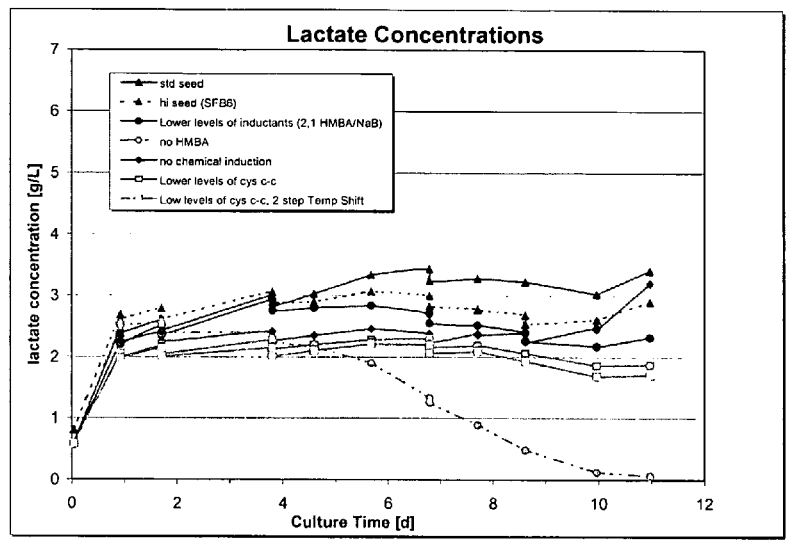
Figure 71. Ammonium levels in cultures of cells expressing TNFR-Ig under various experimental conditions.
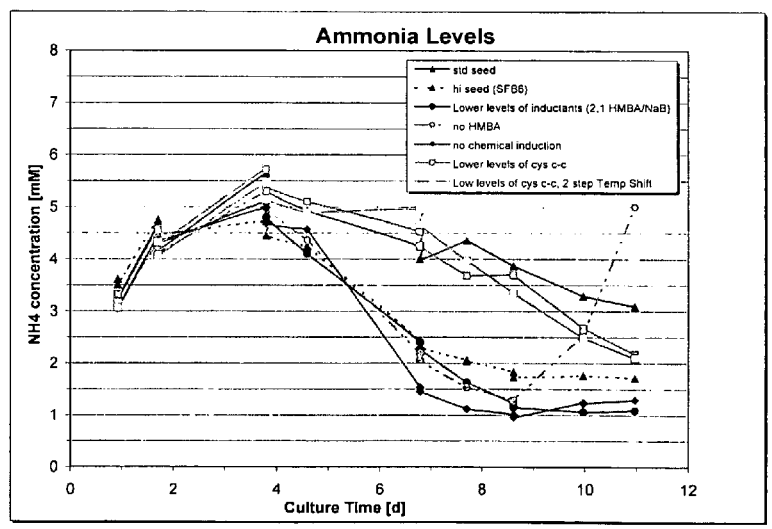

Figure 72. TNFR-Ig relative titer under various experimental conditions.
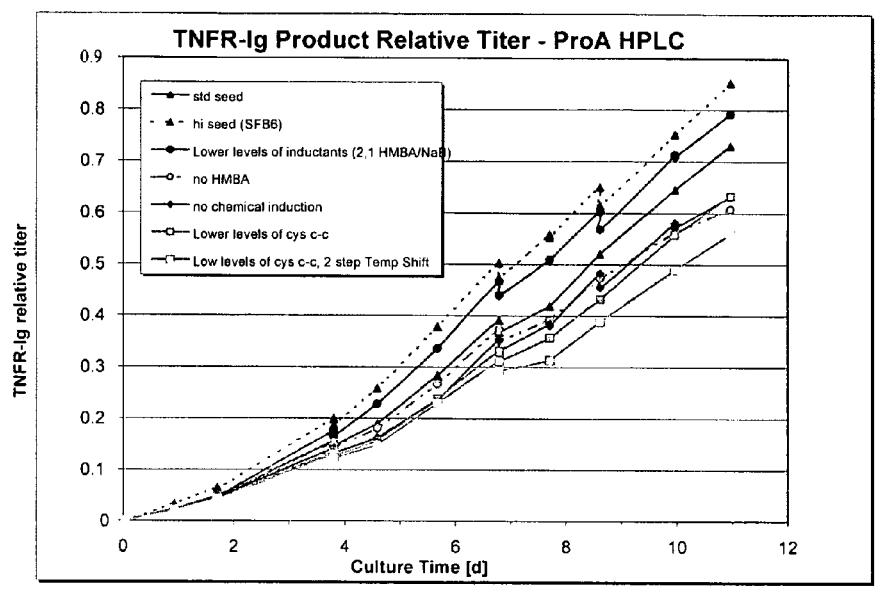
Figure 73. Cell Densities of Anti-GDF-8 Cells Grown in 6000 L and 1 L Bioreactors.
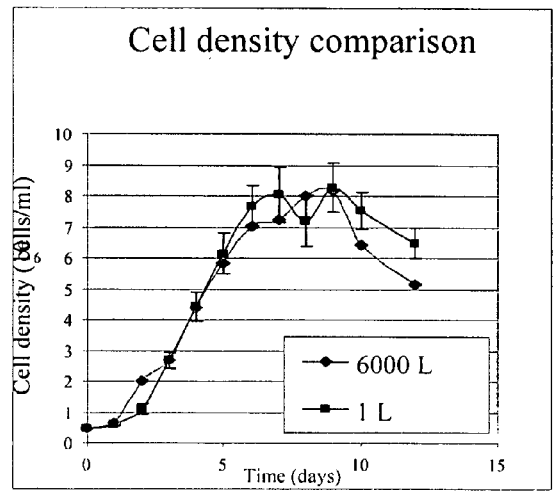

Figure 74. Titers of Anti-GDF-8 Cells Grown in 6000 L and 1 L Bioreactors.
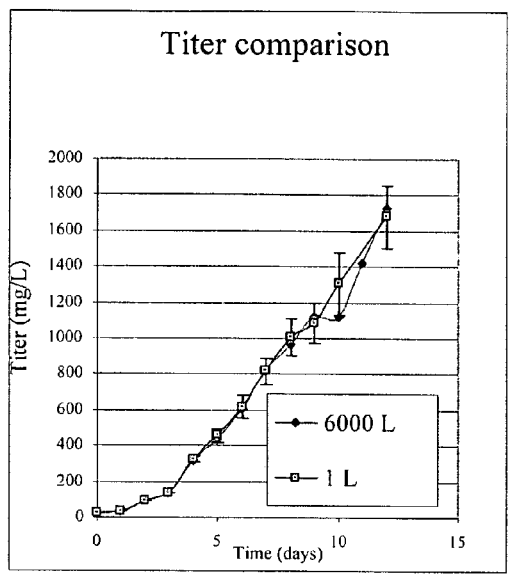
Figure 75. Lactate Levels of Anti-GDF-8 Cells Grown in 6000 L and 1 L Bioreactors.
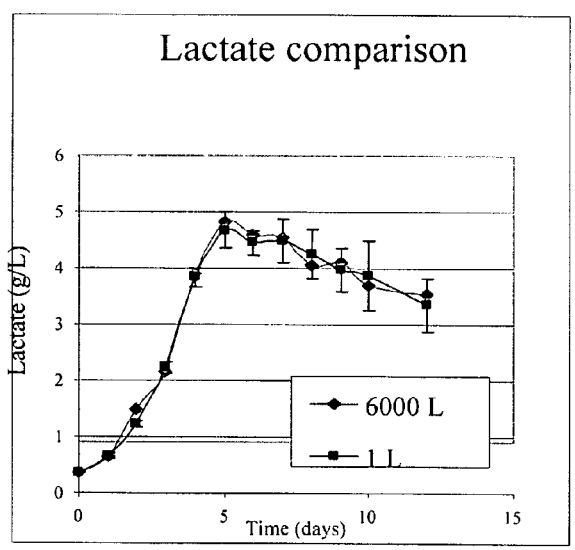

Figure 76. Ammonium Levels of Anti-GDF-8 Cells Grown in 6000 L and 1 L Bioreactors.
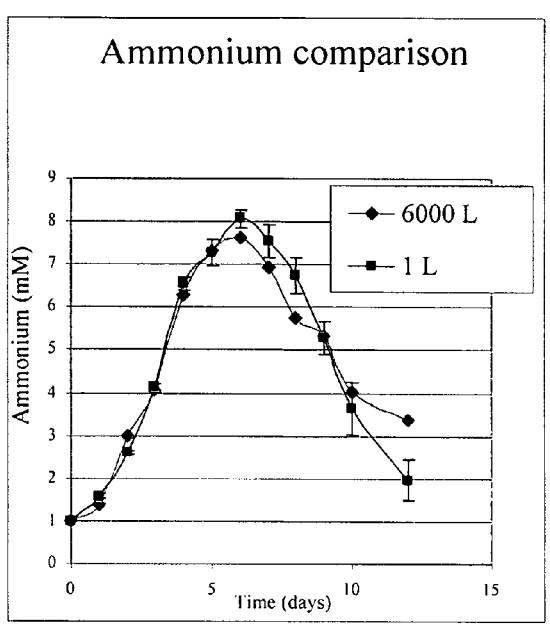

PRODUCTION OF TNFR-IG

RELATED APPLICATION

This application claims priority to Provisional Patent Application No. 60/605,379, filed Aug. 27, 2004, which is incorporated herein by reference in its entirety.

BACKGROUND OF THE INVENTION

Proteins and polypeptides have become increasingly important as therapeutic agents. In most cases, therapeutic proteins and polypeptides are produced in cell culture, from cells that have been engineered and/or selected to produce unusually high levels of the particular protein or polypeptide of interest. Control and optimization of cell culture conditions is critically important for successful commercial production of proteins and polypeptides.

Many proteins and polypeptides produced in cell culture are made in a batch or fed-batch process, in which cells are cultured for a period of time, and then the culture is terminated and the produced protein or polypeptide is isolated. The ultimate amount and quality of protein or polypeptide produced can be dramatically affected by the conditions of the cell culture. For example, traditional batch and fed-batch culture processes often result in production of metabolic waste products that have detrimental effects on cell growth, viability, and production or stability of the protein or polypeptide of interest. While efforts have been made to improve production of proteins and polypeptides in batch and fed-batch culture processes, there remains a need for additional improvements.

Additionally, significant effort has been invested in the development of defined media (i.e., media assembled from known individual components and lacking serum or other animal byproducts) for use in culturing cells, particularly mammalian cells. Cell growth characteristics can be very different in defined media as contrasted with serum-derived media. There is a particular need for the development of improved systems for producing proteins and polypeptides by cell culture in defined media.

SUMMARY OF THE INVENTION

The present invention provides an improved system for large scale production of proteins and/or polypeptides in cell culture. For example, the present invention provides commercial scale (e.g., 500 L or more) culture methods that utilize a medium characterized by one or more of: i) a cumulative amino acid amount per unit volume greater than about 70 mM; ii) a molar cumulative glutamine to cumulative asparagine ratio of less than about 2; iii) a molar cumulative glutamine to cumulative total amino acid ratio of less than about 0.2; iv) a molar cumulative inorganic ion to cumulative total amino acid ratio between about 0.4 to 1; or v) a combined cumulative amount of glutamine and asparagine concentration per unit volume greater than about 16 mM. One of ordinary skill in the art will understand that "cumulative", as used above, refers to the total amount of a particular component or components added over the course of the cell culture, including components added at the beginning of the culture and subsequently added components. In certain preferred embodiments of the invention, it is desirable to minimize "feeds" of the culture over time, so that it is desirable to maximize amounts present initially. Of course, medium components are metabolized during culture so that cultures with the same cumulative amounts of given components will have different absolute levels if those components are added at different times (e.g., all present initially vs. some added by feeds).

According to the present invention, use of such a medium allows high levels of protein production and lessens accumulation of certain undesirable factors such as ammonium and/or lactate.

One of ordinary skill in the art will understand that the media formulations of the present invention encompass both defined and non-defined media. In certain preferred embodiments of the present invention, the culture medium is a defined medium in which the composition of the medium is known and controlled.

In certain preferred embodiments of the present invention, the culture methods include changing the culture from a first set of culture conditions to a second set of culture conditions so that a metabolic shift of the cells is achieved. In some embodiments, this change is performed when the culture has reached about 20-80% of its maximal cell density. In some embodiments, the change involves changing the temperature (or temperature range) at which the culture is maintained. Alternatively or additionally, the present invention provides methods adjusted so that, after reaching a peak, lactate and/or ammonium levels in the culture decrease over time. In other embodiments, the shift involves shifting the pH, osmolarlity or level of chemical inductants, such as alkanoic acids or their salts.

Cell cultures of the present invention may optionally be supplemented with nutrients and/or other medium components including hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source. In certain embodiments of the present invention, it may be beneficial to supplement the media with chemical inductants such as hexamethylene-bis (acetamide) ("HMBA") and sodium butyrate ("NaB"). These optional supplements may be added at the beginning of the culture or may be added at a later point in order to replenish depleted nutrients or for another reason. In general, it is desirable to select the initial medium composition to minimize supplementation in accordance with the present invention.

Various culture conditions may be monitored in accordance with the present invention, including pH, cell density, cell viability, lactate levels, ammonium levels, osmolarity, or titer of the expressed polypeptide or protein.

BRIEF DESCRIPTION OF THE DRAWING

FIG. 1 shows a comparison of Medium 1 and Medium 2 in shake flasks using anti-GDF-8 cells.

FIG. 2 shows cell growth and viability of anti-GDF-8 cells in Medium 1.

FIG. 3 shows cell growth of anti-GDF-8 cell cultures in control and no glutamine feed culture conditions.

FIG. 4 shows cell viability of anti-GDF-8 cell cultures in control and no glutamine feed culture conditions.

FIG. 5 shows ammonium levels of anti-GDF-8 cell cultures in control and no glutamine feed culture conditions.

FIG. 6 shows lactate levels of anti-GDF-8 cell cultures in control and no glutamine feed culture conditions.

FIG. 7 shows anti-GDF-8 titer in control and no glutamine feed culture conditions.

FIG. 8 shows cell density of anti-GDF-8 cell cultures in control and glutamine-starved feed culture conditions.

FIG. 9 shows cell viability of anti-GDF-8 cell cultures in control and glutamine-starved feed culture conditions.

FIG. 10 shows ammonium levels of anti-GDF-8 cell cultures in control and glutamine-starved culture conditions.

FIG. 11 shows lactate levels of anti-GDF-8 cell cultures in control and glutamine-starved culture conditions.

FIG. 12 shows anti-GDF-8 titer in control and glutamine-starved culture conditions.

FIG. 13 shows iron dose response of anti-GDF-8 cells in Medium 1 and Medium 2.

FIG. 14 shows cell density of Glutamate and Glutamine fed cultures.

FIG. 15 shows cell viability of Glutamate and Glutamine fed cultures.

FIG. 16 shows anti-Lewis Y titer in Glutamate and Glutamine fed cultures.

FIG. 17 shows lactate levels in Glutamate and Glutamine fed cultures.

FIG. 18 shows ammonium levels in Glutamate and Glutamine fed cultures.

FIG. 19 shows osmolarity of Glutamate and Glutamine fed cultures.

FIG. 20 shows cell density of anti-Lewis Y cells. Each plot is the average of two shake flasks grown using the same conditions.

FIG. 21 shows cell viability of anti-Lewis Y cells. Each plot is the average of two shake flasks grown using the same conditions.

FIG. 22 shows average titer of anti-Lewis Y culture. Each plot is the average of two shake flasks grown using the same conditions.

FIG. 23 shows ammonium levels of anti-Lewis Y cells. Each plot is the average of two shake flasks grown using the same conditions.

FIG. 24 shows an impeller jump used in fed-batch cultures.

FIG. 25 shows cell growth of anti-GDF-8 cells under various experimental conditions.

FIG. 26 shows viability of anti-GDF-8 cells under various experimental conditions.

FIG. 27 shows anti-GDF-8 titer under various experimental conditions.

FIG. 28 shows lactate levels of anti-GDF-8 cultures under various experimental conditions.

FIG. 29 shows ammonium levels of anti-GDF-8 cultures under various experimental conditions.

FIG. 30 shows cell growth of anti-GDF-8 cells under various experimental conditions.

FIG. 31 shows anti-GDF-8 titer under various experimental conditions.

FIG. 32 shows lactate levels of anti-GDF-8 cultures under various experimental conditions.

FIG. 33 shows ammonium levels of anti-GDF-8 cultures under various experimental conditions.

FIG. 34 shows cell growth of anti-GDF-8 cells in modified Medium 9 containing various levels of glutamine and asparagine.

FIG. 35 shows cell viability of anti-GDF-8 cells in modified Medium 9 containing various levels of glutamine and asparagine.

FIG. 36 shows lactate levels of anti-GDF-8 cultures in modified Medium 9 containing various levels of glutamine and asparagine.

FIG. 37 shows ammonium levels of anti-GDF-8 cultures in modified Medium 9 containing various levels of glutamine and asparagine.

FIG. 38 shows glutamine levels of anti-GDF-8 cultures in modified Medium 9 containing various levels of glutamine and asparagine.

FIG. 39 shows anti-GDF-8 titer in modified Medium 9 containing various levels of glutamine and asparagine.

FIG. 40 shows osmolarity of anti-GDF-8 cultures in modified Medium 9 containing various levels of glutamine and asparagine.

FIG. 41 shows cell growth of anti-GDF-8 cells in media containing various levels of asparagine and cysteine.

FIG. 42 shows lactate levels of anti-GDF-8 cultures in media containing various levels of asparagine and cysteine.

FIG. 43 shows ammonium levels of anti-GDF-8 cultures in media containing various levels of asparagine and cysteine.

FIG. 44 shows glutamine levels of anti-GDF-8 cultures in media containing various levels of asparagine and cysteine.

FIG. 45 shows glutamate levels of anti-GDF-8 cultures in media containing various levels of asparagine and cysteine.

FIG. 46 shows anti-GDF-8 titer in media containing various levels of asparagine and cysteine.

FIG. 47 shows osmolarity of anti-GDF-8 cultures in media containing various levels of asparagine and cysteine.

FIG. 48 shows cell growth of anti-GDF-8 cells in media containing various levels of amino acids and vitamins.

FIG. 49 shows lactate levels of anti-GDF-8 cultures in media containing various levels of amino acids and vitamins.

FIG. 50 shows ammonium levels of anti-GDF-8 cultures in media containing various levels of amino acids and vitamins.

FIG. 51 shows glutamine levels of anti-GDF-8 cultures in media containing various levels of amino acids and vitamins.

FIG. 52 shows anti-GDF-8 titer in media containing various levels of amino acids and vitamins.

FIG. 53 shows cell growth of anti-GDF-8 cells in media containing various levels of vitamins, trace elements E and iron.

FIG. 54 shows lactate levels of anti-GDF-8 cultures in media containing various levels of vitamins, trace elements E and iron.

FIG. 55 shows ammonium levels of anti-GDF-8 cultures in media containing various levels of vitamins, trace elements E and iron.

FIG. 56 shows anti-GDF-8 titer in media containing various levels of vitamins, trace elements E and iron.

FIG. 57 shows cell growth of anti-GDF-8 cells in Mediums 1, 3 and 9.

FIG. 58 shows anti-GDF-8 titer in Medium 1, 3 and 9.

FIG. 59 shows extrapolated anti-GDF-8 titers for various levels of glutamine alone and total combined glutamine and asparagine.

FIG. 60 shows cell growth of anti-ABeta cells under various media conditions tested.

FIG. 61 shows cell viability of anti-ABeta cells under various media conditions tested.

FIG. 62 shows lactate levels of anti-ABeta cultures under various media conditions tested.

FIG. 63 shows ammonium levels of anti-ABeta cultures under various media conditions tested.

FIG. 64 shows anti-ABeta titer in various media conditions tested.

FIG. 65 shows osmolarity of anti-ABeta cultures under various media conditions tested.

FIG. 66 shows cell growth of cells expressing TNFR-Ig under various experimental conditions.

FIG. 67 shows viability of cells expressing TNFR-Ig under various experimental conditions.

FIG. 68 shows residual glucose in cultures of cells expressing TNFR-Ig under various experimental conditions.

FIG. 69 shows glutamine levels in cultures of cells expressing TNFR-Ig under various experimental conditions.

FIG. 70 shows lactate concentration in cultures of cells expressing TNFR-Ig under various experimental conditions.

FIG. 71 shows ammonium levels in cultures of cells expressing TNFR-Ig under various experimental conditions.

FIG. 72 shows TNFR-Ig relative titer under various experimental conditions.

FIG. 73 shows cell densities of anti-GDF-8 cells grown in 6000 L and 1 L bioreactors.

FIG. 74 shows titers of anti-GDF-8 cells grown in 6000 L and 1 L bioreactors.

FIG. 75 shows lactate levels of anti-GDF-8 cells grown in 6000 L and 1 L bioreactors.

FIG. 76 shows ammonium levels of anti-GDF-8 cells grown in 6000 L and 1 L bioreactors.

DEFINITIONS

"About", "Approximately": As used herein, the terms "about" and "approximately", as applied to one or more particular cell culture conditions, refer to a range of values that are similar to the stated reference value for that culture condition or conditions. In certain embodiments, the term "about" refers to a range of values that fall within 25, 20, 19, 18, 17, 16, 15, 14, 13, 12, 11, 10, 9, 8, 7, 6, 5, 4, 3, 2, 1 percent or less of the stated reference value for that culture condition or conditions.

"Amino acid": The term "amino acid" as used herein refers to any of the twenty naturally occurring amino acids that are normally used in the formation of polypeptides, or analogs or derivatives of those amino acids. Amino acids of the present invention are provided in medium to cell cultures. The amino acids provided in the medium may be provided as salts or in hydrate form.

"Antibody": The term "antibody" as used herein refers to an immunoglobulin molecule or an immunologically active portion of an immunoglobulin molecule, such as a Fab or F(ab')$_2$ fragment, that contains one or more antigen binding sites which specifically bind (immunoreact with) an antigen. The terms "monoclonal antibodies" and "monoclonal antibody composition", as used herein, refer to a clonal population of antibody molecules that contain only one species of an antigen binding site capable of immunoreacting with a particular epitope of an antigen, whereas the terms "polyclonal antibodies" and "polyclonal antibody composition" refer to a population of antibody molecules that contain multiple species of antigen binding sites capable of interacting with a particular antigen. The definition of monoclonal antibodies includes both clonal molecules derived by traditional technologies as well as molecules of defined sequence derived by manipulation or mutation of specific residues, for example, humanized antibodies.

"Batch culture": The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

"Bioreactor": The term "bioreactor" as used herein refers to any vessel used for the growth of a mammalian cell culture. The bioreactor can be of any size so long as it is useful for the culturing of mammalian cells. Typically, the bioreactor will be at least 1 liter and may be 10, 100, 250, 500, 1000, 2500, 5000, 8000, 10,000, 12,0000 liters or more, or any volume in between. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and may be 1000, 2500, 5000, 8000, 10,000, 12,0000 liters or more, or any volume in between. One of ordinary skill in the art will be aware of and will be able to choose suitable bioreactors for use in practicing the present invention.

"Cell density": The term "cell density" as used herein refers to that number of cells present in a given volume of medium.

"Cell viability": The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

"Culture", "Cell culture" and "Mammalian cell culture": These terms as used herein refer to a mammalian cell population that is suspended in a medium (see definition of "medium" below) under conditions suitable to survival and/or growth of the cell population. As will be clear to those of ordinary skill in the art, these terms as used herein may refer to the combination comprising the mammalian cell population and the medium in which the population is suspended.

"Fed-batch culture": The term "fed-batch culture" as used herein refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

"Fragment": The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retained is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

"Gene": The term "gene" as used herein refers to any nucleotide sequence, DNA or RNA, at least some portion of which encodes a discrete final product, typically, but not limited to, a polypeptide, which functions in some aspect of cellular metabolism or development. The term is not meant to refer only to the coding sequence that encodes the polypeptide or other discrete final product, but may also encompass regions preceding and following the coding sequence that modulate the basal level of expression (see definition of "genetic control element" below), as well as any intervening sequences ("introns") between individual coding segments ("exons").

"Genetic control element": The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

"Hybridoma": The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., Nature, 537:3053 (1983)).

"Integrated Viable Cell Density": The term "integrated viable cell density" as used herein refers to the average density of viable cells over the course of the culture multiplied by the amount of time the culture has run. Assuming the amount of polypeptide and/or protein produced is proportional to the number of viable cells present over the course of the culture, integrated viable cell density is a useful tool for estimating the amount of polypeptide and/or protein produced over the course of the culture.

"Medium", "Cell culture medium", "Culture medium": These terms as used herein refer to a solution containing nutrients which nourish growing mammalian cells. Typically, these solutions provide essential and non-essential amino acids, vitamins, energy sources, lipids, and trace elements required by the cell for minimal growth and/or survival. The solution may also contain components that enhance growth and/or survival above the minimal rate, including hormones and growth factors. The solution is preferably formulated to a pH and salt concentration optimal for cell survival and proliferation. The medium may also be a "defined media"—a serum-free media that contains no proteins, hydrolysates or components of unknown composition. Defined media are free of animal-derived components and all components have a known chemical structure.

"Metabolic waste product": The term "metabolic waste product" as used herein refers to compounds produced by the cell culture as a result of normal or non-normal metabolic processes that are in some way detrimental to the cell culture, particularly in relation to the expression or activity of a desired recombinant polypeptide or protein. For example, the metabolic waste products may be detrimental to the growth or viability of the cell culture, may decrease the amount of recombinant polypeptide or protein produced, may alter the folding, stability, glycoslyation or other post-translational modification of the expressed polypeptide or protein, or may be detrimental to the cells and/or expression or activity of the recombinant polypeptide or protein in any number of other ways. Exemplary metabolic waste products include lactate, which is produced as a result of glucose metabolism, and ammonium, which is produced as a result of glutamine metabolism. One goal of the present invention is to slow production of, reduce or even eliminate metabolic waste products in mammalian cell cultures.

"Osmolarity" and "Osmolality": "Osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of solution (1 mOsm/kg $H_2O$ at 38° C. is equivalent to an osmotic pressure of 19 mm Hg). "Osmolarity," by contrast, refers to the number of solute particles dissolved in 1 liter of solution. When used herein, the abbreviation "mOsm" means "milliosmoles/kg solution".

"Perfusion culture": The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

"Polypeptide": The term "polypeptide" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond.

"Protein": The term "protein" as used herein refers to one or more polypeptides that function as a discrete unit. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

"Recombinantly expressed polypeptide" and "Recombinant polypeptide": These terms as used herein refer to a polypeptide expressed from a mammalian host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide contain amino acid sequences that are identical or similar to polypeptides normally expressed in the mammalian host cell, while other portions are foreign to the host cell.

"Seeding": The term "seeding" as used herein refers to the process of providing a cell culture to a bioreactor or another vessel. The cells may have been propagated previously in another bioreactor or vessel. Alternatively, the cells may have been frozen and thawed immediately prior to providing them to the bioreactor or vessel. The term refers to any number of cells, including a single cell.

"Titer": The term "titer" as used herein refers to the total amount of recombinantly expressed polypeptide or protein produced by a mammalian cell culture divided by a given amount of medium volume. Titer is typically expressed in units of milligrams of polypeptide or protein per milliliter of medium.

DETAILED DESCRIPTION OF CERTAIN PREFERRED EMBODIMENTS

The present invention provides improved systems for the production of proteins and/or polypeptides by cell culture. In particular, the invention provides systems that minimize production of one or more metabolic products detrimental to cell growth, viability, and/or protein production or quality. In a preferred embodiment of the present invention, the cell culture is a batch or fed-batch culture. Other certain preferred embodiments of the invention are discussed in detail below. Those of ordinary skill in the art will understand, however, that various modifications to these preferred embodiments are within the scope of the appended claims. It is the claims and equivalents thereof that define the scope of the present invention, which is not and should not be limited to or by this description of certain preferred embodiments.

Polypeptides

Any polypeptide that is expressible in a host cell may be produced in accordance with the present invention. The polypeptide may be expressed from a gene that is endogenous to the host cell, or from a gene that is introduced into the host cell through genetic engineering. The polypeptide may be one that occurs in nature, or may alternatively have a sequence that was engineered or selected by the hand of man. An engineered polypeptide may be assembled from other polypeptide segments that individually occur in nature, or may include one or more segments that are not naturally occurring.

Polypeptides that may desirably be expressed in accordance with the present invention will often be selected on the basis of an interesting biological or chemical activity. For example, the present invention may be employed to express any pharmaceutically or commercially relevant enzyme, receptor, antibody, hormone, regulatory factor, antigen, binding agent, etc.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell may be used in accordance with the present invention. In a preferred embodiment, the antibody to be expressed is a monoclonal antibody.

In another preferred embodiment, the monoclonal antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci.* U.S.A. 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

In another preferred embodiment, the monoclonal antibody is a human antibody derived, e.g., through the use of ribosome-display or phage-display libraries (see, e.g., Winter et al., U.S. Pat. No. 6,291,159 and Kawasaki, U.S. Pat. No. 5,658,754) or the use of xenographic species in which the native antibody genes are inactivated and functionally replaced with human antibody genes, while leaving intact the other components of the native immune system (see, e.g., Kucherlapati et al., U.S. Pat. No. 6,657,103).

In another preferred embodiment, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a non-human species that confer a desired antigen specificity or affinity. Such altered immunoglobulin molecules can be made by any of several techniques known in the art, (e.g., Teng et al., *Proc. Natl. Acad. Sci.* USA., 80, 7308-7312 (1983); Kozbor et al., *Immunology Today*, 4, 7279 (1983); Olsson et al., *Meth. Enzymol.*, 92, 3-16 (1982)), and are preferably made according to the teachings of PCT Publication WO92/06193 or EP 0239400, all of which are incorporated herein by reference). Humanized antibodies can be commercially produced by, for example, Scotgen Limited, 2 Holly Road, Twickenham, Middlesex, Great Britain. For further reference, see Jones et al., *Nature* 321:522-525 (1986); Riechmann et al., *Nature* 332:323-329 (1988); and Presta, *Curr. Op. Struct. Biol.* 2:593-596 (1992), all of which are incorporated herein by reference.

In another preferred embodiment, the monoclonal, chimeric, or humanized antibodies described above may contain amino acid residues that do not naturally occur in any antibody in any species in nature. These foreign residues can be utilized, for example, to confer novel or modified specificity, affinity or effector function on the monoclonal, chimeric or humanized antibody. In another preferred embodiment, the antibodies described above may be conjugated to drugs for systemic pharmacotherapy, such as toxins, low-molecular-weight cytotoxic drugs, biological response modifiers, and radionuclides (see e.g., Kunz et al., *Calicheamicin derivative-carrier conjugates*, US20040082764 A1).

In one embodiment, the antibody is an antibody that specifically binds to the Aβ fragment of amyloid precursor protein or to other components of an amyloid plaque, and is useful in combating the accumulation of amyloid plaques in the brain which characterize Alzheimer's disease. (See, e.g., U.S. Provisional Application 60/636,684.)

In another embodiment, antibodies of the present invention are directed against cell surface antigens expressed on target cells and/or tissues in proliferative disorders such as cancer. In one embodiment, the antibody is an IgG1 anti-Lewis Y antibody. Lewis Y is a carbohydrate antigen with the structure Fucα1→2Galβ1→4[Fucα1→3]GlcNacβ1→3R (Abe et al. (1983) J. Biol. Chem., 258 11793-11797). Lewis Y antigen is expressed on the surface of 60% to 90% of human epithelial tumors (including those of the breast, colon, lung, and prostate), at least 40% of which overexpress this antigen, and has limited expression in normal tissues.

In order to target Ley and effectively target a tumor, an antibody with exclusive specificity to the antigen is ideally required. Thus, preferably, the anti-Lewis Y antibodies of the present invention do not cross-react with the type 1 structures (i.e., the lacto-series of blood groups (Lea and Leb)) and, preferably, do not bind other type 2 epitopes (i.e., neolacto-structure) like Lex and H-type 2 structures. An example of a preferred anti-Lewis Y antibody is designated hu3S193 (see U.S. Pat. Nos. 6,310,185; 6,518,415; 5,874,060, incorporated herein in their entirety). The humanized antibody hu3S193 (Attia, M. A., et al. 1787-1800) was generated by CDR-grafting from 3S193, which is a murine monoclonal antibody raised against adenocarcinoma cell with exceptional specificity for Ley (Kitamura, K., 12957-12961). Hu3S 193 not only retains the specificity of 3S193 for Ley but has also gained in the capability to mediate complement dependent cytotoxicity (hereinafter referred to as CDC) and antibody dependent cellular cytotoxicity (hereinafter referred to as ADCC) (Attia, M. A., et al. 1787-1800). This antibody targets Ley expressing xenografts in nude mice as demonstrated by biodistribution studies with hu3S 193 labeled with 125I, 111In, or 18F, as well as other radiolabels that require a chelating agent, such as 111In, 99mTc, or 90Y (Clark, et al. 4804-4811).

In another embodiment, the antibody is one of the human anti-GDF-8 antibodies termed Myo29, Myo28, and Myo22, and antibodies and antigen-binding fragments derived therefrom. These antibodies are capable of binding mature GDF-8 with high affinity, inhibit GDF-8 activity in vitro and in vivo as demonstrated, for example, by inhibition of ActRIIB binding and reporter gene assays, and may inhibit GDF-8 activity associated with negative regulation of skeletal muscle mass and bone density. See, e.g., Veldman, et al, U.S. Patent Application No. 20040142382.

Receptors

Another class of polypeptides that have been shown to be effective as pharmaceutical and/or commercial agents includes receptors. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. In one embodiment, the receptors of interest are modified so as to remove the transmembrane and/or intracellular domain(s), in place of which there may optionally be attached an Ig-domain. In a preferred embodiment, receptors to be produced in accordance with the present invention are receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74 (1995), incorporated herein be reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2 (VEGFR-2)), fms-like tyrosine kinase-1 (Flt-1) (DeVries et al. Science 255;989-991, 1992; Shibuya et al., Oncogene 5:519-524, 1990), sometimes referred to as vascular endothelial cell growth factor receptor 1 (VEGFR-1), neuropilin-1, endoglin, endosialin, and Ax1. Those of ordinary skill in the art will be aware of other receptors that can preferably be expressed in accordance with the present invention.

In a particularly preferred embodiment, tumor necrosis factor inhibitors, in the form of tumor necrosis factor alpha and beta receptors (TNFR-1; EP 417,563 published Mar. 20, 1991; and TNFR-2, EP 417,014 published Mar. 20, 1991) are expressed in accordance with the present invention (for review, see Naismith and Sprang, *J Inflamm.* 47(1-2):1-7 (1995-96), incorporated herein by reference). According to one embodiment, the tumor necrosis factor inhibitor comprises a soluble TNF receptor and preferably a TNFR-Ig. In one embodiment, the preferred TNF inhibitors of the present invention are soluble forms of TNFRI and TNFRII, as well as soluble TNF binding proteins, in another embodiment, the TNFR-Ig fusion is a TNFR:Fc, a term which as used herein refers to "etanercept," which is a dimer of two molecules of the extracellular portion of the p75 TNF-.alpha. receptor, each molecule consisting of a 235 amino acid Fc portion of human IgG.sub.1.

Growth Factors and Other Signaling Molecules

Another class of polypeptides that have been shown to be effective as pharmaceutical and/or commercial agents includes growth factors and other signaling molecules. Growth factors are typically glycoproteins that are secreted by cells and bind to and activate receptors on other cells, initiating a metabolic or developmental change in the receptor cell. In one embodiment, the protein of interest is an ActRIIB fusion polypeptide comprising the extracellular domain of the ActRIIB receptor and the Fc portion of an antibody (see, e.g., Wolfman, et al., *ActRIIB fusion polypeptides and uses therefor*, US2004/0223966 A1). In another embodiment, the growth factor may be a modified GDF-8 propeptide (see., e.g., Wolfman, et al., *Modified and stabilized GDF propeptides and uses thereof*, US2003/0104406 A1). Alternatively, the protein of interest could be a follistatin-domain-containing protein (see, e.g., Hill, et al., *GASP 1: a follistatin domain containing protein*, US 2003/0162714 A1, Hill, et al., *GASP1: a follistatin domain containing protein*, US 2005/0106154 A1, Hill, et al., *Follistatin domain containing proteins*, US 2003/0180306 A1).

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3) -IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (TLs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with the present invention.

G-Protein Coupled Receptors

Another class of polypeptides that have been shown to be effective as pharmaceutical and/or commercial agents includes growth factors and other signaling molecules. G-protein coupled receptors (GPCRs) are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

Specific defects in the rhodopsin gene and the V2 vasopressin receptor gene have been shown to cause various forms of autosomal dominant and autosomal recessive retinitis pigmentosa, nephrogenic diabetes insipidus. These receptors are of critical importance to both the central nervous system and peripheral physiological processes. The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of D. discoideum; and Family V, the fungal mating pheromone receptors such as STE2.

GPCRs include receptors for biogenic amines, for lipid mediators of inflammation, peptide hormones, and sensory signal mediators. The GPCR becomes activated when the receptor binds its extracellular ligand. Conformational changes in the GPCR, which result from the ligand-receptor interaction, affect the binding affinity of a G protein to the GPCR intracellular domains. This enables GTP to bind with enhanced affinity to the G protein.

Activation of the G protein by GTP leads to the interaction of the G protein cc subunit with adenylate cyclase or other second messenger molecule generators. This interaction regulates the activity of adenylate cyclase and hence production of a second messenger molecule, cAMP. cAMP regulates phosphorylation and activation of other intracellular proteins. Alternatively, cellular levels of other second messenger molecules, such as cGMP or eicosinoids, may be upregulated or downregulated by the activity of GPCRs. The G protein a subunit is deactivated by hydrolysis of the GTP by GTPase, and the α, β, and γ subunits reassociate. The heterotrimeric G protein then dissociates from the adenylate cyclase or other second messenger molecule generator. Activity of GPCR may also be regulated by phosphorylation of the intra- and extracellular domains or loops.

Glutamate receptors form a group of GPCRs that are important in neurotransmission. Glutamate is the major neurotransmitter in the CNS and is believed to have important roles in neuronal plasticity, cognition, memory, learning and some neurological disorders such as epilepsy, stroke, and neurodegeneration (Watson, S. and S. Arkinstall (1994) The G-Protein Linked Receptor Facts Book, Academic Press, San Diego Calif., pp. 130-132). These effects of glutamate are mediated by two distinct classes of receptors termed ionotropic and metabotropic. Ionotropic receptors contain an intrinsic cation channel and mediate fast excitatory actions of glutamate. Metabotropic receptors are modulatory, increasing the membrane excitability of neurons by inhibiting calcium dependent potassium conductances and both inhibiting and potentiating excitatory transmission of ionotropic receptors. Metabotropic receptors are classified into five subtypes based on agonist pharmacology and signal transduction pathways and are widely distributed in brain tissues.

The vasoactive intestinal polypeptide (VIP) family is a group of related polypeptides whose actions are also mediated by GPCRs. Key members of this family are VIP itself, secretin, and growth hormone releasing factor (GRF). VIP has a wide profile of physiological actions including relaxation of smooth muscles, stimulation or inhibition of secretion in various tissues, modulation of various immune cell activities. and various excitatory and inhibitory activities in the CNS. Secretin stimulates secretion of enzymes and ions in the pancreas and intestine and is also present in small amounts in the brain. GRF is an important neuroendocrine agent regulating synthesis and release of growth hormone from the anterior pituitary (Watson, S. and S. Arkinstall supra, pp. 278-283).

Following ligand binding to the GPCR, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cyclic AMP (e.g., by activation of adenylate cyclase), diacylglycerol or inositol phosphates. Greater than 20 different types of α-subunits are known in man, which associate with a smaller pool of β and γ subunits. Examples of mammalian G proteins include Gi, Go, Gq, Gs and Gt. G proteins are described extensively in Lodish H. et al. Molecular Cell Biology, (Scientific American Books Inc., New York, N.Y., 1995), the contents of which is incorporated herein by reference.

GPCRs are a major target for drug action and development. In fact, receptors have led to more than half of the currently known drugs (Drews, Nature Biotechnology, 1996, 14: 1516) and GPCRs represent the most important target for therapeutic intervention with 30% of clinically prescribed drugs either antagonizing or agonizing a GPCR (Milligan, G. and Rees, S., (1999) *TIPS*, 20: 118-124). This demonstrates that these receptors have an established, proven history as therapeutic targets.

In general, practitioners of the present invention will selected their polypeptide of interest, and will know its precise amino acid sequence. The techniques of the present invention have been successfully applied to production of diverse polypeptides including, for example, a human monoclonal antibody directed to growth and differentiation factor 8 (Examples 1, 3, 4, 7-14), humanized anti-Lewis Y antibody (Examples 5 and 6), anti-ABeta (Example 15) and a dimeric Fc-fusion protein of tumor necrosis factor receptor (Example 16), indicating that the present invention will be useful for expression of a variety of different polypeptides and proteins. Any given protein that is to be expressed in accordance with the present invention will have its own idiosyncratic characteristics and may influence the cell density or viability of the cultured cells, and may be expressed at lower levels than another polypeptide or protein grown under identical culture conditions. One of ordinary skill in the art will be able to appropriately modify the steps and compositions of the present invention in order to optimize cell growth and/or production of any given expressed polypeptide or protein.

Genetic Control Elements

As will be clear to those of ordinary skill in the art, genetic control elements may be employed to regulate gene expression of the polypeptide or protein. Such genetic control elements should be selected to be active in the relevant host cell. Control elements may be constitutively active or may be inducible under defined circumstances. Inducible control elements are particularly useful when the expressed protein is toxic or has otherwise deleterious effects on cell growth and/or viability. In such instances, regulating expression of the polypeptide or protein through inducible control elements may improve cell viability, cell density, and /or total yield of the expressed polypeptide or protein. A large number of control elements useful in the practice of the present invention are known and available in the art.

Representative constitutive mammalian promoters that may be used in accordance with the present invention include, but are not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art. Additionally, viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

Inducible promoters drive expression of operably linked coding sequences in the presence of an inducing agent and may also be used in accordance with the present invention. For example, in mammalian cells, the metallothionein promoter is induces transcription of downstream coding sequences in the presence of certain metal ions. Other inducible promoters will be recognized by and/or known to those of ordinary skill in the art.

In general, the gene expression sequence will also include 5' non-transcribing and 5' non-translating sequences involved with the initiation of transcription and translation, respectively, such as a TATA box, capping sequence, CAAT sequence, and the like. Enhancer elements can optionally be used to increase expression levels of the polypeptides or proteins to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521.

Systems for linking control elements to coding sequences are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, N.Y., 1989, which is incorporated herein by reference). Commercial vectors suitable for inserting preferred coding sequence for expression in various mammalian cells under a variety of growth and induction conditions are also well known in the art.

Introduction of Coding Sequences and Related Control Elements into Host Cells

Methods suitable for introducing into mammalian host cells nucleic acids sufficient to achieve expression of the polypeptides or proteins of interest are well known in the art. See, for example, Gething et al., Nature, 293:620-625 (1981); Mantei et al., Nature, 281:40-46 (1979); Levinson et al.; EP 117,060; and EP 117,058, all incorporated herein by reference.

For mammalian cells, preferred methods of transformation include the calcium phosphate precipitation method of Graham and van der Erb, *Virology*, 52:456-457 (1978) or the lipofectamine™. (Gibco BRL) Method of Hawley-Nelson, Focus 15:73 (1193). General aspects of mammalian cell host system transformations have been described by Axel in U.S. Pat. No. 4,399,216 issued Aug. 16, 1983. For various techniques for transforming mammalian cells, see Keown et al., *Methods in Enzymology* (1989), Keown et al., *Methods in Enzymology*, 185:527-537 (1990), and Mansour et al., *Nature*, 336:348-352 (1988). Non-limiting representative examples of suitable vectors for expression of polypeptides or proteins in mammalian cells include pCDNA1; pCD, see Okayama, et al. (1985) *Mol. Cell Biol.* 5:1136-1142; pMClneo Poly-A, see Thomas, et al. (1987) *Cell* 51:503-512; and a baculovirus vector such as pAC 373 or pAC 610.

In preferred embodiments, the polypeptide or protein is stably transfected into the host cell. However, one of ordinary skill in the art will recognize that the present invention can be used with either transiently or stably transfected mammalian cells.

Cells

Any mammalian cell or cell type susceptible to cell culture, and to expression of polypeptides, may be utilized in accordance with the present invention. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells ±DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., Annals N.Y. Acad. Sci., 383:44-68 (1982)); MRC 5 cells; FS4 cells; and a human hepatoma line (Hep G2). In a particularly preferred embodiment, the present invention is used in the culturing of and expression of polypeptides and proteins from CHO cell lines.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

As noted above, in many instances the cells will be selected or engineered to produce high levels of protein or polypeptide. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

Certain polypeptides may have detrimental effects on cell growth, cell viability or some other characteristic of the cells that ultimately limits production of the polypeptide or protein of interest in some way. Even amongst a population of cells of one particular type engineered to express a specific polypeptide, variability within the cellular population exists such that certain individual cells will grow better and/or produce more polypeptide of interest. In certain preferred embodiments of the present invention, the cell line is empirically selected by the practitioner for robust growth under the particular conditions chosen for culturing the cells. In particularly preferred embodiments, individual cells engineered to express a particular polypeptide are chosen for large-scale production based on cell growth, final cell density, percent cell viability, titer of the expressed polypeptide or any combination of these or any other conditions deemed important by the practitioner.

Cell Culture Phase

Typical procedures for producing a polypeptide of interest include batch cultures and fed-batch cultures. Batch culture processes traditionally comprise inoculating a large-scale production culture with a seed culture of a particular cell density, growing the cells under conditions conducive to cell growth and viability, harvesting the culture when the cells reach a specified cell density, and purifying the expressed polypeptide. Fed-batch culture procedures include an additional step or steps of supplementing the batch culture with nutrients and other components that are consumed during the growth of the cells. A persistent and unsolved problem with traditional batch and fed-batch cultures is the production of metabolic waste products, which have detrimental effects on cell growth, viability, and production of expressed polypeptides. Two metabolic waste products that have particularly detrimental effects are lactate and ammonium, which are produced as a result of glucose and glutamine metabolism, respectively. In addition to the enzymatic production of ammonium as a result of glutamine metabolism, ammonium also accumulates in cell cultures as a result of non-metabolic degradation over time. The present invention provides an improved method of large-scale production of polypeptides that minimizes the detrimental effects of ammonium and lactate by slowing and even reversing the accumulation of these waste products in cell cultures. One of ordinary skill in the art will recognize that the present invention can be employed in any system in which cells are cultured including, but not limited to, batch, fed-batch and perfusion systems. In certain preferred embodiments of the present invention, the cells are grown in batch or fed-batch systems.

Media

Traditional media formulations, including commercially available media such as Ham's F10 (Sigma), Minimal Essential Medium ([MEM], Sigma), RPMI-1640 (Sigma), and Dulbecco's Modified Eagle's Medium ([DMEM], Sigma), have contained relatively high levels of glucose and glutamine in comparison to other amino acids. These components have been thought to be required in abundance since they are the primary metabolic energy sources for the cells. However, rapid consumption of these nutrients leads to the accumulation of lactate and ammonium as described above. Additionally, high initial levels of glucose and glutamine and the subsequent accumulation of lactate and ammonium result in high osmolarity, a condition that by itself is often detrimental to cell growth, cell viability and the production of polypeptides.

The present invention provides a variety of media formulations that, when used in accordance with other culturing steps described herein, minimize and even reverse accumulation of lactate and ammonium. Media formulations of the present invention that have been shown to have beneficial effects on cell growth and/or viability or on expression of polypeptide or protein include one or more of: i) a cumulative amino acid amount per unit volume greater than about 70 mM, ii) a molar cumulative glutamine to cumulative asparagine ratio of less than about 2, iii) a molar cumulative glutamine to cumulative total amino acid ratio of less than about 0.2, iv) a molar cumulative inorganic ion to cumulative total amino acid ratio between about 0.4 to 1, and v) a combined cumulative amount of glutamine and asparagine per unit volume greater than about 16 mM. One of ordinary skill in the art will understand that "cumulative", as used above, refers to the total amount of a particular component or components added over the course of the cell culture, including components added at the beginning of the culture and subsequently added components. One of ordinary skill in the art will understand that the media formulations of the present invention encompass both defined and non-defined media.

Traditional media formulations begin with a relatively low level of total amino acids in comparison with the media formulations of the present invention. For example, the traditional cell culture medium known as DME-F12 (a 50:50 mixture of Dulbecco's Modified Eagle's medium and Ham's F12 medium) has a total amino acid content of 7.29 mM, and the traditional cell culture medium known as RPMI-1640 has a total amino acid content of 6.44 mM (See e.g., H. J. Morton, In Vitro, 6:89-108 (1970), R. G. Ham, Proc. Nat. Assoc. Sci. (USA), 53:288-293 (1965), G. E. Moore et al., J. Am. Medical Assn., 199:519-24 (1967), all incorporated herein by reference). In certain embodiments of the present invention, the amino acid concentration in the culture media is preferably greater than about 70 mM. More preferably still, the media formulations of the present invention contain amino acid concentrations greater than about 70 mM in the starting media. It has been shown that when amino acid concentrations of the starting media are in this range, cell density and titer are increased throughout the growth period of the culture (see Example 13).

Additionally, in certain embodiments of the present invention, the molar ratio of glutamine to asparagine in the culture media is reduced compared to other commercially and non-commercially available media. Preferably the molar ratio of glutamine to asparagine in the culture media is less than about two.

Additionally, in certain embodiments of the present invention, the molar ratio of glutamine to total amino acids in the culture media is reduced compared to other commercially and non-commercially available media. Preferably the molar ratio of glutamine to total amino acids in the culture media less than about 0.2.

An interesting and unexpected result of lowering the molar ratio of glutamine to asparagine or to the total concentration of amino acids in the starting media according to the present invention was that in addition to an observed decrease in the accumulation of ammonium, a decrease in the accumulation of lactate was seen as well. In certain embodiments, the accumulated levels of ammonium and lactate are not only lower than those in control cultures, but in fact actually decrease after an initial accumulation (for example, see Examples 3 and 7).

Boraston (U.S. Pat. No. 5,871,999) has disclosed a culture medium in which the molar ratio of total inorganic ions to total amino acids is between 1 and 10. Boraston showed that by providing culture medium in which the molar ratio of total inorganic ions to total amino acids is in this range, aggregation of CHO cells grown in the medium is decreased. In another preferred embodiment of the present invention, the molar ratio of total inorganic ions to total amino acids in the culture medium is reduced even further, to between about 0.4 to 1. As shown in Example 13, reducing this ratio from 1.75 to approximately 0.7 results in a marked increase in cell density and production of expressed polypeptide or protein throughout the growth period of the culture.

In another preferred embodiment of the present invention, the culture medium contains a combined glutamine and asparagine concentration of between about 16 and 36 mM. As shown in Example 14, Table 22, media which contain a combined total concentration of glutamine and asparagine within this range exhibit higher titers of expressed polypeptide than media which contain a combined total glutamine and asparagine outside this range. One of ordinary skill in the art will be able to choose the exact combined glutamine and asparagine concentration within this range in order to optimize cell growth and/or viability and to maximize the production of the expressed polypeptide.

Furthermore, one of ordinary skill in the art will recognize that any of the conditions listed above may be used either singly or in various combinations with one another. By utilizing media formulation which exhibit one, some or all of the above characteristics, one of ordinary skill in the art will be able to optimize cell growth and/or viability and to maximize the production of the expressed polypeptide.

Any of these media formulations disclosed in the present invention may optionally be supplemented as necessary with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, protein hydrolysates, or glucose or other energy source. In certain embodiments of the present invention, it may be beneficial to supplement the media with chemical inductants such as hexamethylene-bis (acetamide) ("HMBA") and sodium butyrate ("NaB"). These optional supplements may be added at the beginning of the culture or may be added at a later point in order to replenish depleted nutrients or for another reason. One of ordinary skill in the art will be aware of any desirable or necessary supplements that may be included in the disclosed media formulations.

Providing a Mammalian Cell Culture

Various methods of preparing mammalian cells for production of proteins or polypeptides by batch and fed-batch culture are well known in the art. As described above, a nucleic acid sufficient to achieve expression (typically a vector containing the gene encoding the polypeptide or protein of interest and any operably linked genetic control elements) may be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide or protein of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The starting cell density in the production bioreactor can be chosen by one of ordinary skill in the art. In accordance with the present invention, the starting cell density in the production bioreactor can be as low as a single cell per culture volume. In preferred embodiments of the present invention, starting cell densities in the production bioreactor can range from about $2\times10^2$ viable cells per mL to about $2\times10^3$, $2\times10^4$, $2\times10^5$, $2\times10^6$, $5\times10^6$ or $10\times10^6$ viable cells per mL and higher.

Initial and intermediate cell cultures may be grown to any desired density before seeding the next intermediate or final production bioreactor. It is preferred that most of the cells remain alive prior to seeding, although total or near total viability is not required. In one embodiment of the present invention, the cells may be removed from the supernatant, for example, by low-speed centrifugation. It may also be desirable to wash the removed cells with a medium before seeding the next bioreactor to remove any unwanted metabolic waste products or medium components. The medium may be the medium in which the cells were previously grown or it may be a different medium or a washing solution selected by the practitioner of the present invention.

The cells may then be diluted to an appropriate density for seeding the production bioreactor. In a preferred embodiment of the present invention, the cells are diluted into the same medium that will be used in the production bioreactor. Alternatively, the cells can be diluted into another medium or solution, depending on the needs and desires of the practitioner of the present invention or to accommodate particular requirements of the cells themselves, for example, if they are to be stored for a short period of time prior to seeding the production bioreactor.

Initial Growth Phase

Once the production bioreactor has been seeded as described above, the cell culture is maintained in the initial growth phase under conditions conducive to the survival, growth and viability of the cell culture. The precise conditions will vary depending on the cell type, the organism from which the cell was derived, and the nature and character of the expressed polypeptide or protein.

In accordance with the present invention, the production bioreactor can be any volume that is appropriate for large-scale production of polypeptides or proteins. In a preferred embodiment, the volume of the production bioreactor is at least 500 liters. In other preferred embodiments, the volume of the production bioreactor is 1000, 2500, 5000, 8000, 10,000, 12,000 liters or more, or any volume in between. One of ordinary skill in the art will be aware of and will be able to choose a suitable bioreactor for use in practicing the present invention. The production bioreactor may be constructed of any material that is conducive to cell growth and viability that does not interfere with expression or stability of the produced polypeptide or protein.

The temperature of the cell culture in the initial growth phase will be selected based primarily on the range of temperatures at which the cell culture remains viable. For example, during the initial growth phase, CHO cells grow well at 37° C. In general, most mammalian cells grow well within a range of about 25° C. to 42° C. Preferably, mammalian cells grow well within the range of about 35° C. to 40° C. Those of ordinary skill in the art will be able to select appropriate temperature or temperatures in which to grow cells, depending on the needs of the cells and the production requirements of the practitioner.

In one embodiment of the present invention, the temperature of the initial growth phase is maintained at a single, constant temperature. In another embodiment, the temperature of the initial growth phase is maintained within a range of temperatures. For example, the temperature may be steadily increased or decreased during the initial growth phase. Alternatively, the temperature may be increased or decreased by discrete amounts at various times during the initial growth phase. One of ordinary skill in the art will be able to determine whether a single or multiple temperatures should be used, and whether the temperature should be adjusted steadily or by discrete amounts.

The cells may be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days. In some cases, the cells may be allowed to grow for a month or more. The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

Shifting Culture Conditions

In accordance with the teaching of the present invention, at the end of the initial growth phase, at least one of the culture conditions may be shifted so that a second set of culture conditions is applied and a metabolic shift occurs in the culture. The accumulation of inhibitory metabolites, most notably lactate and ammonia, inhibits growth. A metabolic shift, accomplished by, e.g., a change in the temperature, pH, osmolality or chemical inductant level of the cell culture, may be characterized by a reduction in the ratio of a specific lactate production rate to a specific glucose consumption rate. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. As discussed above, the timing of the culture shift will be determined by the practitioner of the present invention, based on polypeptide or protein production requirements or the needs of the cells themselves.

When shifting the temperature of the culture, the temperature shift may be relatively gradual. For example, it may take several hours or days to complete the temperature change. Alternatively, the temperature shift may be relatively abrupt. For example, the temperature change may be complete in less than several hours. Given the appropriate production and control equipment, such as is standard in the commercial large-scale production of polypeptides or proteins, the temperature change may even be complete within less than an hour.

The temperature of the cell culture in the subsequent growth phase will be selected based primarily on the range of temperatures at which the cell culture remains viable and expresses recombinant polypeptides or proteins at commercially adequate levels. In general, most mammalian cells remain viable and express recombinant polypeptides or proteins at commercially adequate levels within a range of about 25° C. to 42° C. Preferably, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In one embodiment of the present invention, the temperature of the subsequent growth phase is maintained at a single, constant temperature. In another embodiment, the temperature of the subsequent growth phase is maintained within a range of temperatures. For example, the temperature may be steadily increased or decreased during the subsequent growth phase. Alternatively, the temperature may be increased or decreased by discrete amounts at various times during the subsequent growth phase. One of ordinary skill in the art will understand that multiple discrete temperature shifts are encompassed in this embodiment. For example, the temperature may be shifted once, the cells maintained at this temperature or temperature range for a certain period of time, after which the temperature may be shifted again—either to a higher or lower temperature. The temperature of the culture after each discrete shift may be constant or may be maintained within a certain range of temperatures.

In Example 16, data are shown that demonstrate the efficacy of employing two successive temperature changes, although it will be understood by those of ordinary skill in the art that in accordance with the present invention, three or more successive temperature changes may be used to increase cell viability or density and/or increase expression of recombinant polypeptides or proteins. The temperature or temperature ranges of the cell culture after each successive temperature shift may be higher or lower than the temperature(s) or temperature range(s) preceding the shift. In a preferred embodiment of the present invention, each successive temperature or temperature range is lower than the preceding temperature or temperature range.

Subsequent Production Phase

In accordance with the present invention, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C. As discussed above, multiple discrete temperature shifts may be employed to increase cell density or viability or to increase expression of the recombinant polypeptide or protein.

In accordance with the present invention, the cells may be maintained in the subsequent production phase until a desired cell density or production titer is reached. In one embodiment, the cells are maintained in the subsequent production phase until the titer to the recombinant polypeptide or protein reaches a maximum. In other embodiments, the culture may be harvested prior to this point, depending on the production requirement of the practitioner or the needs of the cells themselves. For example, the cells may be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it may be desirable to allow the viable cell density to reach a maximum, and then allow the viable cell density to decline to some level before harvesting the culture. In an extreme example, it may be desirable to allow the viable cell density to approach or reach zero before harvesting the culture.

In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

In certain cases, it may be beneficial or necessary to supplement the cell culture during the subsequent production phase with nutrients or other medium components that have been depleted or metabolized by the cells. For example, it might be advantageous to supplement the cell culture with nutrients or other medium components observed to have been depleted during monitoring of the cell culture (see 'Monitoring Culture Conditions' section below). Alternatively or additionally, it may be beneficial or necessary to supplement the cell culture prior to the subsequent production phase. As non-limiting examples, it may be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components may all be added to the cell culture at one time, or they may be provided to the cell culture in a series of additions. In one embodiment of the present invention, the supplementary components are provided to the cell culture at multiple times in proportional amounts. In another embodiment, it may be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture may be 1, 2, 3, 4, 5, 6, 7, 8, 9, 10, 15, 20, 25, 30, 35, 40, 45 or 50% of the volume of the cell culture prior to providing the supplementary components.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

Monitoring Culture Conditions

In certain embodiments of the present invention, the practitioner may find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase. In order to monitor certain cell culture conditions, it will be necessary to remove small aliquots of the culture for analysis. One of ordinary skill in the art will understand that such removal may potentially introduce contamination into the cell culture, and will take appropriate care to minimize the risk of such contamination.

As non-limiting example, it may be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density may be measured using a hemacytometer, a Coulter counter, or Cell density examination (CEDEX). Viable cell density may be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It may also be beneficial or necessary to monitor the post-translational modifications of the expressed polypeptide or protein, including phosphorylation and glycosylation.

Isolation of Expressed Polypeptide

In general, it will typically be desirable to isolate and/or purify proteins or polypeptides expressed according to the present invention. In a preferred embodiment, the expressed polypeptide or protein is secreted into the medium and thus cells and other solids may be removed, as by centrifugation or filtering for example, as a first step in the purification process. This embodiment is particularly useful when used in accordance with the present invention, since the methods and compositions described herein result in increased cell viability. As a result, fewer cells die during the culture process, and fewer proteolytic enzymes are released into the medium which can potentially decrease the yield of the expressed polypeptide or protein.

Alternatively, the expressed polypeptide or protein is bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide or protein may be isolated and purified by standard methods including, but not limited to, chromatography (e.g., ion exchange, affinity, size exclusion, and hydroxyapatite chromatography), gel filtration, centriftigation, or differential solubility, ethanol precipitation or by any other available technique for the purification of proteins (See, e.g., Scopes, *Protein Purification Principles and Practice* 2nd Edition, Springer-Verlag, New York, 1987; Higgins, S. J. and Hames, B. D. (eds.), *Protein Expression: A Practical Approach*, Oxford Univ Press, 1999; and Deutscher, M. P., Simon, M. I., Abelson, J. N. (eds.), *Guide to Protein Purification: Methods in Enzymology* (Methods in Enzymology Series, Vol 182), Academic Press, 1997, all incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Formulations

In certain preferred embodiments of the invention, produced polypeptides or proteins will have pharmacologic activity and will be useful in the preparation of pharmaceuticals. Inventive compositions as described above may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifugal agents, isotonic and absorption delaying agents, and the like, compatible with pharmaceutical administration. Supplementary active compounds can also be incorporated into the compositions.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions comprising a purified polypeptide or protein expressed from a mammalian cell line and a delivery agent are preferably delivered in the form of an aerosol spray from a pressured container or dispenser which contains a suitable propellant, e.g., a gas such as carbon dioxide, or a nebulizer. The present invention particularly contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments of the invention the compositions comprising a purified polypeptide expressed from a mammalian cell line and a delivery agent are formulated as large porous particles for aerosol administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In one embodiment, the compositions are prepared with carriers that will protect the polypeptide or protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active polypeptide or protein calculated to produce the desired therapeutic effect in association with the required pharmaceutical carrier.

The polypeptide or protein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with a polypeptide or protein as described herein can include a single treatment or, in many cases, can include a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention includes the use of inventive compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8*th* edition, Iowa State University Press; ISBN: 0813817439; 2001.

Inventive pharmaceutical compositions can be included in a container, pack, or dispenser together with instructions for administration.

The foregoing description is to be understood as being representative only and is not intended to be limiting. Alternative methods and materials for implementing the invention and also additional applications will be apparent to one of skill in the art, and are intended to be included within the accompanying claims.

EXAMPLES

Example 1

Enhanced Medium 1 for Anti-GDF-8 Fed-batch Process

Traditional fed-batch processes for cultivating cell lines have several drawbacks including the time and effort required to administer the feeds and the need for special equipment in large-scale bioreactors. The objective was to develop a batch media for the production of proteins of interest in large-scale bioreactors that requires minimal feeds.

Materials and Methods

STRAINS AND MEDIA: Chinese Hamster Ovary ("CHO") cells were engineered to express a monoclonal antibody against growth and differentiation factor 8 ("anti-GDF-8 cells") (see Veldman et al., *Neutralizing Antibodies Against GDF-8 and Uses Therefor*, US20040142382 A1). Anti-GDF-8 cells were used to test a new batch media. Medium 1 and Medium 2 were compared for their abilities to support high cell density and viability. The compositions of these media, as well as Medium 3 are listed in Table 1. Media are made by adding all the components save for $FeSO_4.7H_2O$. The media is then adjusted to pH 7.25, the osmolarity is recorded and $FeSO_4.7H_2O$ are then added.

CULTURE CONDITIONS: For flask experiments, anti-GDF-8 cells were grown in shake flasks and passaged three times. For bioreactor experiments, anti-GDF-8 cells were grown in media for 12 days, supplemented daily with either 2% by volume of 20× Medium 4 feed medium (Table 3) or 3% by volume of 16× Medium 4 (Table 4) after day 5. For the first 4 days, cells were grown at 37° C. On day 5, cells were shifted to 31° C.

SAMPLE ANALYSIS: Daily samples were taken from the cultures and were analyzed for amino acid, vitamin, iron, phosphate, glucose and glutamine levels.

TABLE 1

Compositions of Medium 1, Medium 2 and Medium 3.

| Amino Acids | Medium 1 | | Medium 2 | | Medium 3 | |
|---|---|---|---|---|---|---|
| | mg/L | mM | mg/L | mM | mg/L | mM |
| alanine | 96.03 | 1.08 | 17.80 | 0.20 | 24.87 | 0.28 |
| arginine | 1186.99 | 6.82 | 347.97 | 2.00 | 423.43 | 2.43 |
| asparagine.$H_2O$ | 713.59 | 4.76 | 75.00 | 0.50 | 173.90 | 1.16 |
| aspartic acid | 318.53 | 2.39 | 26.20 | 0.20 | 52.72 | 0.40 |
| cysteine.HCl.$H_2O$ | 70.01 | 0.40 | 70.19 | 0.40 | 70.01 | 0.40 |
| cystine.2HCl | 297.09 | 0.95 | 62.25 | 0.20 | 62.09 | 0.20 |
| glutamic acid | 158.59 | 1.08 | 29.40 | 0.20 | 41.08 | 0.28 |
| glutamine | 1892.40 | 12.96 | 1163.95 | 7.97 | 1162.40 | 7.96 |
| glycine | 95.88 | 1.28 | 30.00 | 0.40 | 35.92 | 0.48 |
| histidine.HCl.$H_2O$ | 369.10 | 1.76 | 46.00 | 0.22 | 75.27 | 0.36 |
| isoleucine | 623.63 | 4.76 | 104.99 | 0.80 | 151.90 | 1.16 |
| leucine | 852.31 | 6.51 | 104.99 | 0.80 | 172.69 | 1.32 |
| lysine.HCl | 945.96 | 5.20 | 145.99 | 0.80 | 218.38 | 1.20 |
| methionine | 291.82 | 1.96 | 29.80 | 0.20 | 53.55 | 0.36 |
| phenylalanine | 428.62 | 2.60 | 65.99 | 0.40 | 98.81 | 0.60 |
| proline | 372.25 | 3.24 | 68.99 | 0.60 | 96.40 | 0.84 |
| serine | 904.71 | 8.62 | 126.00 | 1.20 | 273.07 | 2.60 |
| threonine | 513.39 | 4.31 | 94.99 | 0.80 | 132.81 | 1.12 |

TABLE 1-continued

Compositions of Medium 1, Medium 2 and Medium 3.

|  | Medium 1 | | Medium 2 | | Medium 3 | |
| --- | --- | --- | --- | --- | --- | --- |
| tryptophan | 159.32 | 0.78 | 16.00 | 0.08 | 28.99 | 0.14 |
| tyrosine.2Na.2H$_2$O | 560.81 | 2.15 | 103.79 | 0.40 | 145.10 | 0.56 |
| valine | 505.36 | 4.32 | 93.99 | 0.80 | 131.17 | 1.12 |

| Vitamins | mg/L | µM | mg/L | µM | mg/L | µM |
| --- | --- | --- | --- | --- | --- | --- |
| biotin | 2.00 | 8.21 | 0.20 | 0.82 | 0.36 | 1.49 |
| calcium pantothenate | 22.02 | 46.27 | 2.24 | 4.71 | 4.03 | 8.47 |
| choline chloride | 87.67 | 630.74 | 8.98 | 64.60 | 16.11 | 115.92 |
| folic acid | 25.95 | 58.84 | 2.65 | 6.01 | 4.76 | 10.80 |
| inositol | 123.39 | 685.47 | 12.60 | 69.99 | 22.64 | 125.79 |
| nicotinamide | 19.60 | 160.70 | 2.02 | 16.56 | 3.61 | 29.62 |
| pyridoxal.HCl | 1.99 | 9.83 | 2.00 | 9.85 | 1.99 | 9.83 |
| pyridoxine.HCl | 18.06 | 87.67 | 0.03 | 0.15 | 1.67 | 8.10 |
| riboflavin | 2.20 | 5.85 | 0.22 | 0.59 | 0.40 | 1.06 |
| thiamine.HCl | 21.51 | 63.84 | 2.17 | 6.44 | 3.92 | 11.64 |
| vitamin B12 | 6.93 | 5.12 | 0.78 | 0.58 | 1.34 | 0.99 |

| Inorganic Salts | mg/L | mM | mg/L | mM | mg/L | mM |
| --- | --- | --- | --- | --- | --- | --- |
| CaCl$_2$ | 115.78 | 1.04 | 116.09 | 1.05 | 115.78 | 1.04 |
| KCl | 310.94 | 4.17 | 311.77 | 4.18 | 310.94 | 4.17 |
| Na$_2$HPO$_4$ | 70.81 | 0.50 | 70.99 | 0.50 | 70.81 | 0.50 |
| NaCl | 1104.96 | 18.92 | 5539.00 | 94.85 | 3704.96 | 63.44 |
| NaH$_2$PO$_4$.H$_2$O | 636.33 | 4.61 | 62.49 | 0.45 | 114.33 | 0.83 |
| MgSO$_4$ | 48.70 | 0.41 | 48.83 | 0.41 | 48.70 | 0.41 |
| MgSO$_4$.7H$_2$O | 0.03 | 95.00 | | | 8.60 | 95.00 |
| MgCl$_2$ | 28.53 | 0.30 | 28.61 | 0.30 | 28.53 | 0.30 |
| NaHCO$_3$ | 2000.00 | 23.81 | 2440.00 | 29.04 | 2440.00 | 29.04 |

| Trace Elements | µg/L | nM | µg/L | nM | µg/L | nM |
| --- | --- | --- | --- | --- | --- | --- |
| Sodium Selenite | 28.00 | 161.94 | 5.00 | 28.92 | 7.00 | 40.49 |
| Fe(NO$_3$)$_3$.9H$_2$O | 49.86 | 123.42 | 50.00 | 123.75 | 49.86 | 123.42 |
| CuSO$_4$ | 2.69 | 16.80 | 0.80 | 5.00 | 0.97 | 6.06 |
| CuSO$_4$.5H$_2$O | 11.24 | 45.00 | | | 7.49 | 30.00 |
| FeSO$_4$.7H$_2$O | 2503.85 | 9006.64 | 839.96 | 3021.45 | 1542.85 | 5549.81 |
| ZnSO$_4$.7H$_2$O | 2734.77 | 9528.82 | 429.96 | 1498.12 | 1383.80 | 4821.59 |
| MnSO$_4$.H$_2$O | 0.26 | 1.51 | | | 0.17 | 1.01 |
| Na2SiO3.9H$_2$O | 210.00 | 739.27 | | | 140.00 | 492.84 |
| (NH4)$_6$Mo$_7$O$_{24}$.4H$_2$O | 1.86 | 1.50 | | | 1.24 | 1.00 |
| NH$_4$VO$_3$ | 0.98 | 8.33 | | | 0.65 | 5.56 |
| NiSO$_4$.6H$_2$O | 0.20 | 0.74 | | | 0.13 | 0.49 |
| SnCl$_2$.2H$_2$O | 0.18 | 0.80 | | | 0.12 | 0.53 |

| Other Components | mg/L | µM | mg/L | µM | mg/L | µM |
| --- | --- | --- | --- | --- | --- | --- |
| Hydrocortisone | 0.23 | 0.64 | 0.04 | 0.10 | 0.09 | 0.24 |
| Putrescine.2HCl | 6.48 | 40.22 | 1.08 | 6.70 | 2.48 | 15.39 |
| linoleic acid | 0.22 | 0.80 | 0.04 | 0.14 | 0.06 | 0.20 |
| thioctic acid | 0.56 | 2.73 | 0.10 | 0.49 | 0.14 | 0.69 |
| D-glucose (Dextrose) | 16039.43 | 89107.92 | 6150.72 | 34170.64 | 11042.24 | 61345.76 |
| PVA | 2560.00 | | 2400.00 | | 2520.00 | |
| Insulin | 54.00 | | 10.00 | | 14.00 | |
| Sodium Pyruvate | 54.85 | 498.63 | 55.00 | 499.95 | 54.85 | 498.63 |

Results and Conclusions

FIG. 1 shows that growth rate of anti-GDF-8 cells was similar in both Medium 1 and Medium 2 in the flask experiments.

FIG. 2 shows that in bioreactors, Medium 1 exhibited a significant increase in final cell density and viability over Medium 3. The final titer also increased significantly, from 551 mg/L for the platform process to 976 mg/L with Medium 1 (data not shown). Temperature was shifted from 37° C. to 31° C. on day 5. Due to the unexpected high cell growth, the cultures were fed daily after day 5 with either 2% by volume of 20× Medium 4 or 3% by volume of 16× Medium 4. Thus, this is not a true batch experiment as originally intended. Asparagine and thiamine were supplemented in the feed media beginning on day 10.

In developing a concentrated batch media, several possible concerns need to be considered. First, concentrated nutrients might prove toxic to the cells. In the media developed in this Example, all nutrients and components were determined to be below the toxicity limits (data not shown).

Second, the concentrated batch media necessarily has a higher osmolarity than non-concentrated media, which has been shown to have detrimental effects on cell growth and viability. This problem can be circumvented by lowering the amount of NaCl in the starting media. Furthermore, the concentrated batch media contains insufficient levels of glucose to sustain growth for the entire culture period. Thus, cultures were supplemented daily after day 5 with a glucose feed.

Third, insulin and glutamine are susceptible to degradation during the 12 day culture period. Thus, the culture was supplemented with these components in addition to glucose.

Finally, iron will precipitate out of solution containing high concentrations of phosphate at high pH. This problem can be circumvented by adding iron at the end of the media preparation process, after the pH has been adjusted to an appropriate level.

Example 2

Development of Concentrated Feed Medium (Medium 5) for Anti-GDF-8 Cells in Fed-batch Process In Example 1, a batch process for culturing anti-GDF-8 cells using Medium 1 was developed. Due to the high cell density that resulted during the process, it was determined that supplementation of nutrients in addition to glucose and glutamine was still advantageous. However, supplementing the batch with 8× Medium 4 feed media would result in excessive dilution of the culture. A more concentrated feed media was developed in order to circumvent this problem.

Materials and Methods and Results

Table 2 lists the compositions of Medium 4A-1, Medium 4B, Trace B and Trace D used in the formulations of Tables 3-7.

TABLE 2

Compositions of Medium 4A-1, Medium 4B, Trace B and Trace D used in the formulations of Tables 3–7.

| | Medium 4A-1 | | Medium 4B | | Trace Elements B | | Trace Elements D | |
|---|---|---|---|---|---|---|---|---|
| Amino Acids | mg/L | mM | mg/L | mM | mg/L | mM | mg/L | mM |
| alanine | 17.80 | 0.20 | | | | | | |
| arginine | 191.00 | 1.10 | | | | | | |
| asparagine.$H_2O$ | 135.00 | 0.90 | | | | | | |
| aspartic acid | | | 66.50 | 0.50 | | | | |
| glutamic acid | | | 29.40 | 0.20 | | | | |
| glycine | 15.00 | 0.20 | | | | | | |
| histidine.HCl.$H_2O$ | 73.50 | 0.35 | | | | | | |
| isoleucine | 118.00 | 0.90 | | | | | | |
| leucine | 170.00 | 1.30 | | | | | | |
| lysine.HCl | 182.00 | 1.00 | | | | | | |
| methionine | 59.60 | 0.40 | | | | | | |
| phenylalanine | 82.50 | 0.50 | | | | | | |
| proline | 69.00 | 0.60 | | | | | | |
| serine | 158.00 | 1.50 | | | | | | |
| threonine | 95.20 | 0.80 | | | | | | |
| tryptophan | 32.60 | 0.16 | | | | | | |
| tyrosine.2Na.2$H_2O$ | | | 104.00 | 0.40 | | | | |
| valine | 93.60 | 0.80 | | | | | | |
| Vitamins | mg/L | µM | mg/L | µM | mg/L | mM | mg/L | mM |
| biotin | 0.41 | 1.68 | | | | | | |
| calcium pantothenate | 4.50 | 9.45 | | | | | | |
| choline chloride | 17.90 | 128.78 | | | | | | |
| folic acid | | | 5.30 | 12.02 | | | | |
| inositol | 25.20 | 140.00 | | | | | | |
| nicotinamide | 4.00 | 32.79 | | | | | | |
| pyridoxine.HCl | 4.10 | 19.90 | | | | | | |
| riboflavin | 0.45 | 1.20 | | | | | | |
| thiamine.HCl | 4.40 | 13.06 | | | | | | |
| vitamin B12 | 1.40 | 1.03 | | | | | | |
| Trace Elements | µg/L | nM | mg/L | µM | µg/L | nM | µg/L | nM |
| $(NH_4)_6Mo_7O_{24}.4H_2O$ | | | | | 1.24 | 1.00 | | |
| $CuSO_4$ | 0.43 | 2.69 | | | | | | |
| $CuSO_4.5H_2O$ | | | | | | | 7.49 | 30.00 |
| $FeSO_4.7H_2O$ | | | | | | | 834 | 3000 |
| $MnSO_4.H_2O$ | | | | | 0.17 | 1.01 | | |
| $Na_2SiO_3.9H_2O$ | | | | | 140.00 | 492.84 | | |
| $NH_4VO_3$ | | | | | 0.65 | 5.56 | | |
| $NiSO_4.6H_2O$ | | | | | 0.13 | 0.49 | | |
| $SnCl_2.2H_2O$ | | | | | 0.12 | 0.53 | | |
| $ZnSO_4.7H_2O$ | 230.00 | 801.39 | | | | | 863 | 3007 |

TABLE 2-continued

Compositions of Medium 4A-1, Medium 4B, Trace B and Trace D used in the formulations of Tables 3–7.

|  | Medium 4A-1 | | Medium 4B | | Trace Elements B | | Trace Elements D | |
|---|---|---|---|---|---|---|---|---|
| Other Components | μg/L | nM | μg/L | nM | μg/L | nM | μg/L | nM |
| linoleic acid | | | 42.00 | 0.15 | | | | |
| thioctic acid | | | 105.00 | 0.51 | | | | |
| D-glucose (Dextrose) | | | 1000000 | 5555.56 | | | | |

20× Medium 4.

The first concentrated media was developed as 20× Medium 4. The media formulation for 20× Medium 4 is provided in Table 3.

TABLE 3

20X Medium 4 feed media worksheet.

| Part | Component | Amount | Unit |
|---|---|---|---|
| I | Medium 4A-1 | 31.120 | g/L |
| | Nucellin ™ | 40.000 | ml/L |
| | H/P stock | 20.000 | ml/L |
| | Selenite Stock | 2.000 | ml/L |
| | PVA | 2.400 | g/L |
| | $NaH_2PO_4.H_2O$ | 2.610 | g/L |
| | $MgSO_4.7H_2O$ | 0.430 | g/L |
| | Aspartic acid | 1.330 | g/L |
| | Glutamic acid | 0.588 | g/L |
| | Linoleic acid | 0.840 | ml/L |
| | Thioctic acid | 2.100 | ml/L |
| | Tyrosine.2Na (Mw 225) | 1.790 | g/L |
| | 1000X Trace B | 6.000 | ml/L |
| | Glucose | 100.000 | g/L |
| | Glutamine | 14.600 | g/L |
| | pH to 7.0 | | |
| | Record Osmolarity | 1064.000 | mOsm |
| II | Cysteine (400 mM) | Add 108 ml Trace D, 0.25 g $FeSO_4.7H_2O$ to 280 ml Cysteine Stock | |
| III | Folic acid | 720 ml 6 mM Folic acid | |

Note:
Nucellin ™ is manufactured by Eli Lilly (Indianapolis, IN, USA);
H/P stock = 0.036 mg/mL hydrocortisone, 1.08 mg/mL Putrescine.2HCl.

The media formulation consists of 3 parts: I, II, III. Part I is the concentrated version of 8× Medium 4 with the individual components of Medium 4B except folic acid due to the concerns of the solubility of this vitamin. Part II is iron stock, Trace D and acidic cysteine, to avoid possible precipitation of iron if added in part I. Part III is folic acid stock. Part I is added 2% by volume daily starting on day 5 and parts II and III are added once on day 5 together with Part I.

The final pH of the feed media was adjusted to 7.0 and osmolarity was about 1064 mOsm. A 2% feed will result in a 2 g/L glucose, a 2 mM Glutamine and a 14 mOsm osmolarity increase to the culture.

2. 16× Medium 4.

To reduce the increase in osmolarity, the feed media was changed from 20× Medium 4 (2% by volume daily) to 16× Medium 4 (3% by volume daily). The media formulation for 16× Medium 4 is provided in Table 4.

TABLE 4

16X Medium 4 feed media worksheet.

| Part | Component | Amount | Unit |
|---|---|---|---|
| I | Medium 4A-1 | 24.896 | g/L |
| | Nucellin ™ | 32.000 | ml/L |
| | H/P stock | 16.000 | ml/L |
| | Selenite Stock | 1.600 | ml/L |
| | PVA | 2.400 | g/L |
| | $NaH_2PO_4.H_2O$ | 2.088 | g/L |
| | $MgSO_4.7H_2O$ | 0.344 | g/L |
| | Aspartic acid | 1.064 | g/L |
| | Glutamic acid | 0.470 | g/L |
| | Linoleic acid | 0.672 | ml/L |
| | Thioctic acid | 1.680 | ml/L |
| | Tyrosine.2Na (Mw 225) | 1.432 | g/L |
| | 1000X Trace B | 9.000 | ml/L |
| | Glutamine | 6.280 | g/L |
| | pH to 7.0 | | |
| | Record Osmolarity | 295.000 | mOsm |
| II | Cysteine (400 mM) | Add 108 ml Trace D, 0.25 g $FeSO_4.7H_2O$ to 280 ml Cysteine Stock | |
| III | Folic acid | 720 ml 6 mM Folic acid | |

Note:
Nucellin ™ is manufactured by Eli Lilly (Indianapolis, IN, USA);
H/P stock = 0.036 mg/mL hydrocortisone, 1.08 mg/mL Putrescine.2HCl.

In this modified 16× Medium 4, glucose was also eliminated to further reduce the osmolarity and give some flexibility of the glucose feed. Total osmolarity of the feed media is now 295 mOsm.

3. 16× Medium 4.

Changes were made to the 16× Medium 4 formulation. Iron stock solution was added in the feed resulting in a 0.45 μM addition each feed. Additionally, glucose was added back to give a 1.5 g/L addition every feed. The media formulation for this modified 16× Medium 4 is provided in Table 5.

TABLE 5

16X Medium 4 feed media worksheet.

| Part | Component | Amount | Unit |
|---|---|---|---|
| I | Medium 4A-1 | 24.896 | g/L |
| | Nucellin ™ | 32.000 | ml/L |
| | H/P stock | 16.000 | ml/L |
| | Selenite Stock | 1.600 | ml/L |
| | PVA | 2.400 | g/L |
| | $NaH_2PO_4.H_2O$ | 2.088 | g/L |
| | $MgSO_4.7H_2O$ | 0.344 | g/L |
| | Aspartic acid | 1.064 | g/L |
| | Glutamic acid | 0.470 | g/L |
| | Linoleic acid | 0.672 | ml/L |
| | Thioctic acid | 1.680 | ml/L |
| | Tyrosine.2Na (Mw 225) | 1.432 | g/L |

TABLE 5-continued

16X Medium 4 feed media worksheet.

| Part | Component | Amount | Unit |
|---|---|---|---|
| | 1000X Trace B | 9.000 | ml/L |
| | Glucose | 50.000 | g/L |
| | Glutamine | 7.300 | g/L |
| | pH to 7.0 | | |
| | $FeSO_4.7H_2O$ (1 mM stock) | 15.000 | ml/L |
| | Record Osmolarity | 607.000 | mOsm |
| II | Folic acid | 720 ml 6 mM Folic acid | |
| III | Cysteine (400 mM) | Add 108 ml Trace D, 0.25 g $FeSO_4.7H_2O$ to 280 ml Cysteine Stock | |

Note:
Nucellin ™ is manufactured by Eli Lilly (Indianapolis, IN, USA);
H/P stock = 0.036 mg/mL hydrocortisone, 1.08 mg/mL Putrescine.2HCl.

4. 16× Medium 4.

Here, the feed media (16× Medium 4) was made in combined media instead of 3 separate feeds as in the last several batches. Tests were done to ensure that folic acid could be dissolved at the concentration required and that neither iron nor folic acid precipitated out of solution after storage at either 4° C. or at room temperature for 6 days. The media formulation for the combined 16× Medium 4 is provided in Table 6.

TABLE 6

16X Medium 4 feed media worksheet.

| Component | Amount | Unit |
|---|---|---|
| Medium 4A-1 | 24.896 | g/L |
| Nucellin ™ | 32.000 | ml/L |
| H/P stock | 16.000 | ml/L |
| Selenite Stock | 1.600 | ml/L |
| PVA | 2.400 | g/L |
| $NaH_2PO_4.H_2O$ | 2.088 | g/L |
| $MgSO_4.7H_2O$ | 0.344 | g/L |
| Aspartic acid | 1.064 | g/L |
| Glutamic acid | 0.470 | g/L |
| Linoleic acid | 0.672 | ml/L |
| Thioctic acid | 1.680 | ml/L |
| Tyrosine.2Na (Mw 225) | 1.432 | g/L |
| Glucose | 66.700 | g/L |
| Glutamine | 7.300 | g/L |
| Folic acid | 70.560 | mg/L |
| Acidic cysteine (400 mM) | 6.250 | ml/L |
| $FeSO_4$ Stock (1 mM) | 23.000 | ml/L |
| 1000x Trace B | 9.000 | ml/L |
| 1000x Trace D | 3.300 | ml/L |
| pH expected 6.11 | Adjust to 7.0 | |
| Record Osmolarity | 724.000 | mOsm |

Note:
Nucellin ™ is manufactured by Eli Lilly (Indianapolis, IN, USA);
H/P stock = 0.036 mg/mL hydrocortisone, 1.08 mg/mL Putrescine.2HCl.

The final osmolarity of the media is 724 mOsm, with a daily glucose addition of 2 g/L and glutamine addition of 1.5 mM.

5. 12× Medium 4.

Here, several changes were made to the feed media. Medium 4B powder was used instead of addition of each individual ingredient in Medium 4B. Medium 4B powder was mixed with glucose and dissolved separately under basic conditions by titrating the solution to pH 10.25. Additional asparagine and thiamine were added since the amino acid and vitamin analysis results showed these two components were exhausted by the end of fed-batch process. Use of 12× Medium 4 further reduced the osmolarity increase when fed to the culture. The media formulation for 12× Medium 4 is provided in Table 7.

TABLE 7

12X Medium 4 feed media worksheet.

| Component | Amount | Unit |
|---|---|---|
| Medium 4A-1 | 18.672 | g/L |
| Nucellin ™ | 24.000 | ml/L |
| H/P stock | 12.000 | ml/L |
| Selenite Stock | 1.200 | ml/L |
| PVA | 2.400 | g/L |
| Asparagine.H2O | 1.620 | g/L |
| NaH2PO4.H2O | 1.566 | g/L |
| MgSO4.7H2O | 0.258 | g/L |
| Glutamine | 5.475 | g/L |
| Thiamine | 0.040 | g/L |
| Predissolved Medium 4B & Glucose | ~175 | ml/L |
| Acidic cysteine (400 mM) | 4.688 | ml/L |
| Record pH | | |
| Adjust pH to 7.2 with 5N HCl | | |
| $FeSO_4$ Stock (1 mM) | 17.250 | ml/L |
| 1000x Trace B | 6.750 | ml/L |
| 1000x Trace D | 2.475 | ml/L |
| Record pH (expect 7.18) | | |
| Record Osm | 566.000 | |
| Predissolved Medium 4B & Glucose * (for 1 L feed media) | | |
| Water | 150 ml | |
| Mix Medium 4B (14.5 g) with glucose (38.3 g) Adjust pH using 25% NaOH until dissolved (pH about 10.25) | Add in | |

Note:
Nucellin ™ is manufactured by Eli Lilly (Indianapolis, IN, USA);
H/P stock = 0.036 mg/mL hydrocortisone, 1.08 mg/mL Putrescine.2HCl.

The final osmolarity is 566 mOsm. A daily feed of 4% by volume gives an approximate osmolarity increase of 8.6, an increase in glucose of 2 g/L and an increase in glutamine of 1.5 mM. The 12× Medium 4 media formulation is also known as Medium 5. Medium 5 is easy to make compared to 20× Medium 4 or 16× Medium 4, and stable over 10 days either at room temperature or at 4° C. (data not shown).

Example 3

Glutamine Starvation Fed-batch Process for Anti-GDF-8 Cell Culture

CHO cells require glutamine in the starting media to survive. Traditionally, initial glutamine levels are high and glutamine is fed daily after day 5 until the end of the fed-batch process. Traditional fed-batch processes normally result in high lactate and ammonium levels in the cell cultures, which are known to have inhibitory effects on cell growth, cell density and recombinant protein expression. Fed-batch processes in which glucose is slowly added to the culture have been shown to lower lactate production and improve cell growth, cell density and recombinant protein expression. However, prior art methods for manipulation of glucose addition are not practical for large-scale manufacturing. Here, by utilizing culture media with lower starting levels of glutamine and eliminating glutamine from the feed, it is shown that lower levels of ammonium and lactate are produced, leading to increased cell viability. Additionally, in glutamine-starved cultures, recombinant protein expression is increased and final osmolarity is reduced.

Materials and Methods

STRAINS AND MEDIA: anti-GDF-8 cells were cultured in a fed-batch mode in Medium 1 in 1 L Bioreactor.

CULTURE CONDITIONS: Cells were grown for twelve days in 1 L Bioreactors. Temperature was shifted from 37° C. to 31° C. on either day 4 or day 5 depending on the cell growth. Three fed-batch processes were tested: a normal (control) process, a no glutamine feed process and a glutamine starvation process. Pertinent details of these processes are listed in Table 8 and Table 9.

TABLE 8

Fed-batch process in 1 L Bioreactors with no glutamine feed process.

|  | Control process | No glutamine feed process |
|---|---|---|
| Starting media Glutamine (mM) | 13 mM | 13 mM |
| Glutamine feed | 5 mM on Day 4 | No feed of glutamine |
| Feed media | Medium 5 (with 37.5 mM glutamine) | Medium 5 without glutamine |
| Feed schedule | 4% daily from Day 5 | 4% daily from Day 5 |
| Temperature shift to 31° C. | Day 4 | Day 5 |

TABLE 9

Fed-batch process in 1 L Bioreactors with glutamine starvation process

|  | Control process | Low glutamine process |
|---|---|---|
| Starting media Glutamine (mM) | 13 mM | 4 mM |
| Glutamine feed | 5 mM on Day 4 | No feed of glutamine |
| Feed media | Medium 5 (with 37.5 mM glutamine) | Medium 5 without glutamine |
| Feed schedule | 4% daily from Day 5 | 4% daily from Day 5 |
| Temperature shift to 31° C. | Day 4 | Day 5 |

SAMPLE ANALYSIS: Daily samples were taken from the cultures and were analyzed for cell density, cell viability, lactate, glutamine, and ammonium levels. Titer of expressed anti-GDF-8 antibody was also measured daily.

Results and Conclusions

FIG. 3 shows the cell density of cultures grown in either no glutamine feed or control fed-batch conditions. In both cases, cell density was similar over the course of the experiment.

FIG. 4 shows percent cell viability in cultures grown in either no glutamine feed or control fed-batch conditions. The no glutamine feed culture showed a markedly higher cell viability toward the end of the experiment, beginning on day 6.

FIG. 5 shows ammonium levels in cultures grown in either no glutamine feed or control fed-batch conditions. The no glutamine feed culture showed a marked decrease in ammonium levels toward the end of the experiment, beginning on day 4.

FIG. 6 shows lactate levels in cultures grown in either no glutamine feed or control fed-batch conditions. Lactate levels were slightly lower in the no glutamine feed culture throughout the course of the experiment.

FIG. 7 shows anti-GDF-8 antibody titer in cultures grown in either no glutamine feed or control fed-batch conditions. Final anti-GDF-8 antibody titer was higher in the no glutamine feed culture.

FIG. 8 shows the cell density of cultures grown in either glutamine-starved or control fed-batch conditions. In both cases, cell density was similar over the course of the experiment.

FIG. 9 shows cell viability in cultures grown in either glutamine-starved or control fed-batch conditions. In both cases, cell viability was similar over the course of the experiment.

FIG. 10 shows ammonium levels in cultures grown in either glutamine-starved or control fed-batch conditions. The glutamine-starved culture showed a marked decrease in ammonium levels throughout the course of the experiment.

FIG. 11 shows lactate levels in cultures grown in either glutamine-starved or control fed-batch conditions. The glutamine-starved culture showed a marked decrease in lactate levels throughout towards the end of the experiment, beginning on day 4.

FIG. 12 shows anti-GDF-8 antibody titer in cultures grown in either glutamine-starved or control fed-batch conditions. Final anti-GDF-8 antibody titer was higher in the glutamine-starved culture.

Collectively these results indicate that decreased glutamine levels are beneficial to cell cultures by reducing the amount of ammonium production, increasing cell viability and increasing titer of expressed anti-GDF-8 antibody. In addition, in the glutamine-starved cultures, low lactate levels were observed, possibly due to the decreased glucose consumption rate. Decreased ammonium and lactate levels also have the effect of reducing total osmolarity. Elevated osmolarity is also known to have inhibitory effects on cell growth and viability. Low initial glutamine levels together with the elimination of the glutamine feed also has the positive effect of reducing ammonium produced as a result of non-enzymatic glutamine degradation in stored media. Elimination of glutamine in the feed also simplifies the process of culturing anti-GDF-8 cells.

Example 4

Iron Dose Response of Anti-GDF-8 cells in Medium 1 and Medium 2.

Medium 1 is much more concentrated in nutrients than Medium 2. The optimum iron levels for cell growth in Medium 1 were determined in order to avoid problems with iron deficiency during cell culture.

Materials and Methods

Anti-GDF-8 cells were cultured in dishes for one passage in either Medium 1 or Medium 2. Iron concentrations of these media were manipulated by addition of different amounts of stock iron solution. Final cell densities were measured by CEDEX.

Results and Conclusions

FIG. 13 shows the Fe dose response of anti-GDF-8 cells in Medium 1 and Medium 2 containing different iron concentrations. In Medium 2, the cell density was relatively constant for iron concentrations ranging from 3 μM to 15 μM. In Medium 1, cell density increases with increasing iron concentration but reaches a maximum after approximately 5 μM. This difference could be due to the high nutrient content in Medium 1, which might reduce iron availability to the cells as a consequence of chelation of iron in the media.

These results indicate that iron levels should be kept above 5 μM to avoid problems with iron deficiency in Medium 1.

Example 5

Substitution of Glutamate for Glutamine in the Bioreactor Process

Three experiments were performed to test the effects of substituting glutamate for glutamine in an anti-Lewis Y cell culture process.

Materials and Methods

The experiments were performed in 10 L bioreactors at pH 7.1, 30% dissolved oxygen, and a starting temperature of 37° C. with a shift to 31° C. on day 5. Sparge and headspace gasses were 88% of a 93% air/7% $CO_2$ mix and 12% oxygen. The starting media in all experiments was Medium 1, which contains glutamine. Feed media and feed schedule including supplemental glucose and glutamine feeds are shown in Table 10. Columns labeled "Glutamate" were fed with modified Medium 5, containing no glutamine, but containing a molar concentration of glutamate equal to the molar glutamine concentration in standard Medium 5. Columns labeled glutamine were fed with standard Medium 5.

Bioreactors run with glutamate in the feed media have a lower ammonium concentration (FIG. 18) and a lower osmolarity (FIG. 19).

The binding ELISA assay was used to test activity of samples from the Glutamate 1 and Glutamate 1 experiments. The activities were similar: 110% of reference for the Glutamine 1 sample and 122% of reference for the Glutamate 1 sample (data not shown).

The substitution of glutamate for glutamine in these experiments does not have a significant effect on cell density. However, cell viability is lower in the Bioreactors fed with glutamine. Ammonium, lactate and osmolarity are lower in the Bioreactors fed with glutamate compared to those fed with glutamine. On average, anti-Lewis Y titer is higher in the Bioreactors fed with glutamate and activity is essentially the same under both conditions.

Example 6

Substitution of Glucose and Glutamine in the Anti-Lewis Y Cell Culture Process

The purpose of this experiment was to test the effects of substitution of glucose and glutamine with the feed media

TABLE 10

| | Feed schedule. | | | | | |
|---|---|---|---|---|---|---|
| | 9040-44 | | 9040-56 | | 9040-64 | |
| Day | Glutamate 1 | Glutamine 1 | Glutamate 2 | Glutamine 2 | Glutamate 3 | Glutamine 3 |
| 0 | | | | | | |
| 1 | | | | | | |
| 2 | | | | | | |
| 3 | | | | | | |
| 4 | | 5 mM gln | | 5 mM gln | 3 g/L gluc3 | 7.7 mM gln 2.9 g/l gluc |
| 5 | 3.6 g/gluc | 5 mM gln 5.5 g/L gluc | 3.5 g/L gluc | 5 mM gln 6 g/L gluc | 3 g/L gluc | 3 g/L gluc |
| 6 | 12% 16XMedium 4 | 12% 16XMedium 4 | 17% Medium 5 | 17% 16XMedium 4 | 29% Medium 5 | 29% Medium 5 |
| 7 | | 4 mM gln | | | | |
| 8 | | | | | | |
| 9 | | 2.5 g/L gluc | | | | |
| 10 | 10% 16XMedium 4 | 10% 16XMedium 4 | 8% Medium 5 | 5% 16XMedium 4 | | |
| 11 | | 1 g/L gluc | | | | |
| 12 | | | | | | |
| 13 | | 1 g/L gluc | | | | |

Results and Conclusions

Within each experiment, cell density is similar as shown in FIG. 14. Cell densities are low in the Glutamine 2 and Glutamate 2 experiments due to a pH deviation to about 6.7 on day 3 on the process. The drop in density between day 6 and 7 in the Glutamine 3 and Glutamate 3 experiments is due to the 29% media feed on day 6.

FIG. 15 shows cell viability of the glutamate and glutamine fed cultures. Viabilities remained higher during the second half of the process in the bioreactors containing glutamate fed cultures.

In Experiment 1, anti-Lewis Y titer is similar between the glutamate and glutamine fed cultures. FIG. 16 shows that in Experiments 2 and 3, anti-Lewis Y titers are lower in the glutamine fed reactors. The lower anti-Lewis Y titer observed in these reactors could be due to the high levels of lactate produced, as shown in FIG. 17.

listed in Table 11 below in the culturing of anti-Lewis Y cells (see Bogheart et al., *Antibody-targeted chemotherapy with the calicheamicin conjugate hu3S193-N-acetyl gamma calicheamicin dimethyl hydrazide targets Lewisy and eliminates Lewisy-positive human carcinoma cells and xenografts*, Clin. Can. Res. 10:4538-49 (2004)). Cell density, cell viability, anti-Lewis Y titer and ammonium levels were measured.

Materials and Methods

The experiment was performed in 250 ml shake flasks at a starting volume of 75 ml. All shake flasks were seeded at $0.25 \times 10^6$ cells/ml in Medium 2. The flasks were incubated at 37° C. in a 7% $CO_2$ incubator for 14 days. On days 3 and 4, the flasks were fed with 5% by volume of Medium 6 feed medium. The composition of Medium 6 is listed in Table 11. On days 5-13 the flasks were fed with 5% by volume of one of the feed solutions listed in Table 12. Each condition was performed in duplicate. Samples were taken daily for cell counts by CEDEX and assays for ammonium, glucose, and lactate

TABLE 11

| Composition of Medium 6. | | |
| --- | --- | --- |
| Amino Acids | mg/L | mM |
| alanine | 142.48 | 1.60 |
| arginine | 1528.84 | 8.79 |
| asparagine.H$_2$O | 1080.60 | 7.20 |
| aspartic acid | 532.40 | 4.00 |
| cystine.2HCl | 473.00 | 1.51 |
| glutamic acid | 235.38 | 1.60 |
| glutamine | 4820.00 | 33.01 |
| glycine | 120.07 | 1.60 |
| histidine.HCl.H$_2$O | 588.32 | 2.80 |
| isoleucine | 944.52 | 7.21 |
| leucine | 1360.75 | 10.39 |
| lysine.HCl | 1456.80 | 8.00 |
| methionine | 477.06 | 3.20 |
| phenylalanine | 660.36 | 4.00 |
| proline | 552.31 | 4.80 |
| serine | 1264.70 | 12.04 |
| threonine | 762.02 | 6.40 |
| tryptophan | 260.94 | 1.28 |
| tyrosine.2Na.2H$_2$O | 832.62 | 3.19 |
| valine | 749.21 | 6.40 |
| Vitamins | mg/L | mM |
| biotin | 3.28 | 0.01 |
| calcium pantothenate | 36.02 | 0.08 |
| choline chloride | 143.28 | 1.03 |
| folic acid | 42.43 | 0.10 |
| inositol | 201.71 | 1.12 |
| nicotinamide | 32.02 | 0.26 |
| pyridoxine.HCl | 32.82 | 0.16 |
| riboflavin | 3.60 | 0.01 |
| thiamine.HCl | 35.22 | 0.10 |
| vitamin B12 | 11.21 | 0.01 |
| Inorganic Salts | mg/L | mM |
| KH$_2$PO$_4$ | 1635.00 | 12.02 |
| MgSO$_4$.7H$_2$O | 171.98 | 0.70 |
| Trace Elements | µg/L | nM |
| Sodium Selenite | 40.00 | 231.35 |
| CuSO$_4$ | 3.44 | 21.51 |
| CuSO$_4$.5H$_2$O | 7.49 | 30.00 |
| FeSO$_4$.7H$_2$O | 2534 | 9115 |
| ZnSO$_4$.7H$_2$O | 2704 | 9421 |
| MnSO$_4$.H$_2$O | 0.17 | 1.01 |
| Na$_2$SiO$_3$.9H$_2$O | 140 | 492.84 |
| (NH$_4$)$_6$Mo$_7$O$_{24}$.4H$_2$O | 1.24 | 1.00 |
| NH$_4$VO$_3$ | 0.65 | 5.56 |
| NiSO$_4$.6H$_2$O | 0.13 | 0.49 |
| SnCl$_2$.2H$_2$O | 0.12 | 0.53 |
| AlCl$_3$.6H$_2$O | 1.20 | 4.97 |
| AgNO$_3$ | 0.17 | 1.00 |
| Ba(C$_2$H$_3$O$_2$)$_2$ | 2.55 | 9.98 |
| KBr | 0.12 | 1.01 |
| CdCl$_2$.2.5H$_2$O | 2.28 | 9.99 |
| CoCl$_2$.6H$_2$O | 2.38 | 10.00 |
| CrCl$_3$ | 0.32 | 2.02 |
| NaF | 4.20 | 100.02 |
| GeO$_2$ | 0.53 | 5.07 |
| KI | 0.17 | 1.02 |
| RbCl | 1.21 | 10.01 |
| ZrOCl$_2$.8H$_2$O | 3.22 | 9.99 |
| Other Components | µg/L | nM |
| Hydrocortisone | 288 | 0.79 |
| Putrescine.2HCl | 8000 | 49.66 |
| linoleic acid | 336.25 | 1.20 |

TABLE 11-continued

| Composition of Medium 6. | | |
| --- | --- | --- |
| thioctic acid | 840.63 | 4.08 |
| Other Components | mg/L | mM |
| D-glucose (Dextrose) | 33005.99 | 183.37 |
| PVA | 2400.00 | |
| Nucellin ™ | 80.00 | |

TABLE 12

| Feeds on days 5–13. Modified Medium 6 contains no glucose or glutamine. | |
| --- | --- |
| GluGln | Modified Medium 6 + 43 g/L glucose + 4.82 g/L glutamine (control) |
| Glu | Modified Medium 6 + 43 g/L glucose + 4.82 g/L glutamate |
| GluAsp | Modified Medium 6 + 43 g/L glucose + 4.36 g/L asparagine |
| GluGlyGln | Modified Medium 6 + 43 g/L glucose + 6.71 g/L glycylglutamine |
| GluGlu | Modified Medium 6 + 43 g/L galactose + 4.82 g/L glutamine |
| GalGlu | Modified Medium 6 + 43 g/L galactose + 4.82 g/L glutamate |
| GalGln | Modified Medium 6 + 43 g/L galactose + 4.36 g/L asparagine |
| GalGlyGln | Modified Medium 6 + 43 g/L galactose + 6.71 g/L glycylglutamine |
| GalAsp | Medium 6 + 43 g/L glucose |

Results and Conclusions

The highest cell density was seen when glutamate or glycylglutamine was substituted for glutamine in the presence of either glucose or galactose in the feed media. Cell density was generally lower in the cultures fed with glucose/glutamine, galactose/glutamine, or glucose only (FIG. 20). Final viability was highest in the cultures fed with glucose only, followed by the cultures fed with glucose/glutamate. The lowest viability was seen in the cultures fed with glutamine or asparagine combined with either glucose or galactose (FIG. 21).

Day 14 titer was highest in the glucose/glycylglutamine and the glucose/glutamate fed cultures at about 700 µg/ml. Titer was lowest in the galactose/glycylglutamine and the galactose/asparagine fed cultures at about 500 µg/ml. Titer in the glucose/glutamine control was about 570 µg/ml (FIG. 22).

The lowest ammonium levels were seen in the flasks fed with glucose/glutamate or glucose only. The flasks fed with galactose/glutamate, glucose/glutamine, glucose/glycylglutamine, and glucose/asparagine showed intermediate levels of ammonium. The flasks fed with galactose/asparagine, galactose/glycylglutamine, and galactose/glutamine had the highest levels of ammonium (FIG. 23).

Glucose levels remained above 1 g/L in all flasks fed with galactose until day 11. From day 11 through day 14, the glucose in these cultures was never completely depleted, remaining between 0.6 and 1 g/L, with no significant differences between the different cultures.

Glucose levels increased in all flasks fed with glucose or glucose combined with another substrate until day 10. From day 10 through day 14 in these cultures, glucose levels remained fairly constant and similar to each other. On day 14 about 8.4 g/L glucose remained in the glucose/glutamate fed cultures and about 10.8 g/L glucose remained in the cultures fed with glucose only.

Lactate levels reached a high of about 2.4 g/L on day 5, when conditions were the same for all cells, and dropped to essentially zero in all cultures by day 14. Lactate levels were highest from day 10 through day 14 in the glucose/glutamine control, but were below 1 g/L during this time (data not shown).

All conditions tested in this experiment resulted in higher cell density than the control glucose/glutamine condition. All conditions tested except the galactose/asparagine condition resulted in higher final viability than either the glucose/glutamine control or the galactose/glutamine fed condition. Titer in the glucose/glutamine control was about 570 µg/ml compared to a high of about 700 µg/ml in the glucose/glycylglutamine fed condition and the glucose/glutamate fed condition.

Example 7

Evaluation of a Glutamine Starved Batch Process for the Production of Anti-GDF-8

Typical fed-batch production methods require multiple feeds over the culture period. These feeds are designed to replace nutrients in the medium that may have been depleted by the cells or may have degraded during the batch. These feeds create complications when the process is scaled up to be used in larger reactors, such as the need for an impeller jump (see FIG. 24). Furthermore, the feeds dilute the amount of anti-GDF-8 already secreted into the culture and therefore affect the harvest titer. The use of a batch process would allow inoculation of the bioreactor at full volume, instead of at a partial volume so as to accommodate the feeds, which would remove the necessity of an impeller jump and greatly reduce any dilution effect on productivity.

Glutamine is one of the most important reasons that a fed-batch approach is used since it is not stable at 37° C. and it had been thought that it needed to be replenished during a batch culture. However, results of Examples 2, 5, and 6, in which a glutamine starvation strategy was tested, showed a significant increase in productivity compared to a control reactor that was fed glutamine. This result was combined with the batch process to create a glutamine starvation batch process that was tested in this Example.

Materials and Methods

Anti-GDF-8 cells were grown in 1 L Bioreactors for 12 days according to the following four growth conditions. Bioreactor parameters for all conditions were kept the same. Dissolved oxygen was maintained at no lower than 23% of air saturation by sparging with air and pH was maintained at 7.00 by the addition of a solution containing sodium bicarbonate at 0.58 M and sodium carbonate at 0.71 M. The temperature of all cultures was maintained at 37° C. for the first four days of the batch. On the fourth day of the batch the temperature of all the bioreactors was lowered to 31° C. and maintained at this point for the duration of the batch. The control and fed-batch cultures were fed with 8%, 12%, and 8% total reactor volume of their respective feed media on days 5, 7, and 10, respectively.

1) Control.
   Inoculation medium Medium 7 (see Table 13).
   Feed Medium 8, fed on days 5, 7, and 10 (see Table 13).
   Feed 5 mM of glutamine on day 4.
   Lower the temperature to 31° C. on day 4.
2) Fed-batch glutamine starvation.
   Inoculation medium Medium 7 with only 4 mM of glutamine (see Table 13).
   Feed Medium 8 without glutamine, fed on days 5, 7, and 10 (see Table 13).
   No glutamine feed on day 4.
   Lower the temperature to 31° C. on day 4.
3) Batch glutamine starvation.
   Inoculation medium new batch medium with only 4 mM of glutamine (see Table 13).
   No feed medium.
   No glutamine feed.
   Lower the temperature to 31° C. on day 4.
   Add 5 g/L of glucose on day 8.
4) Batch glutamine starvation supplemented on day 8.
   Inoculation medium new batch medium with only 4 mM of glutamine (see Table 13).
   No feed medium.
   No glutamine feed.
   Lower the temperature to 31° C. on day 4.
   Add 4 g of glucose, 375 mg of Asparagine, 3 mL of 1 mM FeSO$_4$ stock, 3.33 mL of 5 g/L Nucellin™ stock, 2.57 mL of 36 mg/L Hydrocortisone and 1.0 g/L Putrescine stock solution, 0.23 mL of 50 mg/L Sodium Selenite stock, and 13.1 mg of Thiamine on day 8.

TABLE 13

Compositions of media used.

| Amino acids | MW | Medium 7 mM | Medium 8 mM | Batch media mM |
| --- | --- | --- | --- | --- |
| L-Alanine | 89.0 | 1.08 | 2.4 | 0.2 |
| L-Arginine | 174.0 | 6.84 | 13.2 | 4 |
| L-Asparagine.H$_2$O | 150.0 | 4.76 | 21.4 | 7.5 |
| L-Aspartic acid | 133.0 | 2.40 | 6 | 1.65 |
| L-Cysteine.HCl.H$_2$O | 176.0 | 0.40 | 0 | 0.4 |
| L-Cystine.2HCl | 313 | 0.95 | 1.875 | 1 |
| L-Glutamic acid | 147.0 | 1.08 | 2.4 | 1.08 |
| L-Glutamine | 146.0 | 13.00 | 37.5 | 4 |
| Glycine | 75.0 | 1.28 | 2.4 | 1.54 |
| L-Histidine.HCl.H$_2$O | 210.0 | 1.76 | 4.2 | 1.76 |
| L-isoleucine | 131.0 | 4.76 | 10.8 | 2.83 |
| L-leucine | 131.0 | 6.52 | 15.6 | 4.7 |
| Lysine.HCl | 182.0 | 5.20 | 12 | 5.2 |
| L-Methionine | 149.0 | 1.96 | 4.8 | 2.6 |
| L-Phenylalanine | 165.0 | 2.60 | 6 | 2.2 |
| L-proline | 115.0 | 3.24 | 7.2 | 4.1 |

TABLE 13-continued

Compositions of media used.

| | | | | |
|---|---|---|---|---|
| L-serine | 105.0 | 8.60 | 18 | 8.6 |
| L-threonine | 119.0 | 4.32 | 9.6 | 3.2 |
| L-tryptophan | 204.0 | 0.78 | 1.92 | 1.04 |
| L-tyrosine 2Na.2H$_2$O | 261.0 | 2.16 | 4.8 | 1.75 |
| L-valine | 117.0 | 4.32 | 9.6 | 4 |
| Vitamins | | uM | uM | uM |
| Biotin | 244.0 | 8.31 | 20.4 | 11 |
| D-Calcium pantothenate | 476.0 | 46.06 | 112.8 | 46.06 |
| choline chloride | 139.0 | 632.2 | 1548 | 840 |
| folic acid | 441.0 | 58.8 | 144 | 58.8 |
| l-inositol | 180.0 | 686 | 1680 | 911 |
| nicotinamide | 122.0 | 161.7 | 396 | 215 |
| pyridoxine.HCl | 206.0 | 88.15 | 240 | 88 |
| pyridoxal.HCl | 203.0 | 10 | 0 | 10 |
| riboflavin | 376.0 | 5.37 | 13.2 | 1.1 |
| thiamine.HCl | 337.0 | 63.7 | 274.7 | 117 |
| vitamin B12 | 1355.0 | 4.9 | 12 | 7.8 |
| Inorganic salts | | | | |
| NaCl | 58.5 | 18.8 mM | | |
| KCl | 74.6 | 4.2 mM | | 4.19 mM |
| CaCl$_2$ | 111 | 1.05 mM | | 1.05 mM |
| Sodium Selenite | 173 | 27 ug/L | 60 ug/L | 60 ug/L |
| NaH$_2$PO$_4$.H$_2$O | 142 | 4.68 mM | 11 mM | 4.68 mM |
| Na$_2$HPO$_4$ | 138 | 0.5 mM | | 0.3986 mM |
| MgSO$_4$ | 120 | 1.15 mM | 1.05 mM | 1.15 mM |
| MgCl$_2$ | 95 | 0.3 mM | | 0.3 mM |
| FeSO$_4$.7H$_2$O | 278 | 9 uM | 24.675 uM | 9 uM |
| Fe(NO$_3$)$_3$.9H$_2$O | 404 | 0.125 uM | | 0.124 um |
| ZnSO$_4$.7H$_2$O | 287 | 9.2 uM | 17 uM | 9.2 um |
| CuSO$_4$ | 160 | 0.05 uM | 0.074 uM | 0.064 um |
| NaHCO$_3$ | 84 | 23.8 mM | | 23.8 mM |
| Others | | | | |
| Glucose | 180 | 16 g/L | 38.3 g/L | 15 g/L |
| Polyvinyl alcohol | | 2.56 g/L | 2.4 g/L | 2.56 g/L |
| Hydrocortisone | 363 | 0.23 mg/L | 0.43 mg/L | 0.28 mg/L |
| Putrescine.2HCl | 161 | 6.4 mg/L | 12 mg/L | 7.7 mg/L |
| Sodium pyruvate | 110 | 500 uM | | 500 uM |
| linoleic acid | 280 | 0.81 uM | 1.8 uM | 0.81 uM |
| thioctic acid | 206 | 2.7 uM | 6 uM | 2.7 uM |
| Nucellin ™ | | 54 mg/L | 120 mg/L | 50 mg/L |
| 1000x Trace B | | 1.5 ml/L | 6.75 ml/L | 1.5 ml/L |

Results and Conclusions

Cell growth for the first 4 days was similar for the control and batch processes, while the glutamine starved fed-batch process had a slightly lower cell density and remained a little lower for the rest of the batch. Both batch processes maintained higher cell densities for the duration of the batch, probably due to the lack of any significant dilution (see FIG. 25). Viabilities of all the cultures were the same up to day 8. However, it is interesting to note that on day 11, the viability of the batch process that was not supplemented was lower than the other three bioreactors and ended up significantly lower by the final day. This suggests that the batch medium could still be optimized since the supplemented batch process had a viability that was the same as the fed-batch bioreactors (see FIG. 26).

Cells cultured in either glutamine starved batch process or in the glutamine starved fed-batch process outperformed the same cells cultured in the control fed-batch process in productivity. The control fed-batch process had a harvest day titer of 685 µg/mL, as expected, while the glutamine starved fed-batch process had a harvest titer of 1080 µg/mL, about 58% higher than the control. This is similar to results seen previously. The glutamine starved non-supplemented batch process had a harvest day titer of 960 µg/mL, 40% higher than the control, similar to the glutamine starved fed-batch process, while the supplemented glutamine starved batch process had the highest titer at 1296 µg/mL. This is an 89% increase over the control (see FIG. 27).

When the inhibitor levels for the four conditions were analyzed the results showed that the lactate and ammonia levels for all three glutamine starved processes were significantly lower than the control. In fact, after day 4, those three conditions either stopped producing or started consuming lactate while the control continued to produce lactate throughout the batch (see FIG. 28). As expected, the ammonia levels were much lower in the glutamine starved processes and declined after day 4, while the control continued to produce ammonia (see FIG. 29).

In this Example, combining a batch process with a glutamine starvation strategy resulted in a 40% improvement in productivity over the control fed-batch process for anti-GDF-8 cells. The data also suggest that with some optimization of the batch medium, an almost 2-fold improvement in productivity can be attained. This improvement in productivity can be attributed to two factors. First, glutamine starvation increases productivity either directly or by keeping ammonia and lactate levels very low. Second, because of the absence of feeds, the titer is not diluted during the batch. Increased productivity together with the ease of operation inherent in a batch process makes this an attractive option for producing recombinant polypeptides.

Example 8

Effects of Glutamine and Asparagine Concentrations in Batch Media on Anti-GDF-8 Cell Culture Process In Examples 2, 5 and 6, it was demonstrated that glutamine starvation conferred benefits on fed-batch cultures in two cell lines, including increased cell growth, cell viability and titer as well as decreased production of lactate and ammonium. Asparagine also seems to play a role in batch media.

Materials and Methods

Anti-GDF-8 cells were cultured for twelve days in 1L Bioreactors in modified Medium 9 with differing concentrations of glutamine and asparagine. Base Medium 9 composition is listed in Table 14. Experimental variations on this base composition are listed in Table 15. The cultures were incubated at 37° C. for the first 5 days with the exception of Reactor 4, whose temperature was 30° C. for the first day due to temperature control problems. The cultures were shifted to 31° C. on day 6. On day 7, the cultures were fed once with 5% by volume Medium 5 lacking glutamine. Cultures were measured daily for cell density, anti-GDF-8 titer, lactate and ammonium levels.

TABLE 14

Composition of Medium 9.

| Amino Acids | mg/L | mM |
|---|---|---|
| alanine | 17.80 | 0.20 |
| arginine | 696.00 | 4.00 |
| asparagine.$H_2O$ | 3000.00 | 20.00 |
| aspartic acid | 219.45 | 1.65 |
| cysteine.HCl.$H_2O$ | 70.40 | 0.40 |
| cysteine.2HCl | 468.75 | 1.50 |
| monosodium glutamate | 33.80 | 0.20 |
| glutamine | 584.00 | 4.00 |
| glycine | 115.50 | 1.54 |
| histidine.HCl.$H_2O$ | 474.60 | 2.26 |
| isoleucine | 570.73 | 4.36 |
| leucine | 1030.70 | 7.87 |
| lysine.HCl | 1401.40 | 7.70 |
| methionine | 387.40 | 2.60 |
| phenylalanine | 507.00 | 3.07 |
| proline | 539.50 | 4.69 |
| serine | 1052.00 | 10.02 |
| threonine | 564.80 | 4.75 |
| tryptophan | 274.16 | 1.34 |
| tyrosine.2Na.2$H_2O$ | 745.75 | 2.86 |
| valine | 749.00 | 6.40 |

| Vitamins | mg/L | mM |
|---|---|---|
| biotin | 2.68 | 0.01 |
| calcium pantothenate | 21.92 | 0.05 |
| choline chloride | 158.46 | 1.14 |
| folic acid | 25.93 | 0.06 |
| inositol | 163.98 | 0.91 |
| nicotinamide | 26.23 | 0.22 |
| pyridoxal.HCl | 2.03 | 0.01 |
| pyridoxine.HCl | 36.13 | 0.18 |
| riboflavin | 2.41 | 0.01 |
| thiamine.HCl | 39.43 | 0.12 |
| vitamin B12 | 21.17 | 0.02 |

TABLE 14-continued

Composition of Medium 9.

| Inorganic Salts | mg/L | mM |
|---|---|---|
| $CaCl_2$ | 116.55 | 1.05 |
| KCl | 312.90 | 4.19 |
| $Na_2HPO_4$ | 56.60 | 0.40 |
| NaCl | 1100.00 | 18.80 |
| $NaH_2PO_4.H_2O$ | 645.84 | 4.68 |
| $MgSO_4$ | 138.00 | 1.15 |
| $MgCl_2$ | 28.50 | 0.30 |
| $NaHCO_3$ | 2000.00 | 23.81 |

| Trace Elements | µg/L | nM |
|---|---|---|
| Sodium Selenite | 69.16 | 400.00 |
| $Fe(NO_3)_3.9H_2O$ | 50.00 | 123.76 |
| $CuSO_4$ | 10.24 | 64.00 |
| $CuSO_4.5H_2O$ | 99.88 | 400.00 |
| $FeSO_4.7H_2O$ | 4170 | 15000 |
| $ZnSO_4.7H_2O$ | 2640 | 9200 |
| $MnSO_4.H_2O$ | 33.80 | 200.00 |
| $Na_2SiO_3.9H_2O$ | 284.07 | 1000 |
| $(NH_4)_6Mo_7O_{24}.4H_2O$ | 247.20 | 200.00 |
| $NH_4VO_3$ | 2.34 | 20.00 |
| $NiSO_4.6H_2O$ | 5.26 | 20.00 |
| $SnCl_2.2H_2O$ | 0.90 | 4.00 |
| $AlCl_3.6H_2O$ | 0.97 | 4.00 |
| KBr | 0.48 | 4.00 |
| $CrCl_3$ | 15.83 | 100.00 |
| NaF | 0.17 | 4.00 |
| $GeO_2$ | 0.42 | 4.00 |
| KI | 33.20 | 200.00 |
| RbCl | 0.48 | 4.00 |
| $H_3BO_3$ | 12.37 | 200.00 |
| LiCl | 0.17 | 4.00 |

| Other Components | µg/L | nM |
|---|---|---|
| Hydrocortisone | 540.00 | 1.49 |
| Putrescine.2HCl | 15000 | 93.11 |
| linoleic acid | 290.00 | 1.04 |
| thioctic acid | 716.00 | 3.48 |

| Other Components | mg/L | mM |
|---|---|---|
| D-glucose (Dextrose) | 15000.00 | 83.33 |
| PVA | 2560.00 | |
| Nucellin ™ | 50.00 | |
| Sodium Pyruvate | 55.00 | 0.50 |

TABLE 15

Glutamine and Asparagine conditions tested.

| | Reactor 1 | Reactor 2 | Reactor 3 | Reactor 4 | Reactor 5 | Reactor 6 |
|---|---|---|---|---|---|---|
| Cell line | anti-GDF-8 | | | | | |
| Media | Batch media (Medium 9) | | | | | |
| Glutamine levels | 1 mM | 1 mM | 1 mM | 4 mM | 4 mM | 4 mM |
| Asparagine levels | 8 mM | 12 mM | 20 mM | 8 mM | 12 mM | 20 mM |
| Seeding density (×10$^6$/ml) | 0.3 to 0.35 | | | | | |
| Feed media | Medium 5-Glutamine, 5% on Day 7 | | | | | |
| Culture Days | 12 | | | | | |
| Temperature shift (37–31° C.) | Day 6 | Day 6 | Day 6 | Day 5 | Day 5 | Day 4 |

Results and Conclusions

FIGS. 30, 31, 32 and 33 show the cell growth of anti-GDF-8 cells, anti-GDF-8 titer, lactate levels and ammonium levels, respectively, throughout the course of the experiments under the various experimental conditions.

Under all experimental conditions, 4 mM glutamine is better than 1 mM glutamine at all the Asparagine levels tested. At comparable glutamine levels, 12 mM and 20 mM asparagine conditions are better than 8 mM asparagine conditions. Decreased lactate and $NH_4$ levels were observed at the end of the culture for all conditions tested.

Example 9

Effects of Glutamine and Asparagine Concentrations in Batch Media on Anti-GDF-8 Cell Culture Process In Example 8, it was demonstrated that Medium 9 containing an initial concentration of 4 mM glutamine performs better than media containing 1 mM glutamine, regardless of asparagine levels. This example demonstrates the effect of media containing 13 mM glutamine levels and various asparagine levels.

Materials and Methods

Anti-GDF-8 cells were cultured for twelve days in 1 L Bioreactors in modified Medium 9 with differing concentrations of glutamine and asparagine as listed in Table 16. The cultures were incubated at 37° C. for the first 3 days. The cultures were then shifted to 31° C. on day 4. On day 7, the cultures were fed once with 5% by volume Medium 5 lacking glutamine. Cultures were measured periodically for cell density, cell viability, lactate, ammonium levels and glutamine levels, anti-GDF-8 titer, and osmolarity.

TABLE 16

Glutamine and Asparagine conditions tested.

| | Reactor 1 | Reactor 2 | Reactor 3 | Reactor 4 | Reactor 5 | Reactor 6 |
|---|---|---|---|---|---|---|
| Cell line | anti-GDF-8 | | | | | |
| Media | Batch media (Medium 9) | | | | | |
| Glutamine levels | 4 mM | 4 mM | 13 mM | 13 mM | 13 mM | 13 mM |
| Asparagine levels | 20 mM | 20 mM | 20 mM | 12 mM | 12 mM | 8 mM |
| Seeding density ($\times 10^6$/ml) | 0.3 to 0.35 | | | | | |
| Feed media | Medium 5 lacking glutamine, 5% on Day 7 | | | | | |
| Culture Days | 12 | | | | | |
| Temperature shift (37–31° C.) | Day 4 | Day 4 | Day 4 | Day 4 | Day 4 | Day 4 |

Results and Conclusions

FIGS. 34, 35, 36, 37, 38, 39 and 40 show the cell growth of anti-GDF-8 cells, percent viability of anti-GDF-8 cells, lactate levels, ammonium levels, glutamine levels, anti-GDF-8 titer, and osmolarity, respectively, throughout the course of the experiments under the various experimental conditions.

Among all the conditions tested, only Medium 9 containing 13 mM glutamine and 20 mM asparagine showed significant adverse effects on cell growth and titer. Glutamine is exhausted in all the cultures at approximately the same time, regardless of whether the culture begins with 4 mM or 13 mM glutamine. The highest anti-GDF-8 titer is obtained in cultures that contain 13 mM glutamine and 12 mM asparagine. All culture conditions exhibit decreased lactate and ammonium levels near the end of the culture. Ammonium levels were highest in the culture containing 13 mM glutamine and 20 mM asparagine.

Example 10

The Effect of Asparagine and Cysteine Levels on the Observed Decrease in Lactate and Ammonium Levels in Anti-GDF-8 Cells Cultured in Medium 9.

In Examples 2, 5 and 6, it was found that cultures grown under glutamine starvation conditions exhibit decreased lactate and ammonium levels at the end of the culture process. However, cultures grown in Medium 9 under non-glutamine starvation conditions still exhibit decreased lactate and ammonium levels at the end of the culture process. This effect was not observed in other media such as Medium 1, where glutamine starvation appears necessary for the decreased levels of lactate and ammonium. Medium 9 and Medium 1 differ in the levels of asparagine (20 mM in Medium 9 versus 11 mM total in Medium 1 plus feed) and acidic cystine (1.5 mM in Medium 9 versus 0.95 mM in Medium 1). This example tests whether these two components were responsible for the observed decrease in the lactate and ammonium levels at the end of the culture.

Materials and Methods

Anti-GDF-8 cells were cultured in 1 L BioReactors for 12 days. Cells were initially cultured at 37° C. and were shifted to 31° C. on day 4 or day 5 at 8–10×$10^6$/ml. Table 17 lists the various experimental conditions tested. Samples were taken daily and saved for titer analysis by Protein A HPLC.

TABLE 17

Asparagine and cysteine conditions tested.

| Media | Gln (mM) | Asn (mM) | Total Gln (mM) | Total Asn (mM) | Feed | |
|---|---|---|---|---|---|---|
| Medium 1 | 13 | 5 | 29 | 11 | Medium 5, 30% total | 5 mM Gln, day 4 |
| Medium 1 | 4 | 5 | 4 | 11 | Medium 5-Gln, 30% total | |
| Batch media (Medium 9) | 4 | 20 | 4 | 21 | Medium 5-Gln, 5% day 7 | |

TABLE 17-continued

Asparagine and cysteine conditions tested.

| Media | Gln (mM) | Asn (mM) | Total Gln (mM) | Total Asn (mM) | Feed | |
|---|---|---|---|---|---|---|
| Medium 1 + 5 mM Asn + 0.5 mM Cysteine | 13 | 10 | 29 | 16 | Medium 5, 30% total | 5 mM Gln, day 4 |
| Batch media (Medium 9) | 13 | 20 | 29 | 21 | Medium 5, 30% total | 5 mM Gln, day 4 |

Note:
Medium 5-Gln = Medium 5 lacking glutamine.

Results and Conclusions

Anti-GDF-8 cells grown in Medium 9 exhibited decreased lactate and ammonium levels at the end of the culture process, regardless of whether the cultures were started with 4 mM or 13 mM glutamine (see FIGS. 42 and 43). In contrast, Medium 1 only exhibited decreased lactate and ammonium levels at the end of the culture process when the cultures were started with 4 mM glutamine (see FIGS. 42 and 43). Addition of extra asparagine and cystine to Medium 1 containing 13 mM glutamine did not result in decreased lactate and ammonium levels at the end of the culture process (see FIGS. 42 and 43).

Cultures that exhibited decreased lactate and ammonium levels at the end of the culture process (Medium 1 with 4 mM glutamine, Medium 9 with 4 mM glutamine and Medium 9 with 13 mM glutamine) were also observed to have lower total osmolarity at the end of the culture process (see FIG. 47).

Medium 9 with 4 mM glutamine exhibited the highest anti-GDF-8 titer, followed by Medium 9 with 13 mM glutamine fed on day 4 (see FIG. 46). Taking the effect of dilution of the feed into account, Medium 9 containing 4 mM glutamine had equivalent anti-GDF-8 titer to Medium 9 containing 13 mM glutamine.

Example 11

The Effect of Amino Acid and Vitamin Levels on the Observed Decrease in Lactate and Ammonium Levels in Anti-GDF-8 Cells Cultured in Medium 9.

Example 10 tested whether difference in the asparagine and cysteine levels between Medium 1 and Medium 9 were responsible for the observed decrease in lactate and ammonium levels at the end of the culture process in Medium 9 that was not starved for glutamine. It was determined that these factors were not responsible for the observed decrease. Medium 1 and Medium 9 also differ in their amino acid and vitamin concentrations. This example tests whether differences in amino acids and vitamin concentrations between these two media are responsible for the observed decrease.

Materials and Methods

Anti-GDF-8 cells were cultured in 1 L BioReactors for 12 days. Cells were initially cultured at 37° C. and were shifted to 31° C. on day 4 at $8–10 \times 10^6$/ml. Table 18 lists the various experimental conditions tested. Amino acids, vitamins, hydrocortisone and putrescine, trace elements E (composition listed in Table 19) and iron were added to the various experimental Medium 1 conditions such that the levels of these components were equal to the levels in Medium 9. Samples were taken daily and saved for titer analysis by Protein A HPLC.

TABLE 18

Amino acid and vitamin conditions tested.

| Media | Gln (mM) | Asn (mM) | Feed | Day 5 | Day 7 | Day 10 | Day 11 |
|---|---|---|---|---|---|---|---|
| Medium 1 | 13 | 5 | Medium 5 30% total 5 mM Gln, day 4 | 8% Medium 5 | 12% Medium 5 | 8% Medium 5 | |
| Medium 1 + AA | 13 | 15 | Medium 5 30% total 5 mM Gln, day 4 | 8% Medium 5 | 12% Medium 5 | 8% Medium 5 | |
| Medium 1 + Vit, H/P, E, Fe | 13 | 5 | Medium 5 30% total 5 mM Gln, day 4 | 8% Medium 5 | 12% Medium 5 | 8% Medium 5 | 4 g/L glucose |
| Medium 1 + all | 13 | 15 | Medium 5 30% total 5 mM Gln, day 4 | 8% Medium 5 | 12% Medium 5 | 8% Medium 5 | 4 g/L glucose |
| Medium 9 with 13 mM Gln | 13 | 20 | Medium 5 30% total 5 mM Gln, day 4 | 8% Medium 5 | 12% Medium 5 | 8% Medium 5 | |

Note:
AA = Amino acids,
H/P: = 0.036 mg/mL hydrocortisone, 1.08 mg/mL Putrescine.2HCl,
E: Trace Elements E.

TABLE 19

Composition of Trace Elements E.

| Trace Elements | µg/L | nM |
|---|---|---|
| $(NH_4)_6Mo_7O_{24} \cdot 4H_2O$ | 123.60 | 100.00 |
| $AlCl_3 \cdot 6H_2O$ | 0.48 | 2.00 |
| $H_3BO_3$ | 6.18 | 100.00 |
| $CrCl_3$ | 7.92 | 50.00 |
| $CuSO_4 \cdot 5H_2O$ | 49.94 | 200.00 |
| $GeO_2$ | 0.21 | 2.00 |

TABLE 19-continued

Composition of Trace Elements E.

| Trace Elements | μg/L | nM |
|---|---|---|
| KBr | 0.24 | 2.00 |
| KI | 16.60 | 100.00 |
| LiCl | 0.08 | 2.00 |
| MnSO$_4$.H$_2$O | 16.90 | 100.00 |
| Na$_2$SiO$_3$.9H$_2$O | 142.03 | 500.00 |
| NaF | 0.08 | 2.00 |
| NH$_4$VO$_3$ | 1.17 | 10.00 |
| NiSO$_4$.6H$_2$O | 2.63 | 10.00 |
| RbCl | 0.24 | 2.00 |
| SnCl$_2$.2H$_2$O | 0.45 | 2.00 |
| Sodium Selenite | 34.58 | 200.00 |

Results and Conclusions

All conditions tested exhibited decreased lactate and ammonium levels at the end of the culture process except for Medium 1 containing added amino acids, indicating that increased amino acid levels in Medium 9 compared to Medium 1 are probably not responsible for the decreases in lactate and ammonium levels (see FIGS. 49 and 50). However, Medium 1 containing added vitamins, hydrocortisone and putrescine, trace elements E and iron exhibited lower lactate and ammonium levels at the end of the culture process compared to Medium 1 containing added amino acids (see FIGS. 49 and 50). This indicates that these components may be responsible for the observed decreases in Medium 9.

Cultures grown in Medium 1 containing added vitamins, hydrocortisone and putrescine, trace elements E and iron exhibited the lowest levels of ammonium throughout the experiment due to the lower total amounts of asparagine and glutamine in the starting media (see FIG. 50).

Example 12

The Effect of Vitamin, Trace Elements E and Iron Levels on the Observed Decrease in Lactate and Ammonium Levels in Anti-GDF-8 Cells Cultured in Medium 9

In Example 11, it was determined that the increased levels of vitamins, hydrocortisone and putrescine, trace elements E and iron in Medium 9 relative to Medium 1 might be responsible for the decrease in lactate and ammonium levels observed at the end of the culture process. Here, these components were tested individually and in combination to determine which, if any, were responsible for the observed decrease.

Materials and Methods

Anti-GDF-8 cells were cultured in 1 L BioReactors for 12 days. Cells were initially cultured at 37° C. and were shifted to 31° C. on day 4 at 8–10×10$^6$ cells/ml, with the exception of Medium 1 containing trace E elements, which were shifted on day 4 at about 6×10$^6$ cells/ml. Table 20 lists the various experimental conditions tested. Hydrocortisone and putrescine were added to all Medium 1 conditions such that the levels of these components were equal to the levels in Medium 9. Vitamins, Trace elements E (composition listed in Table 19) and iron were added to the various experimental Medium 1 conditions such that the levels of these components were equal to the levels in Medium 9. Samples were taken daily and saved for titer analysis by Protein A HPLC.

TABLE 20

Amino acid and vitamin conditions tested.

| Media | Gln (mM) | Asn (mM) | Feed | Temp Shift | Day 4 | Day 5 | Day 7 | Day 10 |
|---|---|---|---|---|---|---|---|---|
| Medium 1 + Fe | 13 | 15 | Medium 5 30% total | day 4 | 5 mM Gln, day 4 | 8% Medium 5 | 12% Medium 5 | 8% Medium 5 |
| Medium 1 + E | 13 | 15 | Medium 5 30% total | day 4 | 5 mM Gln, day 4 | 8% Medium 5 | 12% Medium 5 | 8% Medium 5 |
| Medium 1 + Vit | 13 | 15 | Medium 5 30% total | day 4 | 5 mM Gln, day 4 | 8% Medium 5 | 12% Medium 5 | 8% Medium 5 |
| Medium 1 + Fe + E | 13 | 15 | Medium 5 30% total | day 4 | 5 mM Gln, day 4 | 8% Medium 5 | 12% Medium 5 | 8% Medium 5 |
| Medium 1 + Fe + Vit | 13 | 15 | Medium 5 30% total | day 4 | 5 mM Gln, day 4 | 8% Medium 5 | 12% Medium 5 | 8% Medium 5 |
| Medium 1 + E + Vit | 13 | 15 | Medium 5 30% total | day 4 | 5 mM Gln, day 4 | 8% Medium 5 | 12% Medium 5 | 8% Medium 5 |
| Medium 9 with 13 mM Gln | 13 | 20 | Medium 5 30% total | day 4 | 5 mM Gln, day 4 | 8% Medium 5 | 12% Medium 5 | 8% Medium 5 |

Note:
E: Trace Elements E.

Results and Conclusions

Of all the conditions tested, only Medium 9 containing 13 mM glutamine and Medium 1 containing trace elements E exhibited decreased levels of lactate and ammonium at the end of the culture process (see FIGS. 54 and 55). It should be noted that the decreased levels observed for Medium 1 containing trace elements E could be due to the fact that this culture was temperature shifted when the cells were at about 6×10$^6$ cells/mL.

Medium 9 containing 13 mM glutamine exhibited higher anti-GDF-8 titer than any of the Medium 1 formulations.

Example 13

Comparison of Mediums 1, 3 and 9 on Cell Growth and Anti-GDF-8 Titer

This experiment was performed to measure the differences in cell growth and anti-GDF-8 titer using Mediums 1, 3 and 9.

Materials and Methods

Anti-GDF-8 cells were cultured in various media and under feeding conditions as listed in Table 21. Pertinent media information is listed in Table 22. Cells were grown in 1 L Bioreactors for 12 days and were shifted from 37° C. to 31° C. on day 4.

TABLE 21

Media and feed conditions tested.

| Media | Asn | Gln | Feed Day 3 | Day 4 | Day 5 | Day 6 | Day 7 | Day 10 | Day 11 |
|---|---|---|---|---|---|---|---|---|---|
| Medium 3 | 14 mM | 4 mM | 3.3% Medium 5-Gln | 3.3% Medium 5-Gln | 3.3% Medium 5-Gln | 3.3% Medium 5-Gln | 10% Medium 5-Gln | 3.3% Medium 5-Gln | 3.3% Medium 5-Gln |
| Medium 3 | 14 mM | 4 mM | 3.3% Medium 5-Gln | 3.3% Medium 5-Gln | 3.3% Medium 5-Gln | 3.3% Medium 5-Gln | 10% Medium 5-Gln | 3.3% Medium 5-Gln | 3.3% Medium 5-Gln |
| Medium 1 | 14 mM | 4 mM | | | 8% Medium 5-Gln | | 12% Medium 5-Gln | 8% Medium 5-Gln | |
| Medium 9 | 20 mM | 4 mM | | | | 5% Medium 5-Gln | | | |

Note:
Medium 5-Gln - Medium 5 lacking glutamine.

TABLE 22

Media summary.

| Media | Asn | Gln | Feed | AA(Starting)/(Total) | Ion/Total AA |
|---|---|---|---|---|---|
| Medium 3 | 14 mM | 4 mM | 34% Medium 5-Gln | 34 mM/64 mM | 1.75 |
| Medium 9 | 20 mM | 4 mM | 5% Medium 5-Gln | 91.4 mM/94.3 mM | .72 |
| Medium 1 | 14 mM | 4 mM | 31.6% Medium 5-Gln | 78 mM/96.4 mM | .74 |

Note:
Medium 5-Gln - Medium 5 lacking glutamine.

Results and Conclusions

Anti-GDF-8 cells cultured in Medium 9 exhibited the highest cell density and anti-GDF-8 titer, while anti-GDF-8 cells cultured in Medium 3 exhibited the lowest cell density and anti-GDF-8 titer (see FIGS. 57 and 58). The fact that Medium 9 produces superior results than Medium 1 indicates that it is better to provide the media components in the starting media rather than supplying them through multiple feeds. Additionally, the fact that both Medium 1 and Medium 9 perform better than Medium 3 indicates that providing amino acids in concentrations greater than about 70 mM provide superior results than providing amino acids in concentrations less than about 70 mM. Finally, providing amino acids in concentrations greater than about 70 mM in the starting media results in the highest cell densities and titers (compare Medium 9 vs. Medium 1).

Example 14

Statistical Analysis of Optimum Total Glutamine and Asparagine Levels in Medium 9 for Anti-GDF-8 Cell Culture in Bioreactors Materials and Methods Anti-GDF-8 cells were grown in 1 L Bioreactors and were shifted from 37° C. to 31° C. on the days indicated in Table 23. Final titers were subjected to a T-test in order to determine the optimum level of glutamine alone and the optimum level of total combined glutamine and asparagine. Table 23 summarizes some relevant experimental conditions and end results for anti-GDF-8 cells grown in Medium 9.

TABLE 23

Relevant experimental conditions and end results for anti-GDF-8 cells grown in Medium 9.

| Media | Gln (mM) | Asn (mM) | Day Shifted | Feed | Titer (ug/ml) | Titer/1200 | Total Gln | Total Asn | Total Gln + Asn |
|---|---|---|---|---|---|---|---|---|---|
| Medium 9 | 1 | 8 | 6 | 5% Medium 5-Gln | 615.2 | 0.51 | 1 | 9 | 10 |
| Medium 9 | 1 | 8 | 6 | 5% Medium 5-Gln | 857.1 | 0.71 | 4 | 9 | 13 |
| Medium 9 | 1 | 12 | 6 | 5% Medium 5-Gln | 947 | 0.79 | 1 | 13 | 14 |
| Medium 9 | 4 | 12 | 4 | 5% Medium 5-Gln | 1184 | 0.99 | 4 | 13 | 17 |
| Medium 9 | 4 | 20 | 4 | 5% Medium 5-Gln | 769.6 | 0.64 | 1 | 21 | 22 |
| Medium 9 | 4 | 8 | 5 | 5% Medium 5-Gln | 1262.6 | 1.05 | 13 | 9 | 22 |
| Medium 9 | 4 | 20 | 4 | 5% Medium 5-Gln | 1198 | 1.00 | 4 | 21 | 25 |
| Medium 9 | 4 | 20 | 4 | 5% Medium 5-Gln | 1321.1 | 1.10 | 4 | 21 | 25 |
| Medium 9 | 4 | 20 | 4 | 5% Medium 5-Gln | 1162.4 | 0.97 | 4 | 21 | 25 |
| Medium 9 | 13 | 20 | 4 | 5% Medium 5-Gln | 1436.6 | 1.20 | 4 | 21 | 25 |
| Medium 9 | 15 | 12 | 4 | 5% Medium 5-Gln | 1638.6 | 1.37 | 13 | 13 | 26 |
| Medium 9 | 13 | 12 | 4 | 5% Medium 5-Gln | 1606.7 | 1.34 | 13 | 13 | 26 |
| Medium 9 | 13 | 20 | 4 | 5% Medium 5-Gln | 1075.91 | 0.90 | 13 | 21 | 34 |
| Medium 9 | 13 | 20 | 4 | 5% Medium 5-Gln | 1058.4 | 0.88 | 13 | 21 | 34 |

TABLE 23-continued

Relevant experimental conditions and end results for anti-GDF-8 cells grown in Medium 9.

| Media | Gln (mM) | Asn (mM) | Day Shifted | Feed | Titer (ug/ml) | Titer/1200 | Total Gln | Total Asn | Total Gln + Asn |
|---|---|---|---|---|---|---|---|---|---|
| Medium 9 | 13 | 20 | 4 | 5% Medium 5-Gln | 1075.91 | 0.90 | 15 | 21 | 36 |
| Medium 9 | 13 | 5 | 4 | Asn, Gln, 5% Medium 5-Gln | 974.52 | 0.81 | 28.5 | 11 | 39.5 |
| Medium 9 | 13 | 20 | 4 | Asn, Gln, 5% Medium 5-Gln | 831.81 | 0.69 | 28.5 | 26 | 54.5 |
| Medium 9 | 13 | 20 | 4 | Medium 5, 30% total, 5 mM Gln day 4 | 975.4 | 0.81 | 28.5 | 26 | 54.5 |
| Medium 9 | 13 | 20 | 4 | Medium 5, 30% total, 5 mM Gln day 4 | 973.5 | 0.81 | 28.5 | 26 | 54.5 |

Note:
Medium 5-Gln - Medium 5 lacking glutamine.

Results and Conclusions

FIG. 59 shows extrapolated anti-GDF-8 titers for various levels of glutamine alone and total combined glutamine and asparagine. Table 24 shows the results of a T-test comparing normalized titer of glutamine levels between 2 and 15 mM and glutamine levels outside this range. Table 25 shows the results of a T-test comparing normalized titer of combined glutamine and asparagine levels between 16 and 36 mM and combined glutamine and asparagine levels outside this range.

Both T-test results indicated significant differences in anti-GDF-8 titers between the two groups that were compared. Cultures grown in Medium 9 containing between 2 and 15 mM glutamine and between 16 and 36 mM combined glutamine and asparagine exhibited higher anti-GDF-8 titers than cultures grown in media with glutamine and combined glutamine and asparagine levels that fell outside these ranges. In all experiments, asparagine levels were greater than 9 mM.

TABLE 24

T-Test results comparing normalized titer of 2 mM < Gln < 15 mM versus Gln > 15 mM, Gln < 2 mM conditions.

| Normalized Titer | Gln > 15, Gln < 2 | 2 < Gln < 15 |
|---|---|---|
| Mean | 0.724649917 | 1.033147493 |
| Variance | 0.013326655 | 0.036834109 |
| Observations | 7 | 12 |
| Pooled Variance | 0.028537361 | |
| Hypothesized Mean Difference | 0 | |
| df | 17 | |
| t Stat | −3.839791986 | |
| P(T <= t) one-tail | 0.000656219 | |
| t Critical one-tail | 1.739606432 | |
| P(T <= t) two-tail | 0.001312438 | |
| t Critical two-tail | 2.109818524 | |

TABLE 25

T-Test results comparing normalized titer of 16 mM < Gln + Asn < 36 mM versus Gln + Asn > 36 mM, Gln + Asn < 16 mM conditions.

| Normalized Titer | Asn + Gln > 36, Asn + Gln < 16 | 16 < Asn + Gln < 36 |
|---|---|---|
| Mean | 0.735066584 | 1.027071104 |
| Variance | 0.012061148 | 0.041504987 |
| Observations | 7 | 12 |
| Pooled Variance | 0.031113044 | |
| Hypothesized Mean Difference | 0 | |

TABLE 25-continued

T-Test results comparing normalized titer of 16 mM < Gln + Asn < 36 mM versus Gln + Asn > 36 mM, Gln + Asn < 16 mM conditions.

| Normalized Titer | Asn + Gln > 36, Asn + Gln < 16 | 16 < Asn + Gln < 36 |
|---|---|---|
| df | 17 | |
| t Stat | −3.480816823 | |
| P(T <= t) one-tail | 0.001430281 | |
| t Critical one-tail | 1.739606432 | |
| P(T <= t) two-tail | 0.002860561 | |
| t Critical two-tail | 2.109818524 | |

Example 15

Effects of Medium on Cell Culture

This example investigated the performance of three cell culture medium variations at intermediate scale utilizing high density seed cultures. All of the media tested were expected to show improvements over the Phase 1 medium (Medium 10 fed with Medium 11 feed medium), based on small scale bioreactor data.

Materials and Methods

CHO cells expressing a humanized anti-Abeta peptide IgG1 monoclonal antibody ("anti-ABeta cells") were tested in various media, as shown in Table 26 (see Basi et al., Humanized Antibodies that Recognize Beta Amyloid Peptide, WO02/46237). The pH low end set point was 7.0 controlled with 0.95M $Na_2CO_3$+0.05M $K_2CO_3$, except for Phase 1, which was controlled with a solution containing sodium bicarbonate at 0.58 M and sodium carbonate at 0.71 M. Dissolved oxygen was controlled at 30% by sparging on demand with air, agitation was at 60 rpm, and the feed medium was Medium 5 (with or without glutamine, as noted). All cultures were grown at 130L scale except for 03P49B501, which was grown at 500L scale. In brief, Medium 1 is enriched in all nutrients, without consideration for relative uptake rates, while Medium 12 was balanced by removing apparently unnecessary nutrients from the indiscriminately enriched version. The compositions of Mediums 10, 11 and 12 are listed in Table 7.

TABLE 26

Initial medium, feed quantities and seed sources for Pilot runs.

| Batch No. | Description | Initial Medium | Amount Fed | Gln fed? | Seed Source | Seed Density (Viables/mL) |
|---|---|---|---|---|---|---|
| 1 | Phase 1 | Medium 10 | 38%* | Yes | Wave bags | $0.2 \times 10^6$ |
| 2 | Rich Medium, High Gln (1) | Medium 1 | 16% | Yes | Wave bags | $0.2 \times 10^6$ |
| 3 | Rich Med, High Gln (2) | Medium 1 | 16% | Yes | Wave bags | $0.2 \times 10^6$ |
| 4 | Rich Med, Lower Gln | Medium 1 | 15% | No | Wave bags | $0.2 \times 10^6$ |
| 5 | Balanced Med, Low Gln (1) | Medium 12 | 10% | No | Wave bags | $0.2 \times 10^6$ |
| 6 | Bal Med, Low Gln (2) | Medium 12 | 9% | No | Wave bags | $0.2 \times 10^6$ |
| 7 | Bal Med, Low Gln, Dense Seed | Medium 12 | 5% | No | High density Bioreactor | $2.0 \times 10^6$ |

*The Phase 1 process was fed with Medium 12, which is not as rich as Medium 5.

TABLE 27

Compositions of Mediums 10, 11 and 12.

| | Medium 10 | | Medium 11 | | Medium 12 | |
|---|---|---|---|---|---|---|
| Amino Acids | mg/L | mM | mg/L | mM | mg/L | mM |
| alanine | 24.87 | 0.28 | 142.48 | 1.60 | 17.80 | 0.20 |
| arginine | 423.43 | 2.43 | 1528.84 | 8.79 | 696.00 | 4.00 |
| asparagine.H$_2$O | 173.90 | 1.16 | 1080.60 | 7.20 | 1500.00 | 10.00 |
| aspartic acid | 52.72 | 0.40 | 532.40 | 4.00 | 219.45 | 1.65 |
| cysteine.HCl.H$_2$O | 70.01 | 0.40 | | | 70.40 | 0.40 |
| cysteine.2HCl | 62.09 | 0.20 | 470.00 | 1.50 | 312.50 | 1.00 |
| glutamic acid | 41.08 | 0.28 | 235.38 | 1.60 | | |
| monosodium glutamate | | | | | 33.80 | 0.20 |
| glutamine | 1162.40 | 7.96 | 6000.00 | 41.10 | 584.00 | 4.00 |
| glycine | 35.92 | 0.48 | 120.07 | 1.60 | 115.50 | 1.54 |
| histidine.HCl.H$_2$O | 75.27 | 0.36 | 588.32 | 2.80 | 369.60 | 1.76 |
| isoleucine | 151.90 | 1.16 | 944.52 | 7.21 | 370.73 | 2.83 |
| leucine | 172.69 | 1.32 | 1360.75 | 10.39 | 615.70 | 4.70 |
| lysine.HCl | 218.38 | 1.20 | 1456.80 | 8.00 | 946.40 | 5.20 |
| methionine | 53.55 | 0.36 | 477.06 | 3.20 | 387.40 | 2.60 |
| phenylalanine | 98.81 | 0.60 | 660.36 | 4.00 | 363.00 | 2.20 |
| proline | 96.40 | 0.84 | 552.31 | 4.80 | 471.50 | 4.10 |
| serine | 273.07 | 2.60 | 1264.70 | 12.04 | 903.00 | 8.60 |
| threonine | 132.81 | 1.12 | 762.02 | 6.40 | 380.80 | 3.20 |
| tryptophan | 28.99 | 0.14 | 260.94 | 1.28 | 212.16 | 1.04 |
| tyrosine.2Na.2H$_2$O | 145.10 | 0.56 | 832.62 | 3.19 | 456.75 | 1.75 |
| valine | 131.17 | 1.12 | 749.21 | 6.40 | 468.00 | 4.00 |
| Vitamins | mg/L | μM | mg/L | μM | mg/L | μM |
| biotin | 0.36 | 1.49 | 3.28 | 13.45 | 2.68 | 11.00 |
| calcium pantothenate | 4.03 | 8.47 | 36.02 | 75.67 | 21.93 | 46.06 |
| choline chloride | 16.11 | 115.92 | 143.28 | 1030 | 116.76 | 840.00 |
| folic acid | 4.76 | 10.80 | 42.43 | 96.22 | 25.93 | 58.80 |
| inositol | 22.64 | 125.79 | 201.71 | 1120 | 163.98 | 911.00 |
| nicotinamide | 3.61 | 29.62 | 32.02 | 262.44 | 26.23 | 215.00 |
| pyridoxal.HCl | 1.99 | 9.83 | | | 2.03 | 10.00 |
| pyridoxine.HCl | 1.67 | 8.10 | 32.82 | 159.31 | 18.13 | 88.00 |
| riboflavin | 0.40 | 1.06 | 3.60 | 9.58 | 0.41 | 1.10 |
| thiamine.HCl | 3.92 | 11.64 | 35.22 | 104.51 | 39.43 | 117.00 |
| vitamin B12 | 1.34 | 0.99 | 11.21 | 8.27 | 10.57 | 7.80 |
| Inorganic Salts | mg/L | mM | mg/L | mM | mg/L | mM |
| CaCl$_2$ | 115.78 | 1.04 | 113.27 | 1.02 | 116.55 | 1.05 |
| KCl | 310.94 | 4.17 | | | 312.90 | 4.19 |
| KH$_2$PO$_4$ | | | 1640.00 | 12.06 | | |
| Na$_2$HPO$_4$ | 70.81 | 0.50 | | | 56.60 | 0.40 |
| NaCl | 3704.96 | 63.44 | | | | |
| NaH$_2$PO$_4$.H$_2$O | 114.53 | 0.83 | | | 645.84 | 4.68 |
| MgSO$_4$ | 48.70 | 0.41 | | | 138.00 | 1.15 |

TABLE 27-continued

Compositions of Mediums 10, 11 and 12.

|  | Medium 10 | | Medium 11 | | Medium 12 | |
| --- | --- | --- | --- | --- | --- | --- |
| MgSO$_4$.7H$_2$O | 8.60 | 0.03 | 170.00 | 0.69 | | |
| MgCl$_2$ | 28.53 | 0.30 | | | 28.50 | 0.30 |
| NaHCO$_3$ | 1220.00 | 14.52 | | | 2000.00 | 23.81 |
| Trace Elements | µg/L | nM | µg/L | nM | µg/L | nM |
| Sodium Selenite | 7.00 | 40.49 | 40.00 | 231.35 | 53.65 | 310.27 |
| Fe(NO$_3$)$_3$.9H$_2$O | 49.86 | 123.42 | | | 50.00 | 123.76 |
| CuSO$_4$ | 0.97 | 6.06 | 3.44 | 21.51 | 10.00 | 62.50 |
| CuSO$_4$.5H$_2$O | 7.49 | 30.00 | 7.49 | 30.00 | 49.94 | 200.00 |
| FeSO$_4$.7H$_2$O | 1542 | 5549 | 2534 | 9115 | 3366 | 12000 |
| ZnSO$_4$.7H$_2$O | 1383 | 4821 | 2704 | 9421 | 2640 | 9198 |
| MnSO$_4$.H$_2$O | 0.17 | 1.01 | 0.17 | 1.01 | 16.90 | 100.00 |
| Na$_2$SiO$_3$.9H$_2$O | 140 | 492.84 | 140.00 | 492.84 | 142.03 | 500.00 |
| (NH$_4$)$_6$Mo$_7$O$_{24}$.4H$_2$O | 1.24 | 1.00 | 1.24 | 1.00 | 123.60 | 100.00 |
| NH$_4$VO$_3$ | 0.65 | 5.56 | 0.65 | 5.56 | 1.17 | 10.00 |
| NiSO$_4$.6H$_2$O | 0.13 | 0.49 | 0.13 | 0.49 | 2.63 | 10.00 |
| SnCl$_2$.2H$_2$O | 0.12 | 0.53 | 0.12 | 0.53 | 0.45 | 2.00 |
| AlCl$_3$.6H$_2$O | | | 1.20 | 4.97 | 0.48 | 2.00 |
| AgNO$_3$ | | | 0.17 | 1.00 | | |
| Ba(C$_2$H$_3$O$_2$)$_2$ | | | 2.55 | 9.98 | | |
| KBr | | | .12 | 1.01 | 0.24 | 2.00 |
| CdCl$_2$.2.5H$_2$O | | | 2.28 | 9.99 | | |
| CoCl$_2$.6H$_2$O | | | 2.38 | 10.00 | | |
| CrCl$_3$ | | | 0.32 | 2.02 | 7.92 | 50.00 |
| NaF | | | 4.20 | 100.02 | 0.08 | 2.00 |
| GeO$_2$ | | | 0.53 | 5.07 | 0.21 | 2.00 |
| KI | | | 0.17 | 1.02 | 16.60 | 100 |
| RbCl | | | 1.21 | 10.01 | 0.24 | 2.00 |
| ZrOCl$_2$.8H$_2$O | | | 3.22 | 9.99 | | |
| H3BO$_3$ | | | | | 6.18 | 100.00 |
| LiCl | | | | | 0.08 | 2.00 |
| Other Components | µg/L | µM | µg/L | µM | µg/L | µM |
| Hydrocortisone | 86.40 | .24 | 288.00 | 0.79 | 360.00 | 0.99 |
| Putrescine.2HCl | 2480 | 15.39 | 8000 | 49.66 | 10000 | 62.07 |
| linoleic acid | 56.69 | 0.20 | 336.25 | 1.20 | 290.00 | 1.04 |
| thioctic acid | 141.71 | 0.69 | 840.63 | 4.08 | 716.00 | 3.48 |
| Other Components | mg/L | mM | mg/L | mM | mg/L | mM |
| D-glucose (Dextrose) | 11042.24 | 61.35 | 43005.99 | 238.92 | 15000.00 | 83.33 |
| PVA | 2520.00 | | 2400.00 | | 2560.00 | |
| Nucellin ™ | 14.00 | | 80.00 | | 50.00 | |
| Sodium Pyruvate | 54.85 | 0.50 | | | 55.00 | 0.50 |

Results and Conclusions

Media changes led to steady improvement through the course of these experiments. In terms of cell growth, viability, reduced lactate levels, reduced ammonium levels, and titer, reduced glutamine levels were better than elevated ones (see FIGS. 60-64) and balanced (batch) medium was better than rich medium (Medium 1, see FIGS. 60-64). Cultures started from high density inoculum exhibited higher final titer than did cultures started from lower density inoculums (see FIG. 64).

Unlike what was observed in small scale bioreactors, the first medium (Medium 1 with high Gln) resulted in lower titers than did the original process (see FIG. 64). There also was no shift to lactate uptake after the temperature change (see FIG. 62). This suggests that there may be some scale sensitivity with this medium. This conclusion is supported by small-scale (2L) parallel runs that were done along with these intermediate scale experiments (data not shown). The later medium formulations containing less glutamine were not sensitive to scale, at least in these experiments (see FIGS. 60-65). The duplicated processes (Batches 2 and 3 and Batches 5 and 6) show very good run-to-run reproducibility (see FIGS. 60-65), increasing the confidence in all of the data gathered in this campaign.

Example 16

Production of TNFR-Ig Using Medium 9

Materials and Methods

CHO cells expressing a dimeric fusion protein consisting of the extracellular ligand-binding portion of the human 75 kilodalton (p75) tumor necrosis factor receptor (TNFR) linked to the Fc portion of IgG1 ("TNFR-Ig cells") were seeded at high density from a perfusion bioreactor and diluted to $3\times10^6$ viable cells/ml in Medium 9 for the production bioreactor step.

Results and Conclusions

FIGS. 66, 67, 68, 69, 70, 71 and 72 show cell growth, cell viability, residual glucose, glutamine levels, lactate concentration, ammonium concentration, and relative product titer, respectively. Under the range of minor modifications to the process, all conditions yielded good cell growth, high cellular viability, and high overall final titer.

For all the conditions of this experiment, the metabolic inhibitory byproduct lactate was either consumed, or the concentration plateaued, suggesting that lactate production was arrested. Similarly, for the inhibitory metabolite ammonium, levels rose initially, but at some time after the temperature shift the ammonium started to be consumed by the cells. In this Example, the TNFR-Ig cell cultures were subjected to the chemical inductants sodium butyrate, and HMBA.

Example 17

Comparison of Large and Small-Scale Culture Conditions

Materials and Methods

To determine whether the size of the culture affected relevant culture characteristics, anti-GDF-8 cells were grown in either small-scale 1 liter bioreactors or large-scale 6000 liter bioreactors. Cells were grown at 37° C. and shifted to 31° C. on day 4.

Results and Conclusions

As can be seen in FIGS. 73, 74, 75 and 76 (which show cell density, titer, lactate levels and ammonium levels, respectively), there were no relevant differences between the 6000 liter large-scale and I liter small-scale cultures for these characteristics. Both lactate and ammonium levels began to decrease after the temperature shift on day 4. This example demonstrates that the size of the culture does not affect cell density, cell viability, lactate levels and ammonium levels when the cultures are subjected to the same growth conditions.

What is claimed is:

1. A method of producing TNFR-Ig in a large-scale production cell culture comprising the steps of:
providing a cell culture comprising;
mammalian cells that contain a gene encoding TNFR-Ig, which gene is expressed under condition of cell culture; and
a medium containing glutamine and having a medium characteristic selected from the group consisting of: (i) a cumulative amino acid amount per unit volume greater than 70 mM, (ii) a molar cumulative glutamine to cumulative asparagine ratio of less than 2, (iii) a molar cumulative glutamine to cumulative total amino acid ratio of less than 0.2, (iv) a molar cumulative inorganic ion to cumulative total amino acid ratio between about 0.4 to 1, (v) a combined cumulative amount of glutamine and asparagine per unit volume of greater than 16 mM, and combinations thereof;
maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;
changing at least one of the culture conditions, so that a second set of culture conditions is applied;
maintaining said culture for a second period of time under the second set of conditions and for a second period of time so that TNFR-Ig accumulates in the cell culture.

2. A method of producing TNFR-Ig in a large-scale production cell culture comprising the steps of:
providing a cell culture comprising;
mammalian cells that contain a gene encoding TNFR-Ig, which gene is expressed under condition of cell culture; and
a medium containing a cumulative amino acid amount per unit volume greater than 70 mM; and
said medium containing glutamine; and said medium having two medium characteristics selected from the group consisting of: (i) a molar cumulative glutamine to cumulative asparagine ratio of less than 2, (ii) a molar cumulative glutamine to cumulative total amino acid ratio of less than 0.2, (iii) a molar cumulative inorganic ion to cumulative total amino acid ratio between about 0.4 to 1, (iv) a combined cumulative amount of glutamine and asparagine per unit volume of greater than 16 mM, and combinations thereof;
maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;
changing at least one of the culture conditions, so that a second set of culture conditions is applied;
maintaining said culture for a second period of time under the second set of conditions and for a second period of time so that TNFR-Ig accumulates in the cell culture.

3. A method of producing TNFR-Ig in a large-scale production cell culture comprising the steps of:
providing a cell culture comprising;
mammalian cells that contain a gene encoding TNFR-Ig, which gene is expressed under condition of cell culture; and
a medium containing a molar cumulative glutamine to cumulative asparagine ratio of less than 2; and
said medium containing glutamine; and said medium having two medium characteristics selected from the group consisting of: (i) a medium containing a cumulative amino acid amount per unit volume greater than 70 mM, (ii) a molar cumulative glutamine to cumulative total amino acid ratio of less than 0.2, (iii) a molar cumulative inorganic ion to cumulative total amino acid ratio between about 0.4 to 1, (iv) a combined cumulative amount of glutamine and asparagine per unit volume of greater than 16 mM, and combinations thereof;
maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;
changing at least one of the culture conditions, so that a second set of culture conditions is applied;
maintaining said culture for a second period of time under the second set of conditions and for a second period of time so that TNFR-Ig accumulates in the cell culture.

4. A method of producing TNFR-Ig in a large-scale production cell culture comprising the steps of:
providing a cell culture comprising;

mammalian cells that contain a gene encoding TNFR-Ig, which gene is expressed under condition of cell culture; and a medium containing a molar cumulative glutamine to cumulative total amino acid ratio of less than 0.2; and said medium containing glutamine; and said medium having two medium characteristics selected from the group consisting of: (i) a medium containing a cumulative amino acid amount per unit volume greater than 70 mM, (ii) a molar cumulative glutamine to cumulative asparagine ratio of less than 2, (iii) a molar cumulative inorganic ion to cumulative total amino acid ratio between about 0.4 to 1, (iv) a combined cumulative amount of glutamine and asparagine per unit volume of greater than 16 mM, and combinations thereof;

maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;

changing at least one of the culture conditions, so that a second set of culture conditions is applied;

maintaining said culture for a second period of time under the second set of conditions and for a second period of time so that TNFR-Ig accumulates in the cell culture.

5. A method of producing TNFR-Ig in a large-scale production cell culture comprising the steps of:

providing a cell culture comprising;

mammalian cells that contain a gene encoding TNFR-Ig, which gene is expressed under condition of cell culture; and a medium containing a molar cumulative inorganic ion to cumulative total amino acid ratio between about 0.4 to 1; and said medium containing glutamine; and said medium having two medium characteristics selected from the group consisting of: (i) a medium containing a cumulative amino acid amount per unit volume greater than 70 mM, (ii) a molar cumulative glutamine to cumulative asparagine ratio of less than 2, (iii) a molar cumulative glutamine to cumulative total amino acid ratio of less than 0.2, (iv) a combined cumulative amount of glutamine and asparagine per unit volume of greater than 16 mM, and combinations thereof;

maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;

changing at least one of the culture conditions, so that a second set of culture conditions is applied;

maintaining said culture for a second period of time under the second set of conditions and for a second period of time so that TNFR-Ig accumulates in the cell culture.

6. A method of producing TNFR-Ig in a large-scale production cell culture comprising the steps of:

providing a cell culture comprising;

mammalian cells that contain a gene encoding TNFR-Ig, which gene is expressed under condition of cell culture; and a medium containing a combined cumulative amount of glutamine and asparagine per unit volume of greater than 16 mM; and said medium containing glutamine; and said medium having two medium characteristics selected from the group consisting of: (i) a medium containing a cumulative amino acid amount per unit volume greater 70 mM, (ii) a molar cumulative glutamine to cumulative asparagine ratio of less than 2, (iii) a molar cumulative glutamine to cumulative total amino acid ratio of less than 0.2, (iv) a molar cumulative inorganic ion to cumulative total amino acid ratio between about 0.4 to 1, and combinations thereof;

maintaining said culture in an initial growth phase under a first set of culture conditions for a first period of time sufficient to allow said cells to reproduce to a viable cell density within a range of about 20%-80% of the maximal possible viable cell density if said culture were maintained under the first set of culture conditions;

changing at least one of the culture conditions, so that a second set of culture conditions is applied;

maintaining said culture for a second period of time under the second set of conditions and for a second period of time so that TNFR-Ig accumulates in the cell culture.

7. The method of claim 1, wherein said cell culture condition in said changing at least one of the culture conditions step is selected from the group consisting of: (i) temperature, (ii) pH, (iii) osmolality, (iv) chemical inductant level, and combinations thereof.

8. The method of claim 1, wherein the initial glutamine concentration of said medium is less than or equal to 13 mM.

9. The method of claim 1, wherein the initial glutamine concentration of said medium is less than or equal to 10 mM.

10. The method of claim 1, wherein the initial glutamine concentration of said medium is less than or equal to 7 mM.

11. The method of claim 1, wherein the initial glutamine concentration of said medium is less than or equal to 4 mM.

12. The method of claim 1, wherein the total cumulative amount per unit volume of glutamine of said medium is less than or equal to 13 mM.

13. The method of claim 1, wherein the total cumulative amount per unit volume of glutamine of said medium is less than or equal to 10 mM.

14. The method of claim 1, wherein the total cumulative amount per unit volume of glutamine of said medium is less than or equal to 7 mM.

15. The method of claim 1, wherein the total cumulative amount per unit volume of glutamine of said medium is less than or equal to 4 mM.

16. The method of claim 1, wherein glutamine is only provided in the initial medium at the beginning of the cell culture.

17. The method of claim 1, wherein the concentration of soluble iron in the media is greater than 5 μM.

18. The method of claim 1, wherein viable cell density of said culture is measured on a periodic basis.

19. The method of claim 1, wherein viability of said culture is measured on a periodic basis.

20. The method of claim 1, wherein said lactate levels of said culture is measured on a periodic basis.

21. The method of claim 1, wherein said ammonium levels of said culture is measured on a periodic basis.

22. The method of claim 1, wherein said titer of said culture is measured on a periodic basis.

23. The method of claim 1, wherein osmolarity of said culture is measured on a periodic basis.

24. The method of any one of claims 18-23, wherein said measurements are taken daily.

25. The method of claim 1, wherein the initial density of said mammalian cells is at least 2×102 cells/mL.

26. The method of claim 1, wherein the initial density of said mammalian cells is at least 2×103 cells/mL.

27. The method of claim 1, wherein the initial density of said mammalian cells is at least 2×104 cells/mL.

28. The method of claim 1, wherein the initial density of said mammalian cells is at least 2×105 cells/mL.

29. The method of claim 1, wherein the initial density of said mammalian cells is at least 2×106 cells/mL.

30. The method of claim 1, wherein the initial density of said mammalian cells is at least 5×106 cells/mL.

31. The method of claim 1, wherein the initial density of said mammalian cells is at least 10×106 cells/mL.

32. The method of claim 1, wherein the step of providing comprises providing at least 1000 L of a culture.

33. The method of claim 1, wherein the step of providing comprises providing at least 2500 L of a culture.

34. The method of claim 1, wherein the step of providing comprises providing at least 5000 L of a culture.

35. The method of claim 1, wherein the step of providing comprises providing at least 8000 L of a culture.

36. The method of claim 1, wherein the step of providing comprises providing at least 10,000 L of a culture.

37. The method of claim 1, wherein the step of providing comprises providing at least 12,000 L of a culture.

38. The method of claim 1, wherein said first set of conditions comprises a first temperature range that is approximately 30 to 42 degrees Celsius.

39. The method of claim 1, wherein said first set of conditions comprises a first temperature range that is approximately 32 to 40 degrees Celsius.

40. The method of claim 1, wherein said first set of conditions comprises a first temperature range that is approximately 34 to 38 degrees Celsius.

41. The method of claim 1, wherein said first set of conditions comprises a first temperature range that is approximately 36 to 37 degrees Celsius.

42. The method of claim 1, wherein said first set of conditions comprises a first temperature range that is approximately 37 degrees Celsius.

43. The method of claim 1, wherein said second set of conditions comprises a second temperature range that is approximately 25 to 41 degrees Celsius.

44. The method of claim 1, wherein said second set of conditions comprises a second temperature range that is approximately 27 to 38 degrees Celsius.

45. The method of claim 1, wherein said second set of conditions comprises a second temperature range that is approximately 29 to 35 degrees Celsius.

46. The method of claim 1, wherein said second set of conditions comprises a second temperature range that is approximately 29 to 33 degrees Celsius.

47. The method of claim 1, wherein said second set of conditions comprises a second temperature range that is approximately 30 to 32 degrees Celsius.

48. The method of claim 1, wherein said second set of conditions comprises a second temperature range that is approximately 31 degrees Celsius.

49. The method of claim 1, further comprising a second changing step subsequent to first said changing at least one of the culture conditions comprising changing at least one of the culture conditions, so that a third set of conditions is applied to the culture.

50. The method of claim 49, wherein the second changing step comprises changing at least one culture condition selected from the group consisting of: (i) temperature, (ii) pH, (iii) osmolality, (iv) chemical inductant level, and combinations thereof.

51. The method of claim 49, wherein said third set of conditions comprises a third temperature range that is approximately 25 to 40 degrees Celsius.

52. The method of claim 49, wherein said third set of conditions comprises a third temperature range that is approximately 27 to 37 degrees Celsius.

53. The method of claim 49, wherein said third set of conditions comprises a third temperature range that is approximately 29 to 34 degrees Celsius.

54. The method of claim 49, wherein said third set of conditions comprises a third temperature range that is approximately 30 to 32 degrees Celsius.

55. The method of claim 1, wherein said first period of time is between 0-8 days.

56. The method of claim 1, wherein said first period of time is between 1-7 days.

57. The method of claim 1, wherein said first period of time is between 2-6 days.

58. The method of claim 1, wherein said first period of time is between 3-5 days.

59. The method of claim 1, wherein said first period of time is approximately 4 days.

60. The method of claim 1, wherein said first period of time is approximately 5 days.

61. The method of claim 1, wherein said first period of time is approximately 6 days.

62. The method of claim 1, wherein the total of said first period of time and said second period of time is at least 5 days.

63. The method of claim 1, wherein in the step of maintaining said culture for a second period of time, the lactate level decreases subsequent to the lactate level in the culture reaching a maximal level.

64. The method of claim 1, wherein in the step of maintaining said culture for a second period of time, the ammonium level decreases subsequent to the ammonium level in the culture reaching a maximal level.

65. The method of claim 1, wherein said total amount of said produced TNFR-Ig is at least 1.5-fold higher that the amount of TNFR-Ig produced under otherwise identical conditions in otherwise identical medium that lacks said medium characteristic.

66. The method of claim 1, wherein said total amount of said produced TNFR-Ig is at least 2-fold higher that the amount of TNFR-Ig produced under otherwise identical conditions in otherwise identical medium that lacks said medium characteristic.

67. The method of claim 1, wherein said cell culture is further provided with supplementary components.

68. The method of claim 67, wherein said supplementary components are provided at multiple intervals.

69. The method of claim 67 wherein said supplementary components are selected from a group consisting of hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

70. A method of producing TNFR-Ig in a large-scale production cell culture comprising steps of;
  providing a cell culture comprising;
    mammalian cells that contain a gene encoding TNFR-Ig, which gene is expressed under condition of cell culture; and
    a defined medium containing glutamine and having at least two medium characteristics selected from the group consisting of: i) a starting amino acid concentration greater than 70 mM, ii) a molar glutamine to asparagine ratio of less than 2, iii) a molar glutamine to total amino acid ratio of less than 0.2, iv) a molar inorganic ion to total amino acid ratio between about 0.4 to 1, and v) a combined glutamine and asparagine concentration greater than 16 mM;
  maintaining said culture in an initial growth phase under a first set of culture conditions for a first period of time sufficient to allow said cells to reproduce within a range of about 20%-80% of the maximal possible viable cell density if said culture were maintained under the first set of culture conditions;
  changing at least one of the culture conditions, so that a second set of culture conditions is applied;
  maintaining said culture for a second period of time under the second set of conditions and for a second period of time so that TNFR-Ig accumulates in the cell culture.

71. A method of producing TNFR-Ig in a large-scale production cell culture comprising steps of;
  providing a cell culture comprising;
    mammalian cells that contain a gene encoding TNFR-Ig, which gene is expressed under condition of cell culture; and
    a defined medium containing glutamine and having at least three medium characteristic selected from the group consisting of: i) a starting amino acid concentration greater than 70 mM, ii) a molar glutamine to asparagine ratio of less than 2, iii) a molar glutamine to total amino acid ratio of less than 0.2, iv) a molar inorganic ion to total amino acid ratio between about 0.4 to 1, and v) a combined glutamine and asparagine concentration greater than 16 mM;
  maintaining said culture in an initial growth phase under a first set of culture conditions for a first period of time sufficient to allow said cells to reproduce within a range of about 20%-80% of the maximal possible viable cell density if said culture were maintained under the first set of culture conditions;
  changing at least one of the culture conditions, so that a second set of culture conditions is applied;
  maintaining said culture for a second period of time under the second set of conditions and for a second period of time so that TNFR-Ig accumulates in the cell culture.

72. A method of producing TNFR-Ig in a large-scale production cell culture comprising steps of;
  providing a cell culture comprising;
    mammalian cells that contain a gene encoding TNFR-Ig, which gene is expressed under condition of cell culture; and
    a defined medium containing glutamine and having at least four medium characteristic selected from the group consisting of: i) a starting amino acid concentration greater than 70 mM, ii) a molar glutamine to asparagine ratio of less than 2, iii) a molar glutamine to total amino acid ratio of less than 0.2, iv) a molar inorganic ion to total amino acid ratio between about 0.4 to 1, and v) a combined glutamine and asparagine concentration greater than 16 mM;
  maintaining said culture in an initial growth phase under a first set of culture conditions for a first period of time sufficient to allow said cells to reproduce within a range of about 20%-80% of the maximal possible viable cell density if said culture were maintained under the first set of culture conditions;
  changing at least one of the culture conditions, so that a second set of culture conditions is applied;
  maintaining said culture for a second period of time under the second set of conditions and for a second period of time so that TNFR-Ig accumulates in the cell culture.

73. A method of producing TNFR-Ig in a large-scale production cell culture comprising steps of;
  providing a cell culture comprising;
    mammalian cells that contain a gene encoding TNFR-Ig, which gene is expressed under condition of cell culture; and
    a defined medium containing glutamine, characterized by: i) a starting amino acid concentration greater than 70 mM, ii) a molar glutamine to asparagine ratio of less than 2, iii) a molar glutamine to total amino acid ratio of less than 0.2, iv) a molar inorganic ion to total amino acid ratio between about 0.4 to 1, and v) a combined glutamine and asparagine concentration greater than 16 mM;
  maintaining said culture in an initial growth phase under a first set of culture conditions for a first period of time sufficient to allow said cells to reproduce within a range of about 20%-80% of the maximal possible viable cell density if said culture were maintained under the first set of culture conditions;
  changing at least one of the culture conditions, so that a second set of culture conditions is applied;
  maintaining said culture for a second period of time under the second set of conditions and for a second period of time so that TNFR-Ig accumulates in the cell culture.

74. A method of producing TNFR-Ig in a large-scale production cell culture comprising the steps of:
  providing a cell culture comprising;
    mammalian cells that contain a gene encoding TNFR-Ig, which gene is expressed under condition of cell culture; and
    a medium containing glutamine and having a combined cumulative amount of glutamine and asparagine per unit volume of greater than 16 mM;
  maintaining said culture in an initial growth phase under a first set of culture conditions for a first period of time sufficient to allow said cells to reproduce within a range of about 20%-80% of the maximal possible viable cell density if said culture were maintained under the first set of culture conditions;
  changing at least one of the culture conditions, so that a second set of culture conditions is applied;
  maintaining said culture for a second period of time under the second set of conditions and for a second period of time so that TNFR-Ig accumulates in the cell culture.

75. The method of claim 1, wherein said medium comprises a medium containing glutamine and having a medium characteristic selected from the group consisting of:
  (i) a starting amino acid concentration greater than 70 mM, (ii) a molar starting glutamine to starting asparagine ratio of less than about 2, (iii) a molar starting glutamine to starting total amino acid ratio of less than 0.2, (iv) a molar starting inorganic ion to starting total amino acid ratio between about 0.4 to 1, (v) a combined starting glutamine and starting asparagine concentration greater than about 16 mM, and combinations thereof.

76. The method of any one of claims 1-6 or 70-75, wherein:
lactate levels are lower than those levels observed under otherwise identical conditions in otherwise identical medium that lacks said medium characteristic;
ammonium levels are lower than those levels observed under otherwise identical conditions in otherwise identical medium that lacks said medium characteristic; and
total amount of produced TNFR-Ig is at least as high as that observed under otherwise identical conditions in otherwise identical medium that lacks said medium characteristic.

77. The method of claim 1, wherein said culture is not supplemented with additional components over the course of producing said TNFR-Ig.

78. The method of claim 1, wherein said culture is not supplemented with additional glutamine over the course of producing said TNFR-Ig.

79. The method of claim 1, wherein the glutamine concentration in said culture is substantially depleted prior to said step of changing to a second set of culture conditions.

80. The method of claim 1, wherein the glutamine concentration in said culture is substantially depleted at approximately the same time as said step of changing to a second set of culture conditions.

81. The method of claim 1, wherein glycylglutamine is substituted for glutamine in said culture.

82. The method of claim 1, wherein said medium contains: (i) a cumulative amino acid amount per unit volume greater than 70 mM, (ii) a molar cumulative glutamine to cumulative asparagine ratio of less than 2, (iii) a molar cumulative glutamine to cumulative total amino acid ratio of less than about 0.2, (iv) a molar cumulative inorganic ion to cumulative total amino acid ratio between about 0.4 to 1, and (v) a combined cumulative amount of glutamine and asparagine per unit volume greater than 16 mM.

83. The method of claim 1, wherein said medium contains: (i) a cumulative amino acid amount per unit volume greater than 70 mM, (ii) a molar cumulative glutamine to cumulative total amino acid ratio of less than 0.2, (iii) a molar cumulative inorganic ion to cumulative total amino acid ratio between about 0.4 to 1, and (iv) a combined cumulative amount of glutamine and asparagine per unit volume greater than 16 a mM.

84. The method of claim 1, wherein the cumulative total amount of histidine, isoleucine, leucine, methionine, phenylalanine, proline, tryptophan, tyrosine, and proline per unit volume in said medium is greater than 25 mM.

85. The method of claim 1, wherein the cumulative total amount of histidine, isoleucine, leucine, methionine, phenylalanine, proline, tryptophan, tyrosine, and proline per unit volume in said medium is greater than 35 mM.

86. The method of claim 1, wherein the initial total amount of histidine, isoleucine, leucine, methionine, phenylalanine, proline, tryptophan, tyrosine, and proline per unit volume in said medium is greater than 25 mM.

87. The method of claim 1, wherein the initial total amount of histidine, isoleucine, leucine, methionine, phenylalanine, proline, tryptophan, tyrosine, and proline per unit volume in said medium is greater than 35 mM.

88. The method of claim 1, wherein said medium has a medium characteristic selected from the group consisting of:
(i) a cumulative total amount of histidine per unit volume greater than 1.7 mM;
(ii) a cumulative total amount of isoleucine per unit volume greater than 3.5 mM;
(iii) a cumulative total amount of leucine per unit volume greater than 5.5 mM;
(iv) a cumulative total amount of methionine per unit volume greater than 2.0 mM;
(v) a cumulative total amount of phenylalanine per unit volume greater than 2.5 mM;
(vi) a cumulative total amount of proline per unit volume greater than 2.5 mM;
(vii) a cumulative total amount of tryptophan per unit volume greater than 1.0 mM;
(viii) a cumulative total amount of tyrosine per unit volume greater than 2.0 mM; and
(ix) a cumulative total amount of proline per unit volume greater than 2.5 mM.

89. The method of claim 1, wherein said medium has a medium characteristic selected from the group consisting of:
(i) an initial amount of histidine per unit volume greater than 1.7 mM;
(ii) an initial amount of isoleucine per unit volume greater than 3.5 mM;
(iii) an initial amount of leucine per unit volume greater than 5.5 mM;
(iv) an initial amount of methionine per unit volume greater than 2.0 mM;
(v) an initial amount of phenylalanine per unit volume greater than 2.5 mM;
(vi) an initial amount of proline per unit volume greater than 2.5 mM;
(vii) an initial amount of tryptophan per unit volume greater than 1.0 mM;
(viii) an initial amount of tyrosine per unit volume greater than 2.0 mM; and
(ix) an initial amount of proline per unit volume greater than 2.5 mM.

90. The method of claim 1, wherein the cumulative total amount of serine per unit volume in said medium is greater than 7 mM.

91. The method of claim 1, wherein the cumulative total amount of serine per unit volume in said medium is greater than 10 mM.

92. The method of claim 1, wherein the cumulative total amount of asparagine per unit volume in said medium is greater than 8 mM.

93. The method of claim 1, wherein the cumulative total amount of asparagine per unit volume in said medium is greater than 12 mM.

94. The method of claim 1, wherein the initial total amount of asparagine per unit volume in said medium is greater than 8 mM.

95. The method of claim 1, wherein the initial total amount of asparagine per unit volume in said medium is greater than 12 mM.

96. The method of claim 1, wherein the cumulative total amount of phosphorous per unit volume in said medium is greater than 2.5 mM.

97. The method of claim 1, wherein the cumulative total amount of phosphorous per unit volume in said medium is greater than 5 mM.

98. The method of claim 1, wherein the cumulative total amount of glutamate per unit volume in said medium is less than 1 mM.

99. The method of claim 1, wherein the cumulative total amount of calcium pantothenate per unit volume in said medium is greater than 8 mg/L.

100. The method of claim 1, wherein the cumulative total amount of calcium pantothenate per unit volume in said medium is greater than 20 mg/L.

101. The method of claim 1, wherein the cumulative total amount of nicotinamide per unit volume in said medium is greater than 7 mg/L.

102. The method of claim 1, wherein the cumulative total amount of nicotinamide per unit volume in said medium is greater than 25 mg/L.

103. The method of claim 1, wherein the cumulative total amount of pyridoxine and pyridoxal per unit volume in said medium is greater than 5 mg/L.

104. The method of claim 1, wherein the cumulative total amount of pyridoxine and pyridoxal per unit volume in said medium is greater than 35 mg/L.

105. The method of claim 1, wherein the cumulative total amount of riboflavin per unit volume in said medium is greater than 1.0 mg/L.

106. The method of claim 1, wherein the cumulative total amount of riboflavin per unit volume in said medium is greater than 2.0 mg/L.

107. The method of claim 1, wherein the cumulative total amount of thiamine hydrochloride per unit volume in said medium is greater than 7 mg/L.

108. The method of claim 1, wherein the cumulative total amount of thiamine hydrochloride per unit volume in said medium is greater than 35 mg/L.

* * * * *